(12) United States Patent
Peles

(10) Patent No.: US 6,465,210 B1
(45) Date of Patent: Oct. 15, 2002

(54) NUCLEIC ACID MOLECULES ENCODING CASPR/P190

(75) Inventor: Elior Peles, Foster City, CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 08/826,134

(22) Filed: Mar. 26, 1997

Related U.S. Application Data

(60) Provisional application No. 60/014,199, filed on Mar. 27, 1996.

(51) Int. Cl.[7] .................. C07H 21/04; C12N 15/00; C12N 1/20; C12P 21/04
(52) U.S. Cl. ................. 435/69.1; 435/70.1; 435/71.1; 435/71.2; 435/243; 435/252.3; 435/254.2; 435/320.1; 435/325; 536/23.5
(58) Field of Search .................... 536/23.1, 23.5; 435/69.1, 70.1, 71.1, 71.2, 325, 243, 252.3, 320.1, 254.2

(56) References Cited

PUBLICATIONS

Bare et al., 1993, "p59$^{fyn}$ in Rat Brain is Localized in Developing Axonal Tracts and Subpopulations of Adult Neuron and Glia", Oncogene 8:1429–1436.
Barnea et al., 1993, "Close Similarity Between Receptor–Linked Tyrosine Phosphatase and Rat Brain Proteoglycan", Cell 76:205.
Barnea et al., 1994, "Receptor Tyrosine Phosphatase β is Expressed in the Form of Proteoglycan and Binds to the Extracellular Matrix Protein Tenascin", J. Biol. Chem. 269:14349–14352.
Barnea et al., 1993, "Identification of a Carbonic Anhydrase–Like Domain in the Extracellular Region of RPTPγ Defines a New Subfamily of Receptor Tyrosine Phosphatases", Mol. Cell. Biol. 13:1497–1506.
Beggs et al., 1993, "NCAM–Dependent Neurite Outgrowth is Inhibited in Neurons from fyn–Minus Mice", J. Cell. Biol. 127:825–833.
Berglund and Ranscht, 1994, "Molecular Cloning and in situ Localization of the Human Contactin Gene (CNTN1) on Chromosome 12q11–q12", Genomics 21:571–582.
Brady–Kalany et al., 1993, "Homophilic Binding of PTPμ, a Receptor–Type Protein Tyrosine Phosphatase, Can Mediate Cell–Cell Aggregation", J. Cell Biol. 122:961–972.
Brümmendorf et al., 1993, "The Axonal Recognition Molecule F11 is a Multifunctional Protein: Specific Domains Mediate Interactions with Ng–CAM and Restrictin", Neuron 10:711–727.
Brümmendorf and Rathjen, 1993, "Axonal Glycoproteins with Immunoglobulin– and Fibronectin Type III–Related Domains in Vertebrates: Structural Features, Binding Activities, and Signal Transduction", J. Neurochem. 61:1207–1219.

Brümmendorf et al., "Neural Cell Recognition Molecule F11: Homology with Fibronectin Type III and Immunoglobulin Type C Domains", Neuron 2:1351–1361.
Canoll et al., 1993, "The Expression of a Novel Receptor–Type Protein Tyrosine–Phosphatase Suggests a Role in Morphogenesis and Plasticity of the Nervous System", Dev. Brain Res. 75:293–298.
Chao, 1992, "Neurotropin Receptors: A Window into Neuronal Differentiation", Neuron 9:583–593.
Charbonneau and Tonks, 1992, "1002 Protein Phosphatase?", Annu. Rev. Cell Biol. 8:463–493.
Clarke et al., 1993, "Substrate–Bound GP130/F11 Will Promote Neurite Outgrowth: Evidence for a Cell Surface Receptor", Eur. J. Cell Biol. 61:108–115.
Cunningham et al., 1987, "Neural Cell Adhesion Molecule: Structure, Immunoglobulin–Like Domains, Cell Surface Modulation, and Alternative RNA Splicing", Science 236:799–806.
den Hertog et al., 1993, "Receptor Protein Tyrosine Phosphatase α Activates pp60$^{c-src}$ and is Involved in Neuronal Differentiation", EMBO J. 12:3789–3798.
Dodd et al., 1988, "Spatial Regulation of Axonal Glycoprotein Expression on Subsets of Embryonic Spinal Neurons", Neuron 1:105–116.
Doherty and Walsh, 1994, "Signal Transduction Events Underlying Neurite Outgrowth Stimulated by Cell Adhesion Molecules", Curr. Opin. Neurobiol. 4:49–55.
Durbec et al., 1994, "Different Domains of the F3 Neuronal Adhesion Molecule are Involved in Adhesion and Neurite Outgrowth Promotion", Eur. J. Neurol. 6:461–472.
Durbec et al., 1992, "A Soluble Form of the F3 Neuronal Cell Adhesion Molecule Promotes Neurite Outgrowth", J. Cell. Biol. 117:877–887.
Edelman and Crossin, 1991, "Cell Adhesion Molecules: Implications for a Molecular Histology", Annu. Rev. Biochem. 60:155–190.
Erpel et al., 1995, "Mutational Analysis of the Src SH3 Domain: the Same Residues of the Ligand Binding Surface are Important for Intra– and Intermolecular Interactions", EMBO J. 14:963–975.
Faivre–Sarrilh et al., 1992, "F3/F11 Cell Surface Molecule Expression in the Developing Mouse Cerebellum is Polarized at Synaptic Sites and Within Granule Cells", J. Neurosci. 12:257–267.

(List continued on next page.)

Primary Examiner—Patricia A. Duffy
(74) Attorney, Agent, or Firm—Foley & Lardner

(57) ABSTRACT

The 190 kDa Contactin ASsociated PRotein (CASPR/p190) is identified and is implicated as the bridge between contactin and intracellular second messenger systems for the signal caused by the binding of the carboxy anhydrase domain of RPTPβ to contactin and resulting in neurite growth, differentiation or survival. Mammalian CASPR/p190 cDNAs and proteins are described, including those from human and rat. In addition, particular domains of the proteins are characterized.

23 Claims, 2 Drawing Sheets

OTHER PUBLICATIONS

Friedman et al., 1994, "The Search for BRCA1", Cancer Res. 54:6374–6382.

Furley et al., 1990, "The Axonal Glycoprotein TAG–1 is an Immunoglobulin Superfamily Member with Neurite Outgrowth–Promoting Activity", Cell 61:157–170.

Gebbink et al., 1993, "Cell–Cell Adhesion Mediated by a Receptor–Like Protein Tyrosine Phosphatase", J. Biol. Chem. 268:16101–16104.

Gennarini et al., 1989, "The Mouse Neuronal Cell Surface Protein F3: a Phosphatidylinositol–Anchored Member of the Immunoglobulin Superfamily Related to Chicken Contactin", J. Cell Biol. 109:755–788.

Gloor et al., 1990, "The Adhesion Molecule on Glia (AMOG) is a Homologue of the β Subunit of the Na, K–ATPase", J. Cell Biol. 110:165–174.

Goodman and Shatz, 1993, "Developmental Mechanisms that Generate Precise Patterns of Neuronal Connectivity", Cell vol. 72/Neuron vol. 10 (Suppl.):77–98.

Grumet et al., 1994, "Interactions with Tenascin and Differential Effects on Cell Adhesion of Neurocan and Phosphacan, Two Major Chondroitin Sulfate Proteoglycans of Nervous Tissue", J. Biol. Chem. 269:12142–12146.

Grumet et al., 1993, "Functional Characterization of Chondroitin Sulfate Proteoglycans of Brain! Interactions with Neurons and Neural Cell Adhesion Molecules", J. Cell Biol. 120:815–824.

Grumet, 1992, "Structure, Expression, and Function of Ng–CAM, a Member of the Immunoglobulin Superfamily Involved in Neuron–Neuron and Neuron–Glia Adhesion", J. Neurosci. Res. 31:1–13.

Hasler et al., 1993, "cDNA Cloning, Structural Features, and Eucaryotic Expression of Human TAG–1/Axonin–1", Eur. J. Biochem. 211:329–339.

Hunter, 1995, "Protein Kinases and Phosphatases: the Yin and Yang of Protein Phosphorylation and Signalling", Cell 80:225–236.

Hynes and Lander, "Contact and Adhesive Specificities in the Associations, Migrations and Targeting of Cells and Axons", Cell 68:303–322.

Ignelzi et al., 1994, "Impaired Neurite Outgrowth of src–Minus Cerebellar Neurons on the Cell Adhesion Molecule L1", Neuron 12:873–884.

Jacob et al., 1995, "Molecular Cloning and Expression Pattern of Genes from a 470 Kb Region Near BRCA1 Locus on Chromosome 17q21", Oncogene 11:981–986.

Jenny et al., 1987, "Complete cDNA and Derived Amino Acid Sequence of Human Factor V", Proc. Natl. Acad. Sci. USA 84:4846–4850.

Keynes and Cook, 1992, "Repellent Cues in Axon Guidance", Curr. Opin. Neurobiol. 2:55–59.

Kris et al., 1985, "Antibodies Against a Synthetic Peptide as a Probe for the Kinase Activity of the Avian EGF Receptor and v–erbB Protein", Cell 40:619–625.

Krueger and Saito, 1992, "A Human Transmembrane Protein–Tysrosine–Phosphatase, PTPξ, is Expressed in Brain and has an N–Terminal Receptor Domain Homologous to Carbonic Anhydrases", Proc. Natl. Acad. Sci. USA 89:7417–7421.

Levy et al., 1993, "The Cloning of a Receptor–Type Protein–Tyrosine Phosphatase Expressed in the Central Nervous System", J. Biol. Chem. 268:10573–10581.

Maa et al., 1990, "Structural and Functional Characterization of a Cell Surface Binding Protein of Vaccinia Virus", J. Biol. Chem. 265:1569–1577.

Maness et al., 1994, "c–src Gene Product in Developing Rat Brain is Enriched in Nerve Growth Cone Membranes", Proc. Natl. Acad. Sci. USA 85:5001–5005.

Maurel et al., 1994, "Phosphacan, a Chondroitin Sulfate Proteoglycan of Brain that Interacts with Neurons and Neural Cell–Adhesion Molecules, is an Extracellular Variant of a Receptor–Type Protein Tyrosine Phosphatase", Proc. Natl. Acad. Sci USA 91:2512–2516.

Milev et al., 1994, "Interactions of the Chondroitin Sulfate Proteoglycan Phosphacan, the Extracellular Domain of a Receptor–Type Protein–Tysrosine Phosphatase, with Neurons, Glia, and Neural Cell Adhesion Molecules", J. Cell Biol. 127:1703–1715.

Milev et al., 1995, "Complex–Type Asparagine–Linked Oligosaccharides on Phosphacan and Protein–Tyrosine Phosphatase–ξ–β Mediate Their Binding to Neural Cell Adhesion Molecules and Tenascin", J. Biol. Chem. 270:24650–24653.

Morales et al., 1993, "Induction of Axonal Growth by Heterophilic Interactions Between the Cell Surface Recognition Proteins F11 and Nr–CAM/Bravo", Neuron 11:1113–1122.

Olive et al., 1995, "The F3 Neuronal Glycosylphosphatidylinositol–Linked Molecule is Localized to Glycolipid–Enriched Membrane Subdomains and Interacts with L1 and fyn Kinase in the Cerebellum", J. Neurochem, 65:2307–2317.

Peles et al., 1995, "The Carbonic Anhydrase Domain of Receptor Tyrosine Phosphatase β is a Functional Ligand for the Axonal Cell Recognition Molecule Contactin", Cell 82:251–260.

Peles et al., 1993, "Cell–Type Specific Interaction of Neu Differentiation Factor (NDF/heregulin) with Neu/HER–2 Suggests Complex Ligand–Receptor Relationships", EMBO J. 12:961–971.

Peles et al., 1992, "Isolation of the Neu/HER–2 Stimulatory Ligand: a 44kd Glycoprotein that Induces Differentiation of Mammary Tumor Cells", Cell 69:205–216.

Peles et al., 1991, "Oncogenic Forms of the neu/HER2 Tyrosine Kinase are Permanently Coupled to Phospholipase Cγ", EMBO J. 10:2077–2086.

Pesheva et al., 1993, "The F3/11 Cell Adhesion Molecule Mediates the Repulsion of Neurons by the Extracellular Matrix Glycoprotein J1–160/180", Neuron 10:69–82.

Pulido et al., 1992, "Dtrk, a Drosophila Gene Related to the trk Family of Neurotrophin Receptors, Encodes a Novel Class of Neural Cell Adhesion Molecules", EMBO J. 11:391–404.

Ranscht, 1988, "Sequence of Contactin, a 130–kD Glycoprotein Concentrated in Areas of Interneuronal Contact, Defines a New Member of the Immunoglobulin Supergene Family in the Nervous System", J. Cell. Biol. 107:1561–1573.

Rao and Hausman, 1993, "cDNA for R–Cognin: Homology with a Multifunctional Protein", Proc. Natl. Acad. Sci. USA 90:2950–2954.

Rathjen et al., 1991, "Glycoproteins that Regulate the Growth and Guidance of Vertebrate Axons: Domains and Dynamics of the Immunoglobulin/Fibronectin Type III Subfamily", Semin. Neurosci. 3:297–307.

Rathjen et al., 1987, "Membrane Glycoproteins Involved in Neurite Fasciculation", J. Cell Biol. 104:343–353.

Reid et al., 1994, "Identification and Characterization of the Human Cell Adhesion Molecule Contactin", Mol. Brain Res. 21:1–8.

Rothberg et al., 1988, "slit: and EGF–Homologous Locus of *D. melanogaster* Involved in the Development of the Embryonic Central Nervous System", Cell 55:1047–1059.

Rougon et al., 1994, "Functional Studies and Cellular Distribution of the F3 GPI–Anchored Adhesion Molecule", Braz. J. Med. Biol. Res. 2:409–414.

Sahin et al., 1995, "Seven Protein Tyrosine Phosphatases Are Differently Expressed in the Developing Rat Brain", J. Comp. Neurol. 351:617–631.

Sap et al., 1994, "Receptor Tyrosine Phosphatase R–PTP–κ Mediates Homophilic Binding", Mol. Cell. Biol. 14:1–9.

Schachner et al., 1994, "The Perplexing Multifunctionality of Janusin, a Tenascin–Related Molecule", Perspect. Dev. Neurobiol. 2:33–41.

Schlessinger and Ullrich, 1992, "Growth Factor Signaling by Receptor Tyrosine Kinases", Neuron 9:383–391.

Sharma and Lombroso, 1995, "A Neuronal Protein Tyrosine Phosphatase Induced by Nerve Growth Factor", J. Biol. Chem. 270:49–53.

Shitara et al., 1994, "Brain–Specific Receptor–Type Protein–Tyrosine Phosphatase RPTPβ is a Chondroitin Sulfate Proteoglycan in Vivo", J. Biol. Chem. 269:20189–20193.

Shock et al., 1995, "Protein Tyrosine Phosphatases Expressed in Developing Brain and Retinal Müller Glia", Mol. Brain Res. 28:110–116.

Sonderegger et al., 1992, "Regulation of Axonal Growth and the Vertebrate Nervous System by Interactions between Glycoproteins Belonging to Two Subgroups of the Immunoglobulin Superfamily", J. Cell Biol. 119:1387–1394.

Sudol et al., 1988, "Differential Development Expression of Cellular yes and Cellular src Proteins in Cerebellum", Oncogene Res. 2:345–355.

Takagi et al., 1991, "The A5 Antigen, a Candidate for the Neuronal Recognition Molecule, has Homologies to Complement Components and Coagulation Factors", Neuron 7:295–307.

Théveniau et al., 1992, "Expression and Release of Phosphatidylinositol Anchored Cell Surface Molecules by a Cell Line Derived from Sensory Neurons", J. Cell. Biochem. 48:61–72.

Umemori et al., 1994, "Initial Events of Myelination Involve Fyn Tyrosine Kinase Signalling", Nature 367:572–576.

Ushkaryov et al., 1992, "Neurexins: Synaptic Cell Surface Proteins Related to the α–Latrotoxin Receptor and Laminin", Science 267:50–56.

Walsh and Doherty, 1991, "Glycophosphatidylinositol Anchored Recognition Molecules that Function in Axonal Fasciculation, Growth and Guidance in the Nervous System", Cell Biol. Int. Rep. 15:1151–1166.

Walton et al., 1993, "A Novel Receptor–Type Protein Tyrosine Phosphatase is Expressed During Neurogenesis in the Olfactory Neuroepithelium", Neuron 11:387–400.

Wharton et al., 1985, "Nucleotide Sequence from the Neurogenic Locus Notch Supplies a Gene Product that Shares Homology with Proteins Containing EGF–Like Repeats", Cell 43:567–581.

Wood et al., 1984, "Expression of Active Human Factor VIII from Recombinant DNA Clones", Nature 312:330–337.

Yoshihara et al., 1994, "BIG–1: a New TAG–1/F3–Related Member of the Immunoglobin Superfamily with Neurite Outgrowth–Promoting Activity", Neuron 13:415–426.

Zhang and Long, 1995, "LAR Tyrosine Phosphatase Receptor: Alternative Splicing is Preferential to the Nervous System, Coordinated with Cell Growth and Generates Novel Isoforms Containing Extensive CAG Repeats", J. Cell Biol. 128:415–431.

Zipursky and Rubin, 1994, "Determination of Neuronal Cell Fate: Lessons from the R7 Neuron of Drosophila", Annu. Rev. Neurosci. 17:373–397.

Zisch et al., 1992, "The Glypiated Neuronal Cell Adhesion Molecule Contactin/F11 Complexes with src–Family Protein Tyrosine Kinase Fyn", Mol. Cell. Neurosci. 6:263–279.

Zisch et al., 1992, "Neuronal Cell Adhesion Molecule Contactin/F11 Binds to Tenascin Via Its Immunoglobulin–Like Domains", J. Cell Biol. 119:203–213.

Zuellig et al., 1992, "The Axonally Secreted Cell Adhesion Molecule, Axonin–1", Eur. J. Biochem. 204:453–463.

GenBank Accession No. T27171, publically available Sep. 5, 1995.*

GenBank Accession No. M83730, publically available Dec. 3, 1994.*

American Type Culture Collection, Catalogue of Cell Lines & Hybridomas, $7^{th}$ edition, 1992 pp. 49, 72–73 and 213–214.*

Friedman et al, Cancer Research 54(24):6374–6382, 1994.*

Jacob et al, Oncogene, 11(5):981–986, 1995.*

Sambrook et al, Molecular Cloning:A Laboratory Manual chapters 16 & 17, 1989, by Cold Spring Harbor Press.*

Chomczynski, P., and N. Sacchi (1987). Single–step method of RNA isolation by acid guanidinium thiocyanate–phenol–cholorform extraction. Analytical Biochemistry 162:156–159.

D'Allesandri, L., B. Ranscht, K.H. Winterhalter, and L. Vaughan. (1995) Contactin/F11 and tenascin–C co–expression in the chick retina correlates with formation of the synaptic plexiform layers. Current Eye Research 14:911–926.

Friedlander, D.R., et al. (1994). The neuronal chondroitin sulfate proteoglycan neurocan binds to the neural cell adhesion molecules Ng–CAM/L1/NILE and N–CAM, and inhibits neuronal adhesion and neurite outgrowth. The Journal of Cell Biology 125:669–680.

Gennarini, G., G. Rougon, F. Vitiello, C. Di Benedetta, and C. Goridis. 1989. Identification and cDNA cloning of a new member of the L2/HNK–1 family neural sufrace glycoproteins. Journal of Neuroscience Research 22:1–12.

Gennarini, G., P. Durbec, and C. Goridis. 1991. Transfected F3/F11 neuronal cell surface protein mediates intercellular adhesion and promotes neurite outgrowth. Neuron 6:595–606.

Hawrot, E., and P. H. Patterson. 1979. Long–term culture of disassociated sympathetic neurons. Methods in Enzymology 53:574–585.

Hosoya, H., K. Shimazaki, S. Kobayashi, H. Takahashi, T. Shirasawa, T. Takenawa, and K. Watanabe. 1995. Developmental expression of the neural adhesion molecule F3 in the rat brain. Neuroscience Letters 186:83–86.

Huse, W.D., L. Sastry, S.A. Iverson, A.S. Kang, M. Alting–Mees, D.R. Burton, S.J. Benkovic, and R.A. Lerner. 1989. Generation of a large combinatorial library of the immunoglobulin repertoire in phage lambda. Science 246:1275–1281.

Krishna Rao, A.S.M., and R.E. Hausman. 1993. cDNA for R–cognin; homology with a multifunctional protein. Proc. Natl. Acad. Sci. USA 90:2950–2954.

Lammers, R. B. Bossenmaier, D.E. Cool, N.K. Tonks, J. Schlessinger, E.H. Fischer, and A. Ullrich. 1993. Differential activities of protein tyrosine phosphatases in intact cells. The Journal of Biological Chemistry 268:22456–22462.

Lüdecke, G., and K. Unsicker. 1990. Mitogenic effect of neurotrophic factors on human IMR 32 neuroblastoma cells. Cancer 65:2270–2278.

Muller, A.J. et al. 1991. BCR first exon sequences specifically activate the BCR/ABL tyrosine kinase oncogene of Philadelphia chromosome–positive human leukemias. Molecular and Cellular Biology 11:1785–1792.

Nürenberg, U., H. Willie, J.M. Wolff, R. Frank, and F.G. Rathjen. 1992. The chicken neural extracellular matrix molecule restrictrin: similarity with EGF–, fibronectin type III–, and fibrinogen–like motifs. Neuron 8:849–863.

Olive, S. et al. 1995. Expression of a glycosyl phosphatidylinositol–anchored adhesion molecule, the glycoprotein F3, in the adult rat hypothalamo–neurohypophysial system. Brain Research 689:271–280.

Plowman, G.D. et al. 1992. The epithelin precursor encodes two proteins with opposing activities on epithelial cell growth. The Journal of Biological Chemistry 267:13073–13078.

Sarrailh, C.F. 1992. F3/F11 cell surface molecule expression in the development mouse cerebellum is polaized at synaptic sites and within granule cells. The Journal of Neuroscience 12:257–267.

Sarrailh, C.F., and G. Rougon. 1993. Are the glypiated adhesion molecules preferentially targeted to the axonal compartment? Molecular Neurobiology 7:49–60.

Simmons, D.L. 1993. Cloning cell surface molecules by transient expression in mammalian cells. Cellular Interactions in Development, A Practical Approach, 93–127.

Theodosis, D.T., L. Bonfanti, S. Olive, G. Rougon, and D.A. Poulain. 1994. Adhesion molecules and structural plasticity of the adult hypothalamo–neurohypophysial system. Psychoneuroendocrinology 19:455–462.

Vaughn, L., P. Weber, L. D'Alessandri, A.H. Zisch, and K.H. Witherhalter. 1994. Tenascin–contactin/F11 interactions; a clue for the development role? Perspectives on Developmental Neurobiology 2:43–52.

Wolff, J.M., F.G. Rathjen, and S. Roth. 1987. Biochemical characterization of polypeptide components involved in neurite fasciculation and elongation. Eur. J. Biochem. 168:551–561.

* cited by examiner

FIG. 1A

```
Caspr_h MMHLRLFCILLAAV-SGAEGWGYYGCDEELVGPLYARSLGASSYYSLLTAPRFARLHGIS  59
Caspr_r ...S....S......V...Q.......N............G.F.TA........       60      DISC Caspr_h GWSPRIGDPNPWLQIDLMKKHRIRAVATQGSFNSWDWVTRYMLLYGDRVDSWTPFYQRGH 119
Caspr_r ....................A..............................Q..     120

Caspr_h NSTFFGNVNESAVVRHDLHFHFTARYIRIVPLAWNPRGKIGLRLGLYGCPYKADILYFDG 179
Caspr_r .A......D.......Y.............I...TSN......                 180

Caspr_h DDAISYRFPRGVSRSLWDVFAFSFKTEEKDGLLLHAEGAQGDYVTLELEGAHLLLHMSLG 239
Caspr_r ........Q..A.Q..................T..S.........Q...........  240      NX1

Caspr_h SSPIQPRPGHTTVSAGGVLNDQHWHYVRVDRFGRDVNFTLDGYVQRFILNGDFERLNLDT 299
Caspr_r ................LS......Y..EA.L......H..V..........EN      300

Caspr_h EMFIGGLVGAARKNLAYRHNFRGCIENVIFNRVNIADLAVRRHSRITFEGKVAFRCLDPV 359
Caspr_r .I............Y..I...EM..Q.........N........               360

Caspr_h PHPINFGGPHNFVQVPGFPRRGRLAVSFRFRTWDLTGLLLFSRLGDGLGHVELTLSEGQV 419
Caspr_r ..|.........................................M......        420

Caspr_h NVSIAQSGRKKLQFAAGYRLNDGFWHEVNFVAQENHAVISIDDVEGAEVRVSYPLLIRTG 479
Caspr_r ......T.....................................               480      NX2

Caspr_h TSYFFGGCPKPASRWDCHSNQTAFHGCMELLKVDGQLVNLTLVEGRRLGFYAEVLFDTCG 539
Caspr_r .......G................................F.K..YF.........   540

Caspr_h ITDRCSPNMCEHDGRCYQSWDDFICYCELTGYKGETCHIPLYKESCEAYRLSGKTSGNFT 599
Caspr_r ....................V...E............Y...Y.                600      EGF1

Caspr_h IDPDGSGPLKPFVVYCDIRENRAWTVVRHDRLWTTRVTGSSMERPFLGAIQYWNASWEEV 659
Caspr_r ..........................................D......         660      FIB Caspr_h SALANASQHCEQWIEFSCYNSRLLNTAGGYPYSFWIGRNEEQHFYWGGSQPGIQRCACGL 719
Caspr_r .............................................              720

Caspr_h DRSCVDPALYCNCDADQPQWRTDKGLLTFVDHLPVTQVVIGDTNRSTSEAQFFLRPLRCY 779
Caspr_r .Q..I....H.........................S......                  780
```

FIG. 1B

```
Caspr_h GDRNSWNTISFHTGAALRFPPIRANHSLDVSFYFRTSAPSGVFLENMGGPYCQWRRPYVR 839
Caspr_r ..........R.................................F.......... 840    NX3
Caspr_h VELNTSRDVVFAFDVGNGDENLTVHSDDFEFNDDEWHLVRAEINVKQARLRVDHRPWVLR 899
Caspr_r ..............I............................................ 900
Caspr_h PMPLQTYIWMEYDQPLYVGSAELKRRPFVGCLRAMRLNGVTLNLEGRANASEGTSPNCTG 959
Caspr_r .............L........................................F.... 960
Caspr_h HCAHPRLPCFHGGRCVERYSYYTCDCDLTAFDGPYCNHDIGGFFEPGTWMRYNLQSALRS 1019  EGF2
Caspr_r ..T...F..................................T................ 1020
Caspr_h AAREFSHMLSRPVPGYEPGYIPGYDTPGYVPGYHGPGYRLPDYPRPGRPVPGYRGPVYNV 1079  PGY
Caspr_r ..Q......................................................... 1080
Caspr_h TGEEVSFSFSTSSAPAVLLYVSSFVRDYMAVLIKDDGTLQLRYQLGTSPYVYQLTTRPVT 1139
Caspr_r ...................................E....................... 1140  NX4
Caspr_h DGQPHSINITRVYRNLFIQVDYFPLTEQKFSLLVDSQLDSPKALYLGRVMETGVIDPEIQ 1199
Caspr_r ......V..................................................... 1200
Caspr_h RYNTPGFSGCLSGVRFNNVAPLKTHFRTPRPMTAELAEALRVQGELSESNCGAMPRLVSE 1259
Caspr_r ..............................M............................ 1260
Caspr_h VPPELDPWYLPPDFPYYHDEGWVAILLGFLVAFLLLGLVGMLVLFYLQNHRYKGSYHTNE 1319  TMD
Caspr_r ..................D..I..................................... 1320
Caspr_h PKAAHEYHPGSKPPLPTSGPAQVPTPTAAPNQAPASAPAPAPTPAPAPGPRDQNLPQILE 1379  PRO
Caspr_r ...T.DS...G.A...P.....A.A...P..T.V----.T....A..SG........... 1376
Caspr_h ESRSE 1384
Caspr_r ..... 1381
```

NUCLEIC ACID MOLECULES ENCODING CASPR/P190

The present application claims priority under 35 U.S. § 119(e) to provisional application Ser. No. 60/014,199, filed Mar. 27, 1996, the entire contents of which is incorporated herein by reference in its entirety.

1. INTRODUCTION

The present invention relates to the 190 Kd neuronal protein (hereinafter "p190", "CASPR" or "CASPR/p190") that interacts with contactin, and with the carbonic anhydrase ("CAH") domain of the receptor-type tyrosine phosphatase RPTP-β, specific peptides thereof and nucleic acid molecules encoding such p190 proteins and peptides. The protein is also referred to as CASPR, for Contactin ASsociated PRotein. The CAH domain of RPTPβ has previously been identified as a ligand for contactin, and the binding of the CAH domain of RPTPβ to the contactin on neural cells results in neurite growth, differentiation and survival. CASPR/p190 has been identified as a potential bridge that couples contactin, a GPI-linked protein, with intracellular second messenger systems. The invention also relates to compounds that mimic, enhance, or suppress the effects of p190, including those molecules which act downstream in the signal transduction pathway that results from the binding of the ligand to contactin. In addition, the invention also relates to the use of such compounds to treat neurologic diseases including those characterized by insufficient, aberrant, or excessive neurite growth, differentiation or survival.

2. BACKGROUND OF THE INVENTION

The ability of cells to respond to signals from their microenvironment is a fundamental feature of development. In the developing nervous system, neurons migrate and extend axons to establish their intricate network of synaptic connections (Goodman and Shatz, 1993, Cell/Neuron (Suppl.), 72/10:77–98). During migration and axonal pathfinding, cells are guided by both attractive and repulsive signals (Hynes and Lander, 1992, Cell, 68:303–322; Keynes and Cook, 1992, Lurr. Opin. Neurobiol., 2:55–59). The ability of the neuron to respond to these signals requires cell surface molecules that are able to receive the signal and to transmit it to the cell interior resulting in specific biological responses.

It is well established that protein tyrosine phosphorylation is responsible for the regulation of many cellular responses to external stimuli crucial for cell growth, proliferation and differentiation (Schlessinger and Ullrich, 1992, Neuron, 9:383–391). Tyrosine phosphorylation has been implicated in several developmental processes in the nervous system. For example, receptor tyrosine kinases were shown to effect neuronal survival (Chao, 1992, Neuron, 9:583–593), and cell fate determination (Zipursky and Rubin, 1994, Annu. Rev. Neurosci., 17:373–397). Non-receptor tyrosine kinases have been shown to be downstream elements in signaling via cell recognition molecules that play a role in cell guidance and migration (Ignelzi et al., 1994, Neuron, 12:873–884; Umemori et al., 1994, Nature, 367–572–586).

The transient nature of signaling by phosphorylation requires specific phosphatases for control and regulation (Hunter, 1995, Cell, 80:225–236). Indeed, many protein tyrosine phosphatases have been shown to be expressed in specific regions of the developing brain, including the olfactory neuroepithelium (Walton et al., 1993, Neuron, 11:387–400), the cortex (Sahin et al., 1995, J. Comp. Neurol., 351:617–631), and in retinal Müller glia (Shock et al., 1995, Mol. Brain Res., 28:110–116). Furthermore, expression of several tyrosine phosphatases, such as PTPα (den Hertog et al., 1993, EMBO J., 12:3789–3798), PC12-PTP1 (Sharama and Lombroso, 1995, J. Biol. Chem., 270:49–53) and several forms of LAR (Zhang and Longo, 1995, J. Cell. Biol., 128:415–431) have been found to be regulated during neural differentiation of P19 or PC12 cells.

Receptor-type tyrosine phosphatases (RPTPs) have been subdivided into several groups based on structural characteristics of their extracellular domains (Charbonneau and Tonks, 1992, Annu. Rev. Cell Biol., 8:463–493; Barnea et al., 1993, Mol. Cell. Biol., 13:1497–1506). RPTPβ/ζ and RPTPγ are members of a distinct group of phosphatases, characterized by the presence of a carbonic anhydrase-like domains (CAH), fibronectin type III repeats (FNIII), and a long cysteine free region (spacer domain) in their extracellular domain (Barnea et al., 1993, Mol. Cell. Biol., 13:1497–1506; Krueger et al., 1992, Proc. Natl. Acad. Sci. USA, 89:7417–7421; Levy et al., 1993, J. Biol. Chem., 268:10573–10581). The expression of RPTPβ is restricted to the central and peripheral nervous system, while RPTPγ is expressed both in the developing nervous system, as well as, in a variety of other tissues in adult rat (Canoll et al., 1993, Dev. Brain Res., 75:293–298; Barnea et al., 1993, Mol. Cell. Biol., 13:1497–1506). RPTPβ exists in three forms, one secreted form and two membrane bound forms, that differ by the absence of 860 residues from the spacer domain (Levy et al., 1993, J. Biol. Chem., 268:1053–10582; Maurel et al., 1994, Proc. Natl. Acad. Sci. USA, 91:2512–2516). The secreted form has been identified as a chondroitin sulfate proteoglycan from rat brain called phosphocan (3F8 proteoglycan) (Barnea et al., 1994, Cell, 76:205; Maurel et al., 1994, Proc. Natl. Acad. Sci. USA, 91:2512–2516; Shitara et al., 1994, J. Biol. Chem. 269:20189–20193). The transmembrane form has also been shown to be expressed in a form of a chondroitin sulfate proteoglycan (Barnea et al., 1994, J. Biol. Chem., 269:14349–14352). Purified phosphocan can interact in vitro with the extracellular matrix protein tenascin, and with the adhesion molecules, N-CAM and Ng-CAM (Barnea et al., 1994, J. Biol. Chem., 269:14349–14352; Grumet et al., 1993, J. Cell. Biol., 120:815–824; Grumet et al., 1994, J. Biol. Chem., 269:12142–12146; Milev et al., 1994, J. Cell. Biol., 127:2512–2516).

3. SUMMARY OF THE INVENTION

The present invention relates to the 190 Kd neuronal protein (hereinafter "p190", "CASPR" or "CASPR/p190") that interacts with contactin, and with the carbonic anhydrase ("CAH") domain of the receptor-type tyrosine phosphatase RPTP-β, specific peptides thereof and nucleic acid molecules encoding such p190 proteins and peptides.

The invention further relates to the use of p190 and related compounds to treat neurologic diseases including those characterized by insufficient, aberrant, or excessive neurite growth, differentiation or survival. More specifically, the invention relates to the use of compounds that mimic, enhance or suppress the effects of p190 on neurite growth, differentiation and survival.

The invention is based, in part, on the discovery that the CAH domain of RPTPβ (RPTPβ-CAH) is the ligand for contactin and that its binding results in neurite growth, differentiation and survival, and on the further discovery that p190 acts as the bridge between contactin and intracellular second messenger systems.

In the examples described infra, it is shown that receptor phosphatase RPTPβ specifically interacts with two ligands, one on the surface of glial cells, and the other on the surface of neuronal cells. Using expression cloning in COS7 cells and bioaffinity purification, the neuronal ligand was identified to be the rat homologue of the cell recognition molecule contactin (F11/F3). Using combinations of soluble and membrane bound forms of RPTPβ and contactin it is demonstrated that the reciprocal interaction between the two molecules is mediated by the CAH domain of the phosphatase. Moreover, it is found that when used as a substrate, the CAH domain of RPTPβ induced neurite growth, differentiation and survival of primary neurons and IMR-32 neuroblastoma cells. Using antibody perturbation experiments, the contactin ligand was found to be a neuronal receptor for the CAH domain of RPTPβ. The data indicate that the interactions between contactin, a cell recognition molecule, and RPTBβ, a transmembrane protein tyrosine phosphatase, plays an important role in neuronal development and differentiation. As explained more fully in Section 5.2, the further experiments of the examples were conducted to elucidate the interaction between contactin and intracellular second messenger systems. Binding experiments revealed that the interaction between p190 and contactin is important for the role of contactin and RPTPβ-CAH in neuronal growth, development and differentiation.

3.1. DEFINITIONS

As used herein, the following terms and abbreviations shall have the meanings indicated below:

TABLE 1

| base pair (s) | bp |
| carbonic anhydrase | CAH |
| carbonic anhydrase domain of RPTPβ | RPTPβ |
| complementary DNA | cDNA |
| counts per minute | cpm |
| deoxyribonucleic acid | DNA |
| fibronectin type III | FNIII |
| glycosyl-phosphatedylinositol | GPI |
| kilobase pairs | kb |
| kilodation | kDa |
| micrograms | μg |
| micrometer | μm |
| nanograms | ng |
| nanometer | nm |
| nucleotide | nt |
| phospholipase C | PI-PLC |
| polyacrylamide gel electrophoresis | PAGE |
| polymerase chain reaction | PCR |
| receptor type tyrosine phosphatase beta | RPTPβ |
| ribonucleic acid | RNA |
| sodium dodecyl sulfate | SDS |
| units | u |

As used herein, the word "modulate" shall have its usual meaning, but shall also encompass the meanings of the words enhance, inhibit, and mimic. In addition, as used herein, the word "expression", when used in connection with a gene such as p190, shall have its usual meaning, but shall also encompass the transcription of the gene, the longevity of the functional mRNA transcribed from the gene, the translation of that mRNA, and the activity of the gene product.

4. DESCRIPTION OF THE DRAWINGS

FIGS. 1A and 1B show the homology between human and rat CASPR/p190 proteins. Also shown are the important domains of the proteins as more fully described infra at Section 5.3.

5. DETAILED DESCRIPTION OF THE INVENTION

A large group of protein tyrosine phosphatases have structural characteristics suggesting that they function as cell surface receptors. Receptor type tyrosine phosphatase β (RPTPβ) is expressed in the developing nervous system and it contains a carbonic anhydrase (CAH) domain as well as a fibronectin type III (FNIII) repeat in its extracellular domain. A variety of experiments were conducted to search for ligands of RPTPβ. These experiments led to the surprising recognition that the CAH domain of RPTPβ is a functional ligand for contactin, a GPI-membrane anchored neuronal cell recognition molecule that functions as a receptor on neurons. The CAH domain of RPTPβ (RPTPβ-CAH) induces cell adhesion and neurite growth of primary tectal neurons, and differentiation of neuroblastoma cells. Further experiments led to the recognition that the interaction between p190 and contactin is important in mediating the effects of contactin and RPTPβ-CAH. The assays of the invention identify compounds that mimic, enhance, or inhibit the p190 mediated effects of contactin/RPTPβ-CAH on neural cells including, but not limited to, agonists and antagonists of contactin/RPTPβ-CAH. Therapeutic uses of compounds so identified are also provided. The invention is described in detail in the following subsections and examples for purposes of clarity and not by way of limitation.

5.1. BIOLOGY OF THE INTERACTION BETWEEN CONTACTIN AND THE CAN DOMAIN OF RPTPβ

During development of the nervous systems, neurons are guided by secreted and cell bound molecules that provide both negative and positive cues. The experiments described in the examples of Sections 6.1 and 6.2 show that RPTPβ, a receptor type protein tyrosine phosphatase, may provide such a signal by interacting with the axonal recognition molecule contactin. RPTPβ is a developmentally regulated protein that exists in three forms, one secreted and two membrane bound. The extracellular region of RPTPβ has a multidomain structure consisting of a CAH-like domain, a single FNIII repeat, and a long cysteine free spacer region. The complex structural nature of its extracellular region may result in a multifunctional protein that is able to interact with different proteins. As documented by the data shown herein, the CAH and the FNIII domains bind to at least two potential ligands present on neurons or glial cells. Functional expression cloning in COS7 cells and affinity purification with a specific affinity matrix followed by microsequencing enabled unequivocal identification of the cell recognition molecule contactin (F3/F11) as a neuronal ligand of RPTPβ. The interaction between contactin and RPTPβ is mediated via the CAH domain of the phosphatase, while the FNIII domain appears to bind to another molecule expressed on the surface of glial cells. It was previously shown that the secreted proteoglycan form of RPTPβ interacts with tenascin, N-CAM and Ng-CAM (Grumet et al., 1994, J. Biol. Chem., 269:12142–12146; Barnea et al., 1994, J. Biol. Chem., 269:14349–14352; Grumet et al., 1993, J. Cell. Biol., 120:815–724; Milev et al., 1994, J. Cell. Biol., 127:1703–1715). Since N-CAM and Ng-CAM do not bind directly to the CAH or the FNIII domain of RPTPβ, they may interact with the large spacer domain of the phosphatase. Alternatively, they could interact with RPTPβ through a third component. Contactin may fulfill this function since it has been shown to interact with Ng-CAM, Nr-CAM, and the matrix proteins tenascin and restriction (Brümmendorf et al., 1993, Neuron, 10:711–727; Morales et al., 1993, Neuron, 11:1113–1122; Zisch et al., 1992, J. Cell Biol., 119:203–213). The various subdomains of the extracellular region of RPTPβ are able to interact with several distinct proteins that are expressed on diverse cell types in the central nervous system.

In contrast to other cell recognition molecules that are widely expressed in the nervous system, members of the contactin subgroup appear to be expressed in a restricted manner on specific axons during development (Dodd et al., 1988, Neuron, 1:105–116; Faivre-Sarrailh et al., 1992, J. Neurosci., 12:257–267). The spatial and temporal expression pattern of these proteins indicates they play an important role during development of the nervous system. Contactin was found to be exclusively expressed on neurons during development in fiber-rich areas of the retina, tectum, spinal cord and cerebellum (Ranscht, 1988, J. Cell. Biol, 107:1561–1573). It was found to be localized in the postnatal and adult mouse cerebellum in axonal extensions of the granule cells in the parallel layer (Faivre-Sarrailh et al., 1992, J. Neurosci., 12:257–267). This pattern of expression is overlapping with the expression pattern of RPTPβ in the rat. RPTPβ was shown to be expressed in fiber-rich regions such as the parallel fibers of the cerebellum and the spinal cord (Canoll et al., 1993, Dev. Brain Res., 75:293–298; Milev et al., 1994, J. Cell. Biol., 127:1703–1715). RPTPβ is also expressed on glial and radial glial cells, and its secreted form is produced by astrocytes. Therefore, both forms of RPTPβ may modulate neuronal function via interactions with contactin.

The contactin subgroup of glycoproteins all share structural similarity in that they are, glycosyl-phosphatidylinositol (GPI)-anchored proteins. They also exist in soluble forms generated as a result of membrane release or by expression of alternative spliced forms (Brümmendorf and Rathjen, 1993, J. Neurochem., 61:1207–1219). Differential expression of the membrane-bound and soluble forms of contactin was found in the hypothalamus-hypophyseal system (Rougon et al., 1994, Braz. J. Med. Biol. Res., 2:409–414). RPTPβ also exists in either membrane bound or secreted forms that are developmentally regulated. Therefore, both RPTPβ and contactin may act as either a ligand or a receptor for each other. Hence, the classical notion of ligand receptor interaction does not fully explain this system since both components might switch roles at different stages of development. For example, the soluble form of RPTPβ produced by glial cells may act as a ligand for the membrane bound form of contactin expressed on the surface of neuronal cells. Conversely, the soluble form of contactin may act as ligand for the membrane bound form of RPTPβ expressed on the surface of glial cells. Moreover, interaction between the membrane bound forms of contactin expressed on the surface of neurons with the membrane form of RPTPβ expressed on the surface of glial cells may lead to bidirectional signals between these two cell types. Such complex interactions between the various forms of RPTPβ and contactin may generate developmentally regulated unidirectional and bidirectional signals.

While not being limited to any theory or explanation of how the invention works, the following is hypothesized to explain how the CAH domain of RPTBβ binds to contactin. Carbonic anhydrases are highly efficient enzymes that catalyze the hydration of $CO_2$. Yet, the CAH domain of PTPases were not thought to be endowed with enzymatic activity due to substitution of two of the three key histidine residues that are essential for enzymatic activity (Barnea et al., 1993, Mol. Cell. Biol., 13:1497–1506). In contradistinction, the highly packed hydrophobic core as well as the hydrophobic residues that are exposed on the surface of carbonic anhydrase structure and which are conserved in the CAH domains of RPTPγ and β may be involved in protein-protein interaction and thus function as a ligand binding domain (Barnea et al., 1993, Mol. Cell. Biol., 13:1497–1506). It is of note that Vaccinia virus contains a transmembrane protein with a CAH-like domain in its extracellular domain, which was thought to be involved in binding of the virion to host proteins (Maa et al., 1990, J. Biol. Chem., 265: 1669–1577). Therefore, in theory but not by way of limitation, compounds exhibiting effects which mimic, enhance, or inhibit the contactin mediated effects of RPTPβ-CAH on neuronal cells may do so via other members of the contactin family of glycoproteins, and may do so even if lacking in CAH activity.

A number of models may be proposed for how contactin, a GPI-linked protein that is inserted into the outer leaflet of the plasma membrane, transmits a signal into the cells to promote neurite outgrowth. In theory, and not by way of limitation, one possibility is that contactin is able to interact with a transmembrane signaling component. The p190 (also referred to as p180) protein that was coprecipitated with contactin has been a candidate for such a signaling protein. p190 may be membrane-associated since it may not be released by phospholipase C treatment. Another potential signal transducer may be L1/Ng-CAM or a related molecule. This transmembrane CAM was shown to interact with contactin (Brümmendorf et al., 1993, Neuron, 10:711–727), and to initiate second messenger cascade via its cytoplasmic domain (Doherty and Walsh, 1994, Curr. Opin. Neurobiol., 4:49–55). The best characterized GPI linked signaling protein is the ciliary neurotrophic factor receptor (CNTF receptor). Following ligand binding, the CNTFR interacts with the signal transducer gp130. The gp130 protein that is shared by several lymphokines and cytokines such as IL-6, LIF and Oncostatin, undergoes dimerization followed by recruitment of the cytoplasmic Jak protein tyrosine kinases. Stimulation of the Jak kinases leads to activation of both the Ras/MAP kinase and the Stat signaling pathways that relay signals from the cell surface to the nucleus. A contactin associated protein such as p190 may have a function similar to the function of gp130.

As demonstrated by the examples infra, the binding of the CAH domain of RPTPβ to contactin leads to cell adhesion and neurite outgrowth. It seems unlikely that the induction of neurite growth is a default response resulting from cell adhesion per se. Neurons were found to adhere to extracellular matrix proteins such as tenascin and restriction in short term binding assays, but these substrates did not promote further neurite extension (Schachner et al., 1994, Perspect. Dev. Neurobiol., 1:33–41). It was recently reported that the FNIII domain of contactin is responsible for adhesion, while the neurite promoting activity was attributed to the Ig domains (Durbec et al., 1994, Eur. J. Neuro., 6:461–472). Another study demonstrated that contactin can mediate the repulsion of neurons by restriction (Pesheva et al., 1993, Neuron, 10:69–82). Again, this effect was proposed to occur in a stepwise manner, first an adhesion step that was followed by a signal that was transduced to the cells leading to retraction. Therefore, in light of the results presented herein, it may be that in response to different stimuli, the same molecule can transmit opposite signals depending on the context or milieu. Whatever the mechanism, the results presented here demonstrate that a receptor type tyrosine phosphatase serves as a functional ligand for a GPI-anchored cell adhesion molecule.

Contactin may also serve as a functional ligand for RPTPβ. Modulation of phosphatase activity by neuronal contactin may result in signaling to glial cells. If this does occur, this kind of bidirectional flow of information should allow the interacting cells to respond quickly to local environmental changes during development. Two other receptor type tyrosine phosphatases RPTPμ and RPTPκ were shown to mediate cell-cell interaction in a hemophilic manner (Brady-Kalany et al., 1993, J. Cell. Biol., 122:961–972; Gebbink et al., 1993, J. Biol. Chem., 268:16101–16104; Sap et al., 1994, Mol. Cell. Biol., 14:1–9). However, changes in catalytic activity as a result of these interactions could not be detected. These phosphatases are joining a growing family of proteins that are involved in cellular recognition that contain intrinsic enzymatic activities, including kinases (Dtrk; Pulido et al., 1992), EMBO J., 11:391–404, β subunit of $Na^+$, $K^+$-ATPase (AMOG; Gloor et al., 1990, J. Cell. Biol., 109:755–788), and β subunit of prolyl 4-hydroxylase (cognin; Rao and Hausman, 1993, Proc. Natl. Acad. Sci. USA, 90:2950–2954).

In summary, the experiments and data described herein demonstrate that RPTPβ is a functional ligand for the GPI-anchored cell recognition molecule contactin. The interactions between these two proteins is mediated by the CAH domain of the phosphatase. In addition, the FNIII of RPTPβ repeat is required for interaction with glia cells, demonstrating that the multidomain structure of RPTPβ enables interactions with different proteins, and indicates that other potential ligands may modulate these interactions.

5.2 BIOLOGY OF THE p190 INTERACTION

Applicants have discovered that contactin functionally interacts with p190, a novel mammalian protein described herein. In light of this information, p190 may play an important role as the link between contactin mediated neurite growth, differentiation and survival and the intracellular second messenger signalling responsible for this contactin mediated effect.

Cell recognition molecules that contain immunoglobulin (Ig)-like domains and fibronectin type III repeats (FNIII) mediate the interaction of neurons with their local environment during development (Edelman et al., 1991, Annu. Rev. Biochem., 60:155–190; Rathjen et al., 1991, Semin. Neurosci., 3:297–307; Sonderegger et al., 1991, J. Cell. Biol., 119:1387–1394). Based on structural similarity they are subdivided to three groups. The first is represented by NCAM that exist in several alternatively spliced forms (Cunningham et al., 1987, Science, 236:799–805). The second is the L1/Ng-CAM subgroup that also contains Nr-CAM and Neurofascin (Grumet, 1992, J. Neurosci. Res., 31:1–13). The third group contains contactin and its mouse and chicken homologues F3 and F11 (Ranscht, 1988, J. Cell. Biol., 107:1561–1573; Brummendorf et al., 1989, Neuron, 2:1351–1361; Gennarini et al., 1989, J. Cell. Biol., 109:755–788; Reid et al., 1994, Brain Res. Mol. Brain Res., 21:1–8; Berglund et al., 1994, Genomics, 21:571–582), TAG-1 and its chick and human homologues Axonin 1 and TAX-1 (Furley et al., 1990, Cell 61:157–170; Hasler et al., 1993, Eur. J. Biochem., 211:329–339; Zuellig et al., 1992, Eur. J. Biochem., 204:453–463) and BIG-1 (Yoshihara et al., 1994, Neuron, 13:415–426).

The glycoproteins from the contactin subgroup are all glycosylphosphatydylinositol (GPI)-anchored proteins composed of six C2 type Ig-like domains and four fibronectin type III repeats. They can also be found as secreted proteins as a result of membrane release and shedding or by alternative splicing that generate soluble forms (Brümmendorf et al., 1993, J. Neurochem., 61:1207–1219). In contrast to other cell recognition molecules that are widely expressed in the nervous system, members of the contactin subgroup are expressed in a more restricted manner on specific axons during development (Dodd et al., 1985, Neuron, 1:105–116; Faivre-Sarrailh et al., 1992, J. Neurosci., 12:257–267; Yoshihara et al., 1994, Neuron, 13:415–426). This spatial and temporal expression pattern suggests that they play a key role during axonal guidance and synapse formation.

Contactin interacts with other members of the Ig superfamily and with extracellular matrix components. Direct interaction was demonstrated between contactin and NgCAM and NrCAM, the extracellular matrix proteins tenascin and restrictin and with the carbonic anhydrase domain of the receptor type tyrosine phosphatase β (RPTPβ) (Brümmendorf et al, 1993, Neuron, 10:711–727; Zisch et al., 1992, J. Cell. Biol., 119:203–213; Zisch et al., 1992, J. Mol. Neurosci.; Pesheva et al., 1993, Neuron, 10:69–82; Peles et al., 1995, Cell, 82:251–260). These interactions are mediated by different Ig-like domains, the first and second domains bind to tenascin and Ng-CAM while the second and third mediate its interaction with restrictin (Zisch et al., 1992, J. Cell. Biol., 119:203–213; Zisch et al., 1992, J. Mol. Neurosci.; Brümmendorf et al, 1993, Neuron, 10:711–727. ). Moreover, contactin has been shown to be involved in both positive and negative responses of neurons to various stimuli (Peles et al., 1995, Cell, 82:251–260; Pesheva et al., 1993, Neuron, 10:69–82). When presented as a ligand to neurons, either as a membrane-bound or a soluble form, contactin induces axonal growth (Clarke et al., 1993, Eur. J. Cell. Biol., 61:108–115; Durbec et al., 1992, J. Cell. Biol., 117:877–887; Gennarini et al., 1989, J. Cell. Biol., 109:755–788). Its neuronal receptor has been identified as the recognition molecule Nr-CAM (Morales et al., 1993, Neuron, 11:1113–1122). Contactin itself functions as a receptor present on neurons. It mediates their repulsion by the extracellular matrix protein restrictin and neurite outgrowth induced by the CAH domain of RPTPβ (Pesheva et al., 1993, Neuron, 10:69–82; Peles et al., 1995, Cell, 82:251–260). Thus, depending on the cellular context and ligand, contactin can mediate two opposite cellular responses (e.g. repulsion vs. adhesion and outgrowth).

The function of cell recognition molecules involves two stages, first an adhesion step and then a signal transduction step. Signaling by these molecules has been shown to utilize different second messenger systems including GTP-binding proteins, calcium influx and tyrosine kinases (Reviewed in Doherty et al., 1994, Curr. Opin. Neurobiol., 4:49–55). Non-receptor tyrosine kinases of the src family connect different external signals with intracellular signaling pathways. They are highly expressed in developing neurons and are enriched in the nerve growth cones (Bare et al., 1993, Oncogene, 8:1429–1436; Maness et al., 1994, J. Biol. Chem., 193:5001–5005; Sudol et al., 1988, Oncogene Res., 2:345–355. ). There is increasing evidence that links these kinases to signaling pathways that are utilized by neural cell recognition molecules. Recently, the potential role for Src and Fyn kinases as a downstream component in L1 and N-CAM signaling was demonstrated using cerebellar neurons from src and fyn-knockout mice (Beggs et al., 1993, J. Cell Biol. 127:825–833; Ignelzi et al., 1994, Neuron, 12:873–884). In addition, activation of Fyn by the cell adhesion molecule MAG in oligodendrocytes was implicated as a regulatory signaling event during myelination (Umemori et al., 1994, Nature, 367:572–576). Finally, Fyn has been shown to associate with contactin in mouse cerebellum and in chick neurons in culture (Olive et al., 1995, J. Neurochem., 65; Zisch et al., 1992, J. Cell. Biol., 119:203–213; Zisch et al., 1992, J. Mol. Neurosci.

The method by which contactin, a GPI-linked protein, associates with a cytoplasmic kinases is unclear. One possibility is that contactin interacts with a transmembrane protein that acts as a "bridge" to the cell interior.

The experiments described herein by the Examples of Section 8 describe the cloning of such candidate molecules termed CASPR/p190 (for Contactin ASsociated PRotein). These 190 kDa proteins are found in a complex with contactin and the CAH domain of RPTPβ, but only when both p190 and RPTPβ are present on the same surface of the membrane. The cytoplasmic tail of CASPR/p190 contains a proline rich sequence that interacts with the SH3 domain of Src family kinases. Therefore this molecule could be a potential bridge that couples contactin, a GPI-linked protein, with intracellular second messenger systems.

5.3 MAMMALIAN p190 GENES AND GENE PRODUCTS

The present invention includes, but is not limited to CASPR/p190 peptides, polypeptides, polypeptide fragments and fusion proteins as described herein. The present invention further includes CASPR/p190 nucleic acid molecules are described herein.

In one embodiment, such CASPR/p190 genes and gene products are mammalian, preferably human or rodent, genes and gene products. In another embodiment, such genes and gene products are naturally occurring genes and gene products.

The purification and sequencing of p190 protein and the cloning of mammalian p190 cDNA may be conducted as described for human and rat p190 CDNA in the Examples of Section 8.

The human and rat CASPR/p190 transcripts have open reading frames that encode for 1384 and 1381 amino acids, respectively, and share 93% identity at the amino acid level. CASPR/p190 is a putative type I transmembrane protein with a short proline-rich cytoplasmic domain. (The transmembrane domain is marked as TMD in FIGS. 1A and 1B).

A description of the CASPR/p190 gene product follows. Such CASPR/p190 gene products include, but are not limited to gene products containing the amino acid sequence depicted in SEQ ID NOS:2 or 4, or the amino acid sequence of at least one of the domains depicted in SEQ ID NOS:2 or 4 and/or as depicted in FIGS. 1A and 1B and/or as described below.

The first CASPR/p190 methionine is followed by a stretch of 19–20 amino acid residues rich in hydrophobic residues, which probably acts as a signal sequence. The extracellular domains of rat and human CASPR/p190 contain 1281 and 1282 amino acid residues, respectively. The extracellular region of CASPR/p190 contains 16 potential N-linked glycosylation sites followed by a second hydrophobic stretch that is a typical transmembrane domain.

The CASPR/p190 extracellular domain is a novel mosaic of several motifs that to mediate protein-protein interactions. Near the N-terminus of mature CASPR/p190 (109 amino acid residues) is a domain with 31–33% amino acid identity to the C1 and C2 terminal domains of coagulation factors V and VIII, 26% identity with the neuronal adhesion molecule neurophilin (previously known as the neuronal A5 antigen) and 20% identity to a region of discoidin I, a lectin from the slime mold Dictyostelium discoideum. The domain is marked as DISC in FIGS. 1A and 1B.

The extracellular domain of CASPR/p190 also contains four repeats, of approximately 140 amino acid residues each, with homology to neurexins, a family of polymorphic neuronal. cell surface proteins. These domains are marked as NX1–NX4 in FIGS. 1A and 1B.

CASPR/p190 also contains two epidermal growth factor (EGF)-like modules (marked as EGF1–EGF2 in FIGS. 1A and 1B).

A single domain related to the C-terminal region of fibrinogen beta/gamma (marked as FIB in FIGS. 1A and 1B) is flanked by an EGF and neurexin motif.

CASPR/p190 contains a stretch of 47 amino acids that is identical between human and rat CASPR/p190, and contains seven copies of Pro-Gly-Tyr-$X_{1-2}$ and three additional imperfect repeats of this sequence (marked as PGY in FIGS. 1A and 1B).

The cytoplasmic domain of human and rat CASPR/p190 contain 78 and 74 amino acids, respectively. These include a 38–42 amino acid proline-rich motif (38% proline), the majority of which consists of proline residues alternating with alanine, glycine, or threonine residues (marked as PRO in FIGS. 1A and 1B).

In addition to full length CASPR/p190 gene products, CASPR/p190 polypeptide fragments are also included within the scope of the invention. In this sense, the term "CASPR/p190 polypeptide fragments" encompasses polypeptides that comprise p190 fragments, deletions, including internal deletions or any combination of p190 fragments or deletions. In particular, p190 polypeptides are those that specifically include or lack any of the domains listed in Table 2, below, or any combination thereof.

TABLE 2

| DOMAIN NAME | CASPR/p190 AMINO ACID RESIDUES AS SHOWN IN FIG. 1 AND IN SEQ ID NOS: 7 or 28 |
|---|---|
| DISC | 40–168 (SEQ ID NO:7) |
|  | 41–169 (SEQ ID NO:18) |
| NX1 | 199–330 (SEQ ID NO:8) |
|  | 200–331 (SEQ ID NO:19) |
| NX2 | 362–486 (SEQ ID NO:9) |
|  | 363–487 (SEQ ID NO:20) |
| EGF1 | 544–576 (SEQ ID NO:10) |
|  | 544–577 (SEQ ID NO:21) |
| FIB | 582–739 (SEQ ID NO:11) |
|  | 583–740 (SEQ ID NO:22) |
| NX3 | 809–938 (SEQ ID NO:12) |
|  | 810–939 (SEQ ID NO:23) |
| EGF2 | 961–985 (SEQ ID NO:13) |
|  | 962–986 (SEQ ID NO:24) |
| PGY | 1031–1077 (SEQ ID NO:14) |
|  | 1032–1078 (SEQ ID NO:25) |
| NX4 | 1083–1218 (SEQ ID NO:15) |
|  | 1084–1219 (SEQ ID NO:26) |
| TMD | 1282–1306 (SEQ ID NO:16) |
|  | 1283–1307 (SEQ ID NO:27) |
| PRO | 1328–1369 (SEQ ID NO:17) |
|  | 1329–1366 (SEQ ID NO:28) |

In a further embodiment of the invention, the p190 DNA or a modified sequence thereof may be ligated to a heterologous sequence to encode a CASPR/p190 fusion protein. For example, for screening peptide libraries it may be useful to encode a chimeric p190 protein expressing a heterologous epitope that is recognized by a commercially available antibody. A fusion protein may also be engineered to contain a cleavage site located between the p190 sequence and the heterologous protein sequence, so that the p190 protein or protein fragment can be cleaved away from the heterologous moiety. In another embodiment, DNA sequences encoding a fusion protein comprising all or a portion of the p190 protein fused to another protein with a desired activity are within the scope of the invention; e.g., enzymes such as GUS (β-glucuronidase), β-galactosidase, luciferase, etc.

With respect to nucleic acid molecules, the invention contemplates nucleic acid molecules containing: 1) any DNA sequence that encodes the same amino acid sequence as encoded by the DNA sequences shown in SEQ ID NOS:1, 3, 5 or 6; 2) any DNA sequence that hybridize to the complement of the coding sequences disclosed herein under highly stringent conditions, e.g., washing in 0.1×SSC/0.1%

SDS at 68° C. (Ausubel, et al., eds., 1989, Current Protocols in Molecular Biology, Vol. I, Green Publishing Associates, Inc., and John Wiley & sons, Inc., New York, at p. 2.10.3; see also Sambrook, J. et al., (1989) Molecular cloning, Colo. Spring Harbor Press, USA, pp. 9.47–9.55), and which can encode a functionally equivalent gene product; and/or 3) any DNA sequence that hybridizes to the complement of the coding sequences disclosed therein under less stringent conditions, such as moderately stringent conditions, e.g., washing in 0.2×SSC/0.1% SDS at 42° C. (Ausubel, et al., 1989, supra; Sambrook, et al., 1989, supra), yet which encodes a functionally equivalent gene product.

As used herein, the term "functionally equivalent gene product" refers to a gene product that exhibits at least one of the biological functions of the gene product depicted in SEQ ID NOS: 2 and/or 4. Such biological functions can include, but are not limited to, a function (e.g., a protein-protein interaction function) as exhibited by at least one of the domains of the SEQ ID NO:2 or 4 gene products.

In another embodiment, DNAs that encode mutant forms of p190 are also included within the scope of the invention. Such mutant p190 DNA sequences encompass deletions, additions and/or substitutions of nucleotide residues, or of regions coding for domains within the p190 protein. These mutated p190 DNAs may encode gene products that are functionally equivalent or which display properties very different from the native forms of p190.

The invention also encompasses 1) DNA vectors that contain any of the coding sequences disclosed herein (see SEQ ID NO:1 and SEQ ID NO:3), and/or their complements (i.e., antisense); 2) DNA expression vectors that contain any of the coding sequences disclosed therein, and/or their complements (i.e., antisense), operatively associated with a regulatory element that directs the expression of the coding and/or antisense sequences; and 3) genetically engineered host cells that contain any of the coding sequences disclosed therein, and/or their complements (i.e., antisense), operatively associated with a regulatory element that directs the expression of the coding and/or antisense sequences in the host cell. Regulatory element includes but is not limited to inducible and non-inducible promoters, enhancers, operators and other elements known to those skilled in the art that drive and regulate expression. The invention includes fragments of any of the DNA sequences disclosed herein.

p190 sequence can be obtained from a variety of sources including cDNA libraries. For example, appropriate cDNA libraries which are good sources of p190 can be obtained from (Clonetech (Palo Alto, Calif.), Stratagene (La Jolla, Calif.) the ATCC Repository (Rockville, Md.). In addition, cDNA libraries may be prepared from mRNA pools collected from mammalian cells which express p190 either constitutively or inducibly. By way of example but not by way of limitation, such cells include rat GH3 cells, as well as CHO, VERO, BHK, HeLa, COS, MDWCK, -293, WI38, etc. The collection of mRNA pools and construction of cDNA libraries from these cells are set forth more fully in the examples described infra.

Any of the cDNA libraries described above may be screened by hybridization or PCR using the p190 sequences described herein as oligonucleotide probes. Screening can be performed using those portions of the p190 sequence as discussed in the Examples of Section 8, infra.

In addition to cDNA libraries, partial p190 sequence can be obtained from any genomic library by library screening or from genomic DNA by PCR. Full cDNA sequences can be obtained by PCR of total RNA isolated from any cell or tissue that expresses p190 including, but not limited to, neuronal tissue. Cellular sources also include, but are not limited to, hematopoietic, fetal, and embryonal tissues.

Alternatively, the cDNA libraries described above can be used to construct expression libraries in a cell line such as CHO, VERO, BHK, HeLa, COS, MDWCK, -293, WI38, etc., or other cells known in the art to contain little or no autologous p190 activity. These expression libraries can then be screened using antibodies which are specific to p190. Expression libraries for antibody screening may also be made in bacteria, such as *E. coli*, using phage vectors, such as lambda. These expression libraries may also be screened for p190 enzyme activity as set forth in the examples which are described in more detail infra.

Other isoforms of p190 may exist and may be cloned using the p190 gene sequence.

5.4 EXPRESSING THE p190 GENE PRODUCT

In order to express a biologically active p190, the coding sequence for the enzyme, a function equivalent, or a modified sequence, as, e.g., described in Section 5.3., supra, is inserted into an appropriate eukaryotic expression vector, i.e., a vector which contains the necessary elements for transcription and translation of the inserted coding sequence in appropriate eukaryotic host cells which possess the cellular machinery and elements for the proper processing, i.e., signal cleavage, glycosylation, phosphorylation, sialylation, and protein sorting. Mammalian host cell expression systems are preferred for the expression of biologically active enzymes that are properly folded and processed. When administered in humans such expression products may also exhibit tissue targeting.

The invention also encompasses peptide fragments of the p190 gene product. The p190 gene product or peptide fragments thereof, can be linked to a heterologous peptide or protein as a fusion protein. In addition, chimeric p190 expressing a heterologous epitope that is recognized by a commercially available antibody is also included in the invention. A durable fusion protein may also be engineered; i.e., a fusion protein which has a cleavage site located between the p190 sequence and the heterologous protein sequence, so that the p190 gene product, or fragment thereof, can be cleaved away from the heterologous moiety. For example, a collagenase cleavage recognition consensus sequence may be engineered between the p190 gene product, or fragment thereof, the heterologous peptide or protein. The p190 domain can be released from this fusion protein by treatment with collagenase.

5.4.1 CONSTRUCTION OF EXPRESSION VECTORS AND PREPARATION OF TRANSFECTANTS

Methods which are well-known to those skilled in the art can be used to construct expression vectors containing the p190 coding sequence and appropriate transcriptional/translational control signals. These methods include in vitro recombination/genetic recombination. See, for example, the techniques described in Sambook et al., 1987, Molecular Cloning A Laboratory Manual, Cold Spring Harbor Laboratory, N.Y., Chapter 12.

p190 proteins produced by these methods would be useful for in vitro studies on the mechanism of action of p190 and particularly for further studies on the mechanism of action of any inhibitors that are selective for p190 that are identified by drug screening with the stably expressing p190 cell lines, as infra, or for investigating the mechanism of action of existing drugs or of inhibitors that may be identified by other means. The purified p190 proteins would also be useful for the production of crystals suitable for X-ray crystallography. Such crystals would be extremely beneficial for the rational design of drugs based on molecular structure. Expression of these chimeric DNA constructs in a baculovirus or yeast system and subsequent crystallization of the proteins would yield such data.

A variety of eukaryotic host-expression systems may be used to express the p190 coding sequence. Although prokaryotic systems offer the distinct advantage of ease of manipulation and low cost of scale-up, their major drawback in the expression of p190 is their lack of proper post-translational modifications of expressed mammalian proteins. Eukaryotic systems, and preferably mammalian expression systems, allow for proper modification to occur. Eukaryotic cells which possess the cellular machinery for proper processing of the primary transcript glycosylation, phosphorylation, and, advantageously secretion of the gene product should be used as host cells for the expression of p190. Mammalian cell lines are preferred. Such host cell lines may include but are not limited to CHO, VERO, BHK, HeLa, COS, MDWCK, -293, WI38, etc. Alternatively, eukaryotic host cells which possess some but not all of the cellular machinery required for optional processing of the primary transcript and/or post-translational processing and/or secretion of the gene product may be modified to enhance the host cell's processing capabilities. For example, a recombinant nucleotide sequence encoding a peptide product that performs a processing function the host cell had not previously been capable of performing, may be engineered into the host cell line. Such a sequence may either be co-transfected into the host cell along with the gene of interest, or included in the recombinant construct encoding the gene of interest. Alternatively, cell lines containing this sequence may be produced which are then transfected with the gene of interest.

Appropriate eukaryotic expression vectors should be utilized to direct the expression of p190 in the host cell chosen. For example, at least two basic approaches may be followed for the design of vectors based on SV40. The first is to replace the SV40 early region with the gene of interest while the second is to replace the late region (Hammarskjold, et al., 1986, Gene, 43:41–50. Early and late region replacement vectors can also be complemented in vitro by the appropriate SV40 mutant lacking the early or late region. Such complementation will produce recombinants which are packaged into infectious capsids and which contain the p190 gene. A permissive cell line can then be infected to produce the recombinant protein. SV40-based vectors can also be used in transient expression studies, where best results are obtained when they are introduced into COS (CV-1, origin of SV40) cells, a derivative of CV-1 (green monkey kidney cells) which contain a single copy of an origin defective SV40 genome integrated into the chromosome. These cells actively synthesize large T antigen (SV40), thus initiating replication from any plasmid containing an SV40 origin of replication.

In addition to SV40, almost every molecularly cloned virus or retrovirus may be used as a cloning or expression vehicle. Viral vectors based on a number of retroviruses (avian and murine), adenoviruses, vaccinia virus (Cochran, et al., 1985, Proc. Natl. Acad. Sci. USA, 82:19–23) and polyoma virus may be used for expression. Other cloned viruses, such as J C (Howley, et al., 1980, J. Virol. 36:878–882), BK and the human papilloma viruses (Heilmsan, et al., 1980, J. Virol, 36:395–407), offer the potential of being used as eukaryotic expression vectors. For example, when using adenovirus expression vectors, the p190 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the human enzyme in infected hosts (e.g., see Logan & Shenk, 1984, Proc. Natl. Acad. Sci. USA, 81:3655–3659). Alternatively, the vaccinia virus 7.5K promoter may be used. (e.g., see, Hackett et al., 1982, Proc. Natl. Acad. Sci. USA, 79:7415–7419; Hackett et al., 1994, J. Virol. 49:857–864, Panicali et al., 1982, Proc. Natl. Acad. Sci. USA, 79:4927–4931). Of particular interest are vectors based on bovine papilloma virus (Sarver, et al., 1981, Mol. Cell. Biol., 1:486–496), or Semliki Forest Virus, which provides large quantities of active protein in induced cells (Olkkohnen et al., 1994, Meth. Cell. Biol., 43 part A:43–53; Lundstrum et al., 1994, Eur. J. Biochem., 224:917–921). These vectors have the ability to replicate as extrachromosomal elements. Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. High level expression may also be achieved using inducible promoters such as the metallothionine IIA promoter, heat shock promoters, etc.

For long-term, high-yield production of recombinant proteins, stable expression is preferred. For example, following the introduction of foreign DNA, engineered cells may be allowed to grow for 1–2 days an enriched media, and then are switched to a selective media. Rather than using expression vectors which contain viral origins of replication, host cells can be transformed with the p190 DNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. A number of selection systems may be used, including but not limited to the herpes simplex virus thymidine kinase (Wigler, et al., 1977, Cell, 11:223–232), hypoxanthine-guanine phosphoribosylatransferase (Szybalska & Szybalski, 1962, Proc. Natl. Acad. Sci. USA, 48:2026), and adenine phosphoribosyltransferase (Lowy, et al., 1980, Cell, 22:817–823) genes can be employed in tk$^-$, hgprt$^-$ or aprt$^-$ cells respectively. Also, antimetabolite resistance can be used as the basis of selection for dhfr, which confers resistance to methotrexate (Wigler, et al., 1980, Natl. Acad. Sci. USA 77:3567–3570; O'Hare, et al., 1981, Proc. Natl. Acad. Sci. USA 78:1527–1531); ygpt, which confers resistance to mycophenolic acid (Mulligan & Berg, 1981, Proc. Natl. Acad. Sci. USA, 78:2072–2076); neo, which confers resistance to the aminoglycoside G-418 (Colberre-Garapin, et al., 1981, J. Mol.

Biol., 150:1–14); and hygro, which confers resistance to hygromycim (Santerre, et al., 1994, Gene, 30:147–156) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl.

Acad. Sci. USA, 85:8047–8051), and ODC (ornithine decarboxylase) which confers resistance to the ornithine decarboxylase inhibitor, 2-(difluromethyl)-DL-ornithine, DFMO (McConlogue L., 1987, In: Current Communications in Molecular Biology, Cold Spring Harbor Laboratory ed.).

Alternative eukaryotic expression systems which may be used to express the p190 enzymes are yeast transformed with recombinant yeast expression vectors containing the p190 coding sequence; insect cell system infected with recombinant virus expression vectors (e.g., baculovirus) containing the p190 coding sequence; or plant cell systems infected with recombinant virus expression vectors (e.g., cauliflower mosaic virus, CaMV; tobacco mosaic, TMV) or transformed with recombinant plasmid expression vectors (e.g., Ti plasmid) containing the p190 coding sequence.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp. 516–544; Glover, 1986, DNA Cloning, Vol. II, IRL Press, Wash., D.C., Ch. 3; Bitter, 1987, Heterologous Gene Expression in Yeast, Methods in Enzymology, Eds. Berger & Kimmel Acad. Press, N.Y., Vol. 152, pp. 673–694; and The Molecular Biology of the Yeast Saccharomyces, 1982, Eds. Strathem et al., Cold Spring Harbor Press, Vols. I and II. For complementation assays in yeast, cDNAs for p190 may be cloned into yeast episomal plasmids (YEp) which replicate autonomously in yeast due to the presence of the yeast $2\mu$ circle. The cDNA may be cloned behind either a constitutive yeast promoter such as ADH or LEU2 or an inducible promoter such as GAL (Cloning in Yeast, Chpt. 3, R. Rothstein In: DNA Cloning Vol. 11, A Practical Approach, Ed. DM Glover, 1986, IRL Press, Wash., D.C.). Constructs may contain the 5' and 3' non-translated regions of the cognate p190 mRNA or those corresponding to a yeast gene. YEp plasmids transform at high efficiency and the plasmids are extremely stable. Alternatively, vectors may be used which promote integration of foreign DNA sequences into the yeast chromosome.

Alternately, active, post-translationally modified p190 proteins can be obtained using a yeast expression system such as the *Pichia pastoris* expression system marketed by Invitrogen (*Pichia pastoris* is owned and licensed by Research Corporation Technologies, Tucson, Ariz; however, all components are available from Invitrogen, San Diego, Calif.). In this example, cDNAs encoding human p190 are independently cloned into the pHIL-D2 Pichia expression vector. After linearization with a restriction endonuclease, these constructs are transfected into spheroblasts of the his4 *Pichia pastoris* strain, GS115, and recombinant yeast carrying the cloned p190 DNA sequences are identified by screening for yeast clones that grow in the absence of histidine (now supplied by the recombinant vector), but do not efficiently utilize methanol as the sole carbon source (due to the presence of p190 in the place of AOXI gene sequence coding for methanol utilization). After expansion of such clones in the presence of an alternative carbon source such as glycerol, large quantities of cells would be transferred to liquid media containing methanol where replication ceases. However, cells remain viable for many days during which time human p190 proteins are specifically expressed at high levels under control of the AOXI promoter. The advantages of this system include very high protein yields and lower expense in the production and maintenance of cultures.

In cases where plant expression vectors are used, the expression of the p190 coding sequence may be driven by any of a number of promoters. For example, viral promoters such as the 35S RNA and 19S RNA promoters of CaMV (Brisson et al., 1984, Nature, 310:511–514), or the coat protein promoter of TMV (Takamatsu et al., 1987, EMBO J., 6:307–311) may be used; alternatively, plant promoters such as the small subunit of RUBISCO (Coruzzi et al., 1994, EMBO J., 3:1671–1680; Broglie et al., 1984, Science, 224:838–843); or heat shock promoters, eg., soybean hsp 17.5-E or hsp 17.3-B (Gurley et al., 1986, Mol. Cell. Biol., 6:559–565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9.

An alternative expression system which could be used to express p190 is an insect system. In one such system, *Autographa californica* nuclear polyhedrosis virus (AcNPV) is used as a vector to express foreign genes. The virus grows in *Spodoptera frugiperda* cells. The p190 sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded re-combinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Virol., 46:584, Smith, U.S. Pat. No. 4,215,051).

In a specific embodiment of an insect system, the DNA encoding p190 can be independently cloned into the pBlueBacIII recombinant transfer vector (Invitrogen, San Diego, Calif.) downstream of the polyhedrin promoter and transfected into Sf9 insect cells (derived from *Spodoptera frugiperda* ovarian cells, available from Invitrogen, San Diego, Calif.) to generate recombinant virus containing p190. After plaque purification of the recombinant virus high-titer viral stocks are prepared that in turn would be used to infect Sf9 or High Five™ (BTI-TN-5B1–4 cells derived from *Trichoplusia ni* egg cell homogenates; available from Invitrogen, San Diego, Calif.) insect cells, to produce large quantities of appropriately post-translationally modified p190 proteins. Although it is possible that these cells themselves could be directly useful for drug assays, the p190 proteins prepared by this method can be used for in vitro assays of drug potency and selectivity.

5.4.2 IDENTIFICATION OF TRANSFECTANTS OR TRANSFORMANTS EXPRESSING THE D190 GENE PRODUCT

The host cells which contain the p190 coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of p190 mRNA transcripts in the host cell; and (d) detection of the gene product as measured by immunoassay or by its biological activity.

In the first approach, the presence of the p190 coding sequence inserted in the expression vector can be detected by DNA-DNA or DNA-RNA hybridization or PCR using probes comprising nucleotide sequences that are homologous the p190 coding sequence or portions or derivatives thereof.

In the second approach, the recombinant expression vector/host system can be identified and selected based upon the presence or absence of certain "marker" gene functions (e.g., resistance to antibiotics, resistance to methotrexate, transformation phenotype, occlusion body formation in baculovirus, etc.). For example, if the p190 coding sequence is within a marker gene sequence of the vector, recombinants containing the p190 coding sequence can be identified by the absence of the marker gene function. Alternatively, a marker gene can be placed in tandem with the p190 sequence under the control of the same or different promoter used to control the expression of the p190 coding sequence. Expression of the marker in response to induction or selection indicates expression of the p190 coding sequence. In addition, the marker gene may be identified by DNA-DNA or DNA-RNA hybridization or PCR.

In the third approach, transcriptional activity for the p190 coding region can be assessed by hybridization or PCR assays. For example, RNA can be isolated and analyzed by Northern blot using a probe homologous to the p190 coding sequence or particular portions thereof. Alternatively, total nucleic acids of the host cell may be extracted and assayed for hybridization to such probes.

In the fourth approach, the expression of the p190 protein product can be assessed immunologically, for example by Western blots, immunoassays such as radioimmunoprecipitation, enzyme-linked immunoassays and the like. The ultimate test of the success of the expression system, however, involves the detection of the biologically active p190 gene product. Where the host cell secretes the gene product, the cell free media obtained from the cultured transfectant host cell may be assayed for p190 activity. Where the gene product is not secreted, cell lysates may be assayed for such activity. In either case, a number of assays can be used to detect p190 activity, including but not limited to, those described in the examples infra or those known in the art.

5.4.3 CELL LINES EXPRESSING p190

The present invention also relates to cell lines containing recombinant DNA sequence, preferably a chromosomally integrated recombinant DNA sequence, which comprises the gene encoding p190 which cell lines further do not express autologous p190, apart from that encoded by the recombinant DNA sequence.

A specific embodiment of the present invention is an engineered mammalian cell line which contains a chromosomally integrated, genetically-engineered ("recombinant") DNA sequence, which DNA sequence expresses mammalian p190, and wherein said cell line also does not express autologous p190. The cell line is preferably of human or primate origin, such as the exemplified monkey kidney COS cell line, but cell lines derived from other species may be employed, including chicken, hamster, murine, ovine and the like; the CHO (Chinese hamster ovary) cell line for example, may be particularly preferred for large scale production.

Any cell or cell line, the genotype of which has been altered by the presence of a recombinant DNA sequence is encompassed by the invention. The recombinant DNA sequence may also be referred to herein as "heterologous DNA," "exogenous DNA," "genetically engineered" or "foreign DNA," indicating that the DNA was introduced into the genotype or genome of the cell or cell line by a process of genetic engineering.

The invention includes, but is not limited to, a cell or cell line wherein the native p190 DNA sequence has been removed or replaced as a result of interaction with a recombinant DNA sequence. Such cells are called p190 knockouts, herein, if the resulting cell is left without a native DNA that encodes a functional p190 gene product.

As used herein, the term "recombinant DNA sequence" refers to a DNA sequence that has been derived or isolated from any source, that may be subsequently chemically altered, and later introduced into mammalian cells. An example of a recombinant DNA sequence "derived" from a source, would be a DNA sequence that is identified as a useful fragment within a given organism, and which is then chemically synthesized in essentially pure form. An example of such DNA sequence "isolated" from a source would be a DNA sequence that is excised or removed from said source by chemical means, e.g., by the use of restriction endonucleases, so that it can be further manipulated, e.g., amplified, for use in the invention, by the methodology of genetic engineering.

Therefore, "recombinant DNA sequence" includes completely synthetic DNA, semi-synthetic DNA, DNA isolated from biological sources, and DNA derived from introduced RNA. Generally, the recombinant DNA sequence is not originally resident in the genotype which is the recipient of the DNA sequence, or it is resident in the genotype but is not expressed.

The isolated recombinant DNA sequence used for transformation herein may be circular or linear, double-stranded or single-stranded. Generally, the DNA sequence is chimeric linear DNA, or is a plasmid or viral expression vector, that can also contain coding regions flanked by regulatory sequences which promote the expression of the recombinant DNA present in the resultant cell line. For example, the recombinant DNA sequence may itself comprise or consist of a promoter that is active in mammalian cells, or may utilize a promoter already present in the genotype that is the transformation target. Such promoters include, but are not limited to, the CMV promoter, SV 40 late promoter and retroviral LTRs (long terminal repeat elements).

The general methods for constructing recombinant DNA which can transform target cells are well known to those skilled in the art, and the same compositions and methods of construction may be utilized to produce the DNA useful herein. For example, J. Sambrook et al., Molecular Cloning; A Laboratory Manual, Cold Spring Harbor Laboratory Press (2d ed., 1989), provides suitable methods of construction.

Aside from recombinant DNA sequence that serve as transcription units for p190 or other portions thereof, a portion of the recombinant DNA may be untranscribed, serving a regulatory or a structural function.

The recombinant DNA sequence to be introduced into the cells further will generally contain either a selectable marker gene or a reporter gene or both to facilitate identification and selection of transformed cells. Alternatively, the selectable marker may be carried on a separate piece of DNA and used in a co-transformation procedure. Both selectable markers and reporter genes may be flanked with appropriate regulatory sequences to enable expression in mammalian cells. Useful selectable markers are well known in the art and include, for example, anti-biotic and herbicide resistance genes.

Sources of DNA sequences useful in the present invention include Poly-A RNA from mammalian cells, from which the mRNA encoding p190 can be derived and used for the synthesis of the corresponding cDNA by methods known to the art. Such sources include cDNA libraries and mRNA pools made from neuronal, neuroblastoma, embryonic, fetal, and hematopoietic tissues of human, rat or other mammalian origin.

Selectable marker genes encoding enzymes which impart resistance to biocidal compounds are listed in Table 1, below.

TABLE 3

Selectable Marker Genes

| Resistance Gene or Enzyme | Confers Resistance to: | Reference |
|---|---|---|
| Neomycin phosphotransferase (neo) | G-418, neomycin, kanamycin | Southern et al., 1982, J. Mol. Appl. Gen., 1:327–341 |
| Hygromycin phosphotransferase (hpt or hyg) | Hygromycin B | Shimizu et al., 1986, Mol. Cell Biol., 6:1074–1087 |
| Dihydrofolate reductase (dhfr) | Methotrexate | Kwok et al., 1986, Proc. Nat'l. Acad. Sci. USA, 4552–4555 |
| Phosphinothricin acetyltransferase (bar) | Phosphinothricin | DeBlock et al., 1987, EMBO J., 6:2513–2518 |
| 2,2-Dichloropropionic acid dehalogenase | 2-2,Dichloropropionic acid (Dalapon) | Buchanan-Wollaston et al., 1989, J. Cell. Biochem., Supp. 13D, 330 |
| Acetohydroxyacid synthase | Sulfonylurea, imidazolinone and triazolopyrimidine herbicides | Anderson et al. (U.S. Pat. No. 4,761,373); G. W. Haughn et al., 1988 Mol. Gen. Genet., 211:266–271 |
| 5-Enolpyruvyl-shikimatephosphate synthase (aroA) | Glyphosate | Comai et al., 1985 Nature, 317:741–744 |
| Haloarylnitrilase | Bromoxynil | Stalker et al., published PCT appln. W087/04181 |
| Acetyl-coenzyme A carboxylase | Sethoxydim, haloxyfop | Parker et al., 1990 Plant Physiol., 92:1220 |
| Dihydropteroate synthase (sul I) | Sulfonamide herbicides | Guerineau et al., 1990, Plant Molec. Biol., 15:127–136 |
| 32 kD photosystem II polypeptide (psbA) | Triazine herbicides | Hirschberg et al., 1983, Science, 222:1346–1349 |
| Anthranilate synthase | 5-Methyltryptophan | Hibberd et al. (U.S. Pat. No. 4,581,847) |
| Dihydrodipicolinic acid synthase (dap A) | Aminoethyl cysteine | Glassman et al., published PCT application No. W089/11789 |

Reporter genes are used for identifying potentially transformed cells and for evaluating the functionality of regulatory sequences. Reporter genes which encode for easily assayable marker proteins are well known in the art. In general, a reporter gene is a gene which is not present in or expressed by the recipient organism or tissue and which encodes a protein whose expression is manifested by some easily detectable property, e.g., enzymatic activity. Preferred genes includes the chloramphenicol acetyl transferase gene (cat) from Tn9 of E. coli, the beta-galactosidase gene of E. coli, the beta-glucuronidase gene (gus) of the uidA locus of E. coli, and the luciferase gene from firefly Photinus pyralis. Expression of the reporter gene is assayed at a suitable time after the DNA has been introduced into the recipient cells.

Other elements such as introns, enhancers, polyadenylation sequences and the like, may also be a part of the recombinant DNA sequence. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The recombinant DNA sequence can be readily introduced into the target cells by transfection with an expression vector, such as a viral expression vector, comprising cDNA encoding p190 by the modified calcium phosphate precipitation procedure of Chen et al., 1987, Mol. Cell. Biol., 7:2745–2752. Transfection can also be accomplished by other methods, including lipofection, using commercially available kits, e.g., provided by Life Technologies.

In a preferred embodiment of the invention, the cell lines of the invention are able to express a stable p190 gene product or analog, homologue, or deletion thereof after several passages through cell culture.

5.4.4 PURIFICATION OF THE p190 GENE PRODUCT

Once a cell that produces high levels of biologically active p190 is identified, the cell may be clonally expanded and used to produce large quantities of the enzyme, which may be purified using techniques well-known in the art including, but not limited to, immunoaffinity purification, chromatographic methods including high performance liquid chromatography and the like. Where the enzyme is secreted by the cultured cells, p190 may be readily recovered from the culture medium.

Where the p190 coding sequence, or fragment thereof, has been engineered to encode a cleavable fusion protein, the purification of the p190 gene product, or fragment thereof, may be readily accomplished using affinity purification techniques. For example, an antibody specific for the heterologous peptide or protein can be used to capture the durable fusion protein; for example, on a solid surface, a column etc. The p190 moiety can be released by treatment with the appropriate enzyme that cleaves the linkage site. cDNA construction using the polymerase chain reaction accompanied by transfection and purification of the expressed protein permits the isolation of sufficient quantities of p190 for characterization of the enzyme's physical and kinetic properties. Using site-directed mutagenesis or naturally occurring mutant sequences, this system provides a reasonable approach to determine the effects of the altered primary structure on the function of the protein. Fusion constructs of the p190 protein domain with the marker peptide preceding the amino terminus of p190 or following the carboxy terminus of p190 may also be engineered to evaluate which fusion construct will interfere the least, if at all, with the protein's biologic function and the ability to be purified.

Using this aspect of the invention, any cleavage site or enzyme cleavage substrate may be engineered between the p190 sequence and a second peptide or protein that has a binding partner which could be used for purification, e.g, any antigen for which an immunoaffinity column can be prepared.

5.5 ANTIBODIES TO THE p190 GENE PRODUCT

For the production of antibodies, various host animals may be immunized by injection with the p190 gene product, or a portion thereof including, but not limited to, portions of the p190 gene product in a recombinant protein. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum.

Monoclonal antibodies may be prepared by using any technique which provides for the production of antibody molecules by continuous cell lines in culture. These include but are not limited to the hybridoma technique originally described by Kohler and Milstein, 1975, Nature, 256:495–497, the human B-cell hybridoma technique (Kosbor et al., 1983, Immunology Today, 4:72, Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies specific to one of the binding partners.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.6 GENE THERAPIES BASED ON THE p190 GENE

A variety of gene therapy approaches may be used in accordance with the invention to modulate expression of the p190 gene in vivo. For example, antisense DNA molecules may be engineered and used to block translation of p190 mRNA in vivo. Alternatively, ribozyme molecules may be designed to cleave and destroy the p190 mRNAs in vivo. In another alternative, oligonucleotides designed to hybridize to the 5' region of the p190 gene (including the region upstream of the coding sequence) and form triple helix structures may be used to block or reduce transcription of the p190 gene. In yet another alternative, nucleic acid encoding the full length wild-type p190 message may be introduced in vivo into cells which otherwise would be unable to produce the wild-type p190 gene product in sufficient quantities or at all.

In a preferred embodiment, the antisense, ribozyme and triple helix nucleotides are designed to inhibit the translation or transcription of p190. To accomplish this, the oligonucleotides used should be designed on the basis of relevant sequences unique to p190. For example, and not by way of limitation, the oligonucleotides should not fall within those regions where the nucleotide sequence of p190 is most homologous to that of other known proteins.

Instead, it is preferred that the oligonucleotides fall within the regions of p190, which diverge from the sequence of other known proteins.

In the case of antisense molecules, it is preferred that the sequence be chosen from those divergent sequences just mentioned above. It is also preferred that the sequence be at least 18 nucleotides in length in order to achieve sufficiently strong annealing to the target mRNA sequence to prevent translation of the sequence. Izant and Weintraub, 1984, Cell, 36:1007–1015; Rosenberg et al., 1985, Nature, 313:703–706.

In the case of the "hammerhead" type of ribozymes, it is also preferred that the target sequences of the ribozymes be chosen from the above-mentioned divergent sequences. Ribozymes are RNA molecules which possess highly specific endoribonuclease activity. Hammerhead ribozymes comprise a hybridizing region which is complementary in nucleotide sequence to at least part of the target RNA, and a catalytic region which is adapted to cleave the target RNA. The hybridizing region contains nine (9) or more nucleotides. Therefore, the hammerhead ribozymes of the present invention have a hybridizing region which is complementary to the sequences listed above and is at least nine nucleotides in length. The construction and production of such ribozymes is well known in the art and is described more fully in Haseloff and Gerlach, 1988, Nature, 334:585–591.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech endoribonucleases have an eight base pair active site which hybridizes to a target RNA sequence whereafter cleavage of the target RNA takes place. The invention encompasses those Cech-type ribozymes which target eight base-pair active site sequences that are exclusive to p190.

In the case of oligonucleotides that hybridize to and form triple helix structures at the 5' terminus of the p190 gene and can be used to block transcription, it is preferred that they be complementary to those sequences in the 5' terminus of p190 which are not present in other related proteins. However, it is preferred that the sequences not include those regions of the p190 promoter which are even slightly homologous to that of other known proteins.

The foregoing compounds can be administered by a variety of methods which are known in the art including, but not limited to the use of liposomes as a delivery vehicle. Naked DNA or RNA molecules may also be used where they are in a form which is resistant to degradation such as by modification of the ends, by the formation of circular molecules, or by the use of alternate bonds including phosphothionate and thiophosphoryl modified bonds. In addition, the delivery of nucleic acid may be by facilitated transport where the nucleic acid molecules are conjugated to polylysine or transferrin. Nucleic acid may also be transported into cells by any of the various viral carriers, including but not limited to, retrovirus, vaccinia, AAV, and adenovirus.

Alternatively, a recombinant nucleic acid molecule which encodes, or is, such antisense, ribozyme, triple helix, or p190 molecule can be constructed. This nucleic acid molecule may be either RNA or DNA. If the nucleic acid encodes an RNA, it is preferred that the sequence be operatively attached to a regulatory element so that sufficient copies of the desired RNA product are produced. The regulatory element may permit either constitutive or regulated transcription of the sequence. In vivo, that is, within the cells or cells of an organism, a transfer vector such as a bacterial plasmid or viral RNA or DNA, encoding one or more of the RNAs, may be transfected into cells e.g. (Llewellyn et al., 1987, J. Mol. Biol., 195:115–123; Hanahan et al. 1983, J. Mol. Biol., 166:557–580). Once inside the cell, the transfer vector may replicate, and be transcribed by cellular polymerases to produce the RNA or it may be integrated into the genome of the host cell. Alternatively, a transfer vector containing sequences encoding one or more of the RNAs may be transfected into cells or introduced into cells by way of micromanipulation techniques such as microinjection, such that the transfer vector or a part thereof becomes integrated into the genome of the host cell.

5.7 DRUG SCREENING ASSAYS

The present invention provides a simple in vitro system for the screening of drug actions on p190, which will be useful for the development of drugs that modulate the growth, differentiation or survival of neurons. Assays can be performed on living mammalian cells, which more closely approximate the effects of a particular serum level of drug in the body, or on microsomal extracts prepared from the cultured cell lines. Studies using microsomal extracts offer the possibility of a more rigorous determination of direct drug/enzyme interactions.

The p190-synthesizing cell lines are useful for evaluating the activity of potential bioactive agents on p190.

The present invention also provides a second mammalian cell line which contains a chromosomally integrated, recombinant DNA sequence, wherein said DNA sequence expresses; mammalian, p190, and wherein said cell line also preferably does not express autologous p190 activity. This second cell line is also preferably a primate, murine or human cell line.

Thus, the present invention also provides a method to evaluate.

The invention also relates to methods for the identification of genes, termed "pathway genes", which are associated with the p190 gene product or with the biochemical pathways which extend therefrom. "Pathway gene", as used herein, refers to a gene whose gene product exhibits the ability to interact with the p190 gene product.

Any method suitable for detecting protein-protein interactions may be employed for identifying pathway gene products by identifying interactions between gene products and the p190 gene product. Such known gene products may be cellular or extracellular proteins. Those gene products which interact with such known gene products represent pathway gene products and the genes which encode them represent pathway genes.

Among the traditional methods which may be employed are co-immunoprecipitation, crosslinking and co-purification through gradients or chromatographic columns. Utilizing procedures such as these allows for the identification of pathway gene products. Once identified, a pathway gene product may be used, in conjunction with standard techniques, to identify its corresponding pathway gene. For example, at least a portion of the amino acid sequence of the pathway gene product may be ascertained using techniques well known to those of skill in the art, such as via the Edman degradation technique (see, e.g., Creighton, 1983, Proteins: Structures and Molecular Principles, W. H. Freeman & Co., N.Y., pp.34–49). The amino acid sequence obtained may be used as a guide for the generation of oligonucleotide mixtures that can be used to screen for pathway gene sequences. Screening made be accomplished, for example by standard hybridization or PCR techniques. Techniques for the generation of oligonucleotide mixtures and screening are well-known. (See, e.g., Ausubel et al., eds., 1987–1993, Current Protocols in Molecular Biology, John Wiley & Sons, Inc. New York, and PCR Protocols: A Guide to Methods and Applications, 1990, Innis, M. et al., eds. Academic Press, Inc., New York).

Additionally, methods may be employed which result in the simultaneous identification of pathway genes which encode the protein interacting with the p190 gene product. These methods include, for example, probing expression libraries with labeled protein known or suggested to be involved in cardiovascular disease, using this protein in a manner similar to the well known technique of antibody probing of λgt11 libraries.

One such method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to a known protein, and the other consists of the activator protein's activation domain fused to an unknown protein that is encoded by a cDNA which has been recombined into this plasmid as part of a cDNA library. The plasmids are transformed into a strain of the yeast Saccharomyces cerevisiae that contains a reporter gene (e.g., lacZ) whose regulatory region contains the activator's binding sites. Either hybrid protein alone cannot activate transcription of the reporter gene: the DNA-binding domain hybrid because it does not provide activation function and the activation domain hybrid because it cannot localize to the activator's binding sites. Interaction of the two proteins reconstitutes the functional activator protein and results in expression of the reporter gene, which is detected by an assay for the reporter gene product.

The two-hybrid system or related methodology may be used to screen activation domain libraries for proteins that interact with the p190 gene product, herein also called the known "bait" gene protein. Total genomic or cDNA sequences may be fused to the DNA encoding an activation domain. Such a library and a plasmid encoding a hybrid of the bait gene protein fused to the DNA-binding domain may be cotransformed into a yeast reporter strain, and the resulting transformants may be screened for those that express the reporter gene. These colonies may be purified and the library plasmids responsible for reporter gene expression may be isolated. DNA sequencing may then be used to identify the proteins encoded by the library plasmids.

For example, and not by way of limitation, the bait gene may be cloned into a vector such that it is translationally fused to the DNA encoding the DNA-binding domain of the GAL4 protein.

A cDNA library of the cell line from which proteins that interact with bait gene are to be detected can be made using methods routinely practiced in the art. According to the particular system described herein, for example, the cDNA fragments may be inserted into a vector such that they are translationally fused to the activation domain of GAL4. This library may be co-transformed along with the bait gene-GAL4 fusion plasmid into a yeast strain which contains a lacZ gene driven by a promoter which contains the GAL4 activation sequence. A cDNA encoded protein, fused to the GAL4 activation domain, that interacts with bait gene will reconstitute an active GAL4 protein and thereby drive expression of the lacZ gene. Colonies which express lacZ may be detected by their blue color in the presence of X-gal. The cDNA may then be purified from these strains, and used to produce and isolate the bait gene-interacting protein using techniques routinely practiced in the art.

Once a pathway gene has been identified and isolated, it may be further characterized as, for example, discussed herein.

The proteins identified as products of pathway genes may be used to modulate p190 gene expression, as defined herein, or may themselves be targets for modulation to in turn modulate symptoms associated with p190 expression.

5.8 COMPOUNDS IDENTIFIED IN THE SCREENS

The compounds identified in the screen will demonstrate the ability to selectively modulate the expression of p190. These compounds include but are not limited to nucleic acid encoding p190 and homologues, analogues, and deletions thereof, as well as antisense, ribozyme, triple helix, antibody, and polypeptide molecules and small inorganic molecules.

5.9 PHARMACEUTICAL FORMULATIONS AND ROUTES OF ADMINISTRATION

Any of the identified compounds can be administered to an animal host, including a human patient, by itself, or in pharmaceutical compositions where it is mixed with suitable carriers or excipient(s) at doses therapeutically effective to treat or ameliorate a variety of disorders, including those characterized by insufficient, aberrant, or excessive p190 activity or neurite growth, differentiation or survival, including but not limited to: ALS; general ataxia; Parkinson's disease; Alzheimer's disease; Huntington's disease; general neuropathy; cerebral palsy; neurologic trauma; and mental retardation. A therapeutically effective dose further refers to that amount of the compound sufficient to result in amelioration of symptoms associated with such disorders. Techniques for formulation and administration of the compounds of the instant application may be found in "Remington's Pharmaceutical Sciences," Mack Publishing Co., Easton, Pa., latest edition.

A number of disorders may be characterized by insufficient, aberrant, or excessive p190 activity. In addition, several physiological states which may, from time to time be considered undesired, may also be associated with p190 activity. By way of example, but not by way of limitation, such disorders and physiological states which may be treated with the compounds of the invention include but are not limited to those characterized by insufficient, aberrant, or excessive neurite growth, differentiation or survival, including but not limited to: ALS; general ataxia; Parkinson's disease; Alzheimer's disease; Huntington's disease; general neuropathy; cerebral palsy; neurologic trauma; and mental retardation.

The compounds of the invention may be designed or administered for tissue specificity. If the compound comprises a nucleic acid molecule, including those comprising an expression vector, it may be linked to a regulatory sequence which is specific for the target tissue, such as the brain, skin, joints, bladder, kidney, liver, ovary, etc. by methods which are known in the art including those set forth in Hart, 1994, Ann. Oncol., 5 Suppl 4: 59–65; Dahler et al., 1994, Gene, 145: 305–310; DiMaio et al., 1994, Surgery, 116:205–213; Weichselbaum et al., Cancer Res., 54:4266–4269; Harris et al., 1994, Cancer, 74 (Suppl. 3):1021–1025; Rettinger et al., Proc. Nat'l. Acad. Sci. USA, 91:1460–1464; and Xu et al, Exp. Hematol., 22:223–230; Brigham et al., 1994, Prog. Clin. Biol. Res., 388:361–365. The compounds of the invention may be targeted to specific sites of inflammation by direct injection to those sites, such as joints, in the case of arthritis. Compounds designed for use in the central nervous system should be able to cross the blood brain barrier or be suitable for administration by localized injection. Similarly, compounds specific for the bladder can be directly injected therein. Compounds may also be designed for confinement in the gastrointestinal tract for use against disorders such as colorectal carcinoma. In addition, the compounds of the invention which remain within the vascular system may be useful in the treatment of vascular inflammation which might arise as a result of arteriosclerosis, balloon angioplasty, catheterization, myocardial infarction, vascular occlusion, and vascular surgery and which have already been associated with p190 by Pritchard et al., 1994, J. Biol. Chem., 269, 8504–8509. Such compounds which remain within the bloodstream may be prepared by methods well known in the art including those described more fully in McIntire, 1994, Annals Biomed. Engineering, 22:2–13.

5.9.1 EFFECTIVE DOSAGE

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the IC50 (the dose where 50% of the cells show the desired effects) as determined in cell culture. Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). Dosage amount and interval may be adjusted individually to provide plasma levels of the active moiety which are sufficient to maintain the desired effects.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

5.9.2 COMPOSITION AND FORMULATION

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration,the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identity of the co-solvent components may be varied.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

5.9.3 ROUTES OF ADMINISTRATION

Suitable routes of administration may, for example, include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

5.9.4 PACKAGING

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of a disease such as one characterized by insufficient, aberrant, or excessive neurite growth, differentiation, or survival.

6. EXAMPLE

THE INTERACTION BETWEEN CONTACTIN AND THE CAH DOMAIN OF RPTPβ

The subsections below describe the biological interaction between contactin and the CAH domain of RPTPβ. The data demonstrate that ligands for RPTPβ are differentially expressed in neuronal and glial cell lines. In addition, it is shown that a 140 kDa protein from these cell lines interacts with the CAH domain of RPTPβ, and that this 140 kDa protein is contactin. The data also demonstrate that RPTPβ interacts with both membrane-bound and soluble contactin.

6.1. MATERIALS AND METHODS

6.1.1. CELL CULTURE

SF763T and SF767T human astrocytoma cell lines were grown in athymic nu/nu mice to create a tumor derived cell line. The parental lines (SF763 and SF767) were generously provided by Dr. Michael E. Bernes (The Barrow Neurological Institute, Phoenix, Ariz.). All other cell line used were supplied by the American Type Culture Collection (Rockville, Md.). For culturing of rat sensory neuron, spinal sensory ganglia were dissected from newborn rat pups and dissociated by incubation with trypsin (0.05% for 10 minutes). The ganglia were washed several times in L15+ 10% fetal calf serum, and triturated with a pasteur pipette. The resulting single cell suspension was not subjected to preplating. The cells were plated at 15,000 cells per well in an eight-well chamber slide (Nunc) precoated with 10 mg/ml laminin in PBS. The medium was $L15/CO_2$ with supplements as described (Hawrot and Patterson, 1979, Meth. Enzymol., 58:547–584), and nerve growth factor was added at 50 ng/ml. The cells were cultured for two days prior to staining.

6.1.2. GENERATION AND PRODUCTION OF PC-FUSIONS

To construct the Fc-fusion molecule, different subdomains of RPTPβ extracellular region were amplified using pfu (Stratagene, La Jolla, Calif.) and cloned into a unique BamHI site upstream from the hinge region of human IgG1-Fc. For the construction of βC and βCF fusions a DNA fragment was amplified from position −20, within the Bluescript sequence to position 939 and 1245 respectively (βC-Fc aa 1–313, βCF-Fc aa 1–415) (Levy et al., 1993, J. Biol. Chem., 268:10573–10581). In frame fusion was made by creating a BamHI site in the 3' primer maintaining the original amino acids sequence in the fusion junction. These fragments were further cloned into HindIII-BanHI linearized pCγ1 vector, a modified version of pIG1 that contained a cDNA form instead of the genomic fragment of human IgG (Simmons, 1993, in Cellular Interactions in Development. A Practical Approach, Hartley (ed.), IRL Press). The same strategy was used to construct human contactin-Fc (Hcon-Fc) fusion molecule. Briefly, total RNA was prepared from Y79 retinoblastoma cells and converted to single strand cDNA using Superscript II reveres transcriptase (Gibco-BRL) following the suppliers protocol. This cDNA was use as a template to clone human contactin by three overlapping PCR reactions into EcoRI-BamHI sites of pCγ1 vector. In order to use these sites, the EcoRI site at position 3173 (Reid et al., 1994, Brain Res. Mol. Brain Res., 21:1–8), was eliminated by changing a single base during the PCR reaction. The final construct contained amino acids 1–1020 of human contactin fused to the IgG region. To construct βF-Fc the region between nucleotides 901 to 1242 was amplified with a set of primers that introduced SacII and BamHI sites in the ends of the fragment. This fragment was cloned into pCNγ1 between the globulin gene and a sequence encoding a signal peptide derived from TGFβ gene (Plowman et al., 1992, J. Biol. Chem., 267:13073–13078). The integrity of all the above constructs was checked by complete nucleotide sequence determination or by restriction enzyme analysis. Fusion proteins were produced transiently in COS7 cells or by cotransfection with pN1012-Neo into 293 cells and selecting for individual G418 resistant clones as described (Peles et al., 1991, EMBO J., 10:2077–2086). Purification of fusion proteins was achieved by affinity chromatography on Protein-A Sepharose CL 4B (Pharmacia). Bound proteins were eluted with 100 mM sodium citrate PH 2.5, 1M $MgCl_2$, followed by buffer exchange on a PD-10 desalting column (Pharmacia). The proteins were analyzed by gel electrophoresis followed by silver staining (ICN, Costa Mesa, Calif.). Concentration of the purified proteins was determined by bradford reagent (BioRad, Richmond, Calif.), and by an ELISA assay using peroxidase coupled antibody against human IgG (Pierce, Roxford, Ill.). The same antibody was used to detect the fusion proteins by western blotting followed by chemiluminescence reagent (ECL; Amersham) as described previously (Peles et al., 1992, Cell, 20 69:205–216).

6.1.3. EXPRESSION CLONING IN COS CELLS

Total cellular RNA was prepared from GH3 cells using acid guanidinium thiocyanate extraction (Chomczynski and Sacchi, 1987, Anal. Biochem., 162:156–159), and Poly(A) RNA was isolated by two passages over an oligo dT cellulose column (Pharmacia). cDNA was synthesized using the Superscript kit (Gibco BRL, Bethesda, Md.) by priming with a random primer that contained a HindIII site. Following the addition of EcoRI adaptors the double-stranded cDNA was size selected on agarose gel. cDNAs larger then 2 kb were ligated into a EcoRI and HindIII-digested pcMP1 plasmid vector, a derivative of the pCMV-1 vector (Lammers et al., 1993, J. Biol. Chem., 168:24456–22462). E. coli DH1OB cells (GIBCO BRL) were transformed by electroporation REF. This procedure generated a cDNA library with $2\times10^6$ independent clones. Pools of 3000 bacterial clones were grown for 24 hours and scraped from plates using, LB containing 15% glycerol. Twenty percent of the cultures were saved as glycerol stocks at $-70°$ C. and plasmid DNA was prepared from the rest using the Wizard plasmid purification kit (Promega).

Plasmid DNA (10 μg) was transfected into COS7 cell grown on chamber slides (Nunc) with lipofectamin (GIBCO BRL). After 72 hours cells were incubated for one hour with medium containing 0.5 μg/ml βCF-Fc. Unbound Fc-fusion proteins were removed by three washes with cold DMEM/F12 and the cells were fixed with 4% paraformaldehyd in PBS. Immunostaining was performed with ABC staining system (Vector Lab), using biotinylated anti-human IgG antibodies (Fc specific; Jackson Labs, West Grove, Pa.) following by streptavidin alkaline phosphatase and NBT/BCIP as substrate according to the protocol provided by the manufacturer. One positive pool (#54) was subdivided and rescreened until a single clone (F8) was isolated.

DNA sequence determination was carried out using the dideoxy-chain termination method (Sanger et al., 1977, Proc. Natl. Acad. Sci., USA 74:5463), with Sequenase 2.0 (United States Biochemical Corporation, Cleveland, Ohio). Sequencing was performed on both strands by priming with synthetic oligonucleotides.

6.1.4. CONSTRUCTION OF RPTPβ/EGF-RECEPTOR CHIMERAS

To generate a plasmid for the expression of βCF/EK chimeras, a portion of the extracellular domain of RPTPβ containing the CAH and the FNIII domains (βCF, aa 1–418) was fused to the human EGF receptor at position 634, twelve amino acids after the transmembrane domain in its extracellular region. These fragments were amplified using pfu (Stratagene, La Jolla, Calif.) with a specific set of primers that introduce a BstBI site at the junction between the two genes. The resulting fragments were ligated into Bluescript (Stratagene, La Jolla, Calif.). Proper fusion between the two molecules was verified by nucleotide sequence analysis. This chimeric gene was then subcloned into a NotI site in the reteroviral vector SRα-SL and viral stocks where prepared by cotransfecting COS-7 cells with this vector along with a helper virus plasmid (Muller et al., 1991, Mol. Cell. Biol., 11:1785–1792). These viruses where used to infect NIH 3T3 (clone 2.2), which lack endogenous EGF-receptor. Following infection, cells where selected in a medium containing 1 mg/ml G418 (Gibco-BRL) and resistant colonies were individually grown and assayed for the expression of the chimeric receptor by Western blotting with antibodies against the carboxyl terminus of the EGF-R (Kris et al., 1985, Cell, 40:619–625) as described previously (Peles et al., 1992, Cell, 69:205–216).

6.1.5. BINDING OF FC-FUSION PROTEINS

Confluent monolayer of cells were incubated for one hour with conditioned medium containing 0.25–0.5 mg/ml Fc-fusion protein. The unbound proteins were removed by three washes with binding medium (0.1% BSA, 0.2% none fat dry milk in DMEM/F12) and the cells were further incubated with 1 ng/ml [$^{125}$I]-Protein A (Amersham), for 30 minutes at 4° C. Plates were washed three times with cold binding medium and cell bound radioactivity was determined as described previously (Peles et al., 1993, EMBO J., 12:961–971). Cellular staining using the Fc-fusion proteins was done using the procedure described above for expression cloning.

6.1.6. CHEMICAL CROSSLINKING EXPERIMENTS

Cells were incubated for four hours with medium containing, the different Fc-fusion proteins. Following three washes with cold PBS/Ca (1 mM $CaCl_2$ in PBS), the cells were incubated for additional 30 minutes with PBS/Ca containing 1 mM DTSSP (3,3'-Dithiobis[sulfosuccinimidyl-propionate], Pierce, Rockford, Ill.). Free cross-linker was removed by additional PBS wash followed by quenching with 100 mM glycine in TBS for 10 minutes at 4° C. Cell lysates were made in SBN lysis buffer (Peles et al., 1991, EMBO J., 10:2077–2086), and Sepharose-protein A was added to the cleared lysates. Following two hours incubation at 4° C., the beads were washed three times with HNTG buffer (Peles et al., 1991, EMBO J., 10:2077–2086), and the bound proteins were eluted by adding SDS PAGE sample buffer containing 5% β-mercaptoethanol and further incubation for 10 minutes at 95° C.

6.1.7. PROTEIN PURIFICATION AND SEQUENCING

Cellular membranes were prepared from $5\times10^8$ GH3 cells by homogenization in hypotonic buffer that included 10 mM Hepes pH 7.5, 1 mM EGTA, 1 mM $MgCl_2$, 10 μg/ml aprotinin, 10 μg/ml leupeptin and 2 mM PMSF. Nuclei and unbroken cells were removed by low speed centrifugation (1000g×10 minutes at 4° C.), and the supernatant was then subjected to high speed centrifugation at 40000 g (30 minutes at 4° C.). The membrane pellet was resuspended in SML solubilization buffer (2% Sodium monolaurate, 2 mM MgCl2, 2 mM PMSF in PBS). After one hour incubation on ice the detergent-insoluble materials was removed by centrifugation, and the sample was diluted tenfold with PBS containing 2 mM $MgCl_2$. This sample was loaded on a column of βCF-FC bound to Sepharose Protein A (200 μg βCF-Fc/ml beads) at 4° C. The column was washed with SML buffer containing 0.15% detergent and the bound proteins were eluted by adding SDS sample buffer and heating to 95° C. Proteins were separated on 7.5% gel and electroblotted in CAPS buffer (100 mM CAPS, 10% MeOH) to ProBlott membrane (Applied Biosystems). The membrane was stained with coomassie R-250 and the 140 kDa band was excised and subjected to direct microsequencing analysis. Microsequencing was performed with an Applied Biosystems Model 494 sequencer, run using standard reagents and programs from the manufacturer.

To obtain internal peptide sequence the blotted band was moistened with neat acetonitrile, then reduced by the addition of 200 ul of 0.1 M Tris pH 8.5, 10 mM dithiothreitol, 10% acetonitrile. After incubation at 55° C., for 30' the sample was cooled to room temperature and 20 ul of 0.25M 4-vinylpyridine in acetonitrile added. After 30 minutes at room temperature the blots were washed 5 times with 10% acetonitrile. Digestion was performed for 16 hours with 1 ug modified trypsin (Promega) in 50 ul of 0.1M Tris pH 8.0, 10% acetonitrile, 1% octylglucoside. Digestion was stopped by the addition of 2 ul of neat trifluoroacetic acid (TFA). Peptides were separated on a 1 mm×200 mm Reliasil C-18 reverse phase column on a Michrom UMA HPLC run at 50 ul per minute. Solvents used were 0.1% TFA in water and 0.085% TFA in 95% acetonitrile/5% water. A linear gradient of 5 to 65% B was run over 60 minutes. Absorbance was monitored at 214 nm and peaks were collected manually into a 96 well polyethylene microtitre plate. Purified peptides were sequenced as described above.

6.1.8. TREATMENT WITH PI-PLC

Cells grown to confluency in 90 mm dishes were metabolically labeled with 100 μCi/ml [$^{35}$S]-methionine and cysteine mix (NEN, Boston, Mass.) for four hours at 37° C. Labeled cells were washed three times with MEM and incubated with 250 mU of phosphatidylinositol specific phospholipase C (PI-PLC, Boehringer Mannheim or a kind gift from Dr. J. Salzer) for 50 minutes at 37° C. The supernatant was collected and cleared by centrifugation (1000 g), membranes were prepared from the cells and further solubilized in SML buffer as described above. βCF-Fc bound to Sepharose-protein A beads was added to the supernatant and the membrane fractions for one hour at 4° C. The beads were washed twice with 0.15% sodium monolaurate in PBS and once in PBS before the addition of SDS sample buffer. The precipitated proteins were separated on 7.5% cell and subjected to autoradiography.

For binding experiments, cell were treated with different amounts of PI-PLC (as indicated in the legend to the figures) in MEM containing 0.5% BSA for 30–60 minutes at 37° C. Cells were briefly washed and binding of βCF-Fc was performed as described above.

6.2. RESULTS 6.2.1. THE CAH DOMAIN OF RPTPα MEDIATES AN INTERACTION WITH NEURONS

To identify cellular ligands for RPTPα, fusion proteins were constructed between different subdomains of RPTPα and the Fc portion of human IgG. Three chimeric constructs were made, one containing both the carbonic anhydrase and the fibronectin domains (βCF-Fc) and two others carrying each domain by itself (βC-FC or αF-FC). Initially, βCF-Fc was used to screen for a membrane bound ligand on the surface of different neuronal and glial cell lines. Several cell lines that bind this fusion protein were identified. These were the IMR-32 neuroblastoma cells, the two closely related neuroendocrine derived cell lines GH3 and GH1, and five different glioblastoma cell lines.

The fact that these positive cell lines were derived from glial and neuronal origins raised the possibility that RPTPβ may interact with two different membrane-associated ligands. Alternatively, a single ligand may exist which is expressed by both neurons and glia cells. To explore these two possibilities it was examined whether a fusion protein that contained only the CAH domain of RPTPβ (βC-Fc) will retain the same cell specificity observed with βCF-FC. It was reasoned that in a multidomain receptor like RPTPα, each domain might function as an independent unit in terms of its interaction with a specific ligand. Thus, the use of a single domain in binding experiments might allow the identification of a cell type specific ligand. As depicted in FIG. 2A, this fusion protein, indeed, binds to the same neuronal and neuroendocrine cell lines. In contrast, none of the glioblastomas were positive, suggesting that there are at least two ligands for RPTPα that are differentially expressed on neuronal or glial cells. This result also implied that the CAH domain mediates the interaction of RPTPβ with a specific ligand present in neurons but not in glia cells.

Accordingly, if the binding of βC-FC to neuronal ligand reflects the interactions occurring in vivo, one would expect to see similar binding specificity on cultures of primary neurons. The binding of the different fusion proteins to cultured dorsal root ganglion cells (DRG), followed by detection of the bound proteins by immunostaining, was analyzed. βC-FC and βCF-FC bound to GH3 cells, as well as to the primary neurons. A fusion protein containing the fibronectin domain alone (αF-Fc) failed to bind to either GH3 cells or DRG neurons. In other experiments, binding of αF-FC to several glial cell lines was detected, but no binding of this domain to neuronal derived cell lines or neurons derived from rat DRGs and chick cortex was detected. In addition, it was examined whether the binding specificity observed with the CAH domain of RPTPβ is unique to this receptor by comparing it with the related phosphatase RPTPγ (Barnea et al., 1993, Mol. Cell. Biol., 13:1497–1506). A fusion protein made with the CAH domain of this highly homologous family member did not bind to GH3 cells or to primary neurons.

Altogether these results suggests that specific ligands for RPTPβ exist on the surface of cells from neuronal and glial origin. Different subdomains of the receptor mediate its interaction with those distinct ligands. The CAH mediates an interaction with neurons while the FNIII enables the interaction of RPTPβ with glia cells. In the work presented here, the identification and molecular characterization of the ligand for the CAH domain is described.

6.2.2. COVALENT CROSSLINKING EXPERIMENTS REVEAL A 140 KDA PROTEIN THAT INTERACTS WITH THE CAH DOMAIN OF RPTPα

To characterize ligands for RPTPβ, a reversible cross-linker (DSSTP) was used, and proteins were sought that specifically bound to βC-Fc. Two of the cell lines that bound βC-Fc (IMR32 and GH3), as well as COS7 cells as a control, were allowed to react with the fusion proteins containing the FNIII or the CAH domains followed by cross-linking and precipitation of the complexes. As shown in FIG. 3, a protein of about 140 kilodalton specifically reacted with βC-Fc in the rat GH3 and human IMR-32 cells. No reactivity was detected in control cells or in cells incubated with αF-FC. The cross-linker (DSSTP) used, undergoes cleavage in the reducing SDS PAGE conditions and, therefore, permits the identification of the true molecular weight of the putative ligand. This result suggested that the same ligand is expressed in the rat GH3 and the human IMR-32 lines.

6.2.3. MOLECULAR CLONING OF A CANDIDATE LIGAND FOR RPTPα FROM RAT GN3 CELLS REVEALS THE RAT HOMOLOGUE OF CONTACTIN

An expression cloning strategy was employed in an effort to clone the gene that encodes the 140 kDa candidate ligand. we have employed. Plasmid pools made from a GH3-cDNA library were transfected into COS7 cells and the cells were screened for their ability to bind βCF-Fc. Positive cells were detected by immunostaining with biotinylated anti-human IgG antibodies and sterptavidin alkaline phosphatase. One positive pool was identified that when transfected yielded several stained cells on the slide. This pool was subdivided and rescreened four times until a single clone (F8) was isolated. Transfection of COS7 cells with this plasmid resulted in positive staining of approximately 25%–50% of the cells, a number that correlates well with the maximum transfection efficiency in our system. DNA sequence analyses of clone F8 showed that it contained a 3.9 kb insert and a single long open reading frame of 3063 nucleotides. The deduced 1021 amino acid sequence encoded by this clone has been presented elsewhere. Data bank search with this sequence showed that it shares 95% and 99% identity at the amino acid level with human and mouse contactin respectively (Berglund and Ranscht, 1994, Genomics, 21:571–582; Gennarini et al., 1989, J. Cell. Biol., 109:755–788; Reid et al., 1994, Brain Res. Mol. Brain Res., 21:1–8). It was therefore concluded that the ligand for RPTPβ cloned from GH3 cells is the rat homologue of contactin. Structurally, this protein consists of six C2 type Ig domains, four fibronectin type III repeats and an hydrophobic region that mediates its attachment to the membrane by a GPI linkage (Gennarini et al., 1989, J. Cell. Biol., 109:755–788; Reid et al., 1994, Brain Res. Mol. Brain Res., 21:1–8). Functionally, it is a neural cell adhesion molecule that has been suggested to play a morphogenic role during the development of the nervous system (Rathjen et al., 1987, J. Cell. Biol., 104:343–353; Walsh and Doherty, 1991, Cell. Biol. Int. Rep., 15:1151–1166).

In parallel to the expression cloning strategy, and as a complementary approach, a biochemical procedure was employed that utilized the CAH domain as an affinity reagent for protein purification. p140 was purified from solubilized membranes prepared from GH3 cells on a column of βCF-Fc. After resolving the eluted protein on SDS/PAGE, the 140 kDa species was subject directly to N-terminal sequencing, or was digested with trypsin. Two peptide sequences obtained, one from the N-terminus and the other from an internal peptide after tryptic digest. Both sequences matched the translated F8 sequence and confirmed that contactin is indeed a ligand for the CAH domain of RPTPβ.

6.2.4. BINDING ANALYSIS OF RPTPβ AND CONTACTIN

The binding specificity of different subdomains of RPTPβ towards contactin was examined. COS7 cells were transfected with rat contactin (clone F8) and analyzed for their ability to bind fusion proteins containing the CAH, FNIII or both domains. As expected, expression of contactin enabled the binding of the CAH domain of RPTPβ to the cells. The FNIII domain alone did not bind to contactin expressing cells. In addition, similar results were obtained with a fusion protein that carries most of the extracellular region of the short form of RPTPβ (aa 1–644; data not shown).

The reciprocal interaction, namely, whether soluble contactin molecules are able to bind specifically to cells expressing RPTPβ, was explored next. In these experiments, COS7 cells were transfected with chimeric receptor constructs that consist of the entire extracellular region of the short form of RPTPβ (βCFS/EK), the CAH domain plus the FNIII repeat (βCF/EK), or the CAH domain alone (βC/EK) fused to the transmembrane and intracellular domains of the EGF receptor. A chimeric receptor was used instead of the wild type phosphatase because the wild type phosphatase was not able to be expressed in heterologous cells. Human contactin-Fc fusion protein binds to cells transfected with these chimeric receptors but not to control cells. Taken together, these results demonstrate that expression of contactin is both necessary and sufficient for binding to the CAH domain RPTPβ.

6.2.5. SOLUBLE CONTACTIN RELEASED FROM THE MEMBRANE BY PHOSPHOLIPASE C TREATMENT INTERACTS WITH RPTPβ

Contactin belongs to a family of recognition molecules that TAG-1 and BIG-1, all of which are anchored to the plasma membrane via a glycosyl-phosphatidylinositol (GPI). Therefore, it was of interest to see how phospholipase C (PI-PLC) treatment would effect the interaction between contactin and RPTPβ. When incubated with COS7 cells expressing contactin (clone F8), PI-PLC completely abolished the binding of βCF-Fc to the cells. Similar results were obtained also with GH3 cells.

It has been demonstrated that members of this family and other GPI-linked proteins may exist either in a membrane bound or a secreted soluble form that is released from the cell surface (Furley et al., 1990, Cell, 61:157–170; Théveniau et al., 1992, J. Cell. Biochem., 48:61–72). Hence, it was examined whether the different forms of contactin, including those released after PI-PLC treatment, could interact with RPTPβ. To this aim, GPI-linked proteins were released from metabolically labeled GH3 cells with the enzyme, and purified contactin by bioaffinity precipitation from membrane extracts of the cells or the cell supernatants. Without PI-PLC treatment, two proteins p140 and p190 from the membrane fraction could specifically associate with βC-Fc. These proteins were not present in the supernatant and they were not detected with βF-Fc. However, after PI-PLC treatment, p140/contactin could be precipitated from the medium of the cells, indicating that the soluble form produced by phospholipase treatment interacts with RPTPβ. This result may suggest that, in addition to the interaction between the membrane bound forms of these proteins, soluble contactin could potentially interact in vivo with RPTPβ. βC-Fc could precipitate the 190 kilodaltons protein only from membrane fraction and not from the cell supernatant. PI-PLC treatment did not release this protein from the cells suggesting that it is either an integral membrane protein or a cytoskeletal protein associated with contactin complexes. Since contactin by itself is sufficient to mediate the interaction with RPTPβ, the 190 kDa protein may be associated with contactin in the cells and coprecipitated with it during the bioaffinity procedure. One intriguing possibility is that p190 is a signaling unit used by contactin on the surface of neurons (see below).

7. EXAMPLE

THE CAH DOMAIN OF RPTPβ INDUCES CONTACTIN MEDIATED NEURITE OUTGROWTH

The subsections below describe the induction, by the CAH domain of RPTPβ, of contactin mediated neurite outgrowth. It is shown that the CAH domain of RPTPβ is a permissive substrate for neuronal adhesion and neurite growth. In addition, it is also shown that the neurite growth, differentiation and survival induced by the carbonic anhydrase-like domain of RPTPβ is mediated by neuronal contactin.

7.1. MATERIALS AND METHODS

The materials and methods for this example were the same as those set forth in the example described in section 6.1 above, except as supplemented or amended below.

7.1.1. NEURITE OUTGROWTH ASSAYS

Neurite outgrowth assays using IMR 32 cells were performed as described previously (Friedlander et al., 1994, J. Cell. Biol., 125:669–680) using 35 mm petri dishes coated with different proteins adsorbed on the substrate. After blocking the dishes with 1% BSA/PBS, the blocking solution was replaced with $3 \times 10^4$ cells suspended in 140 µl of DMEM/F12/ITS. Following incubation for 3 hrs at 37° C. during which time most of the cells adhered to the dish, the medium was removed and replaced with DMEM/F12/ITS medium containing antibodies (Ig fraction purified by ammonium sulfate precipitation and DE52 chromatography). Dishes were incubated for 48 hrs and fixed with Hanks/0.3% sucrose 2.5% paraformaldehyde. For PI-PLC treatment, primary tectal neurons ($5 \times 10^4$ cells/250 ml) were prepared from E9 chick embryos (Grumet et al., 1984, Proc. Natl. Acad. Sci. USA, 81:267–271) and incubated with 0.25 µl of PIPLC (1.7 U/ml) in DMEM/F12/ITS+ at 37° C. for 30 min. The cell suspension was then incubated on dishes coated with different substrates without changing the medium.

7.2. RESULTS 7.2.1. NEURITE OUTGROWTH INDUCED BY THE CAH DOMAIN OF RPTPβ IS MEDIATED THROUGH CONTACTIN

Contactin has been shown to be involved in both positive and negative responses of neurons to various stimuli (Brümmendorf and Rathjen, 1993, J. Neurochem., 61:127–1219). When presented as a ligand to neurons, either as a membrane-bound or a soluble form, contactin induces axonal growth (Brümmendorf et al., 1993, Neuron, 10:711–727; Clarke et al., 1993, Eur. J. Cell. Biol., 61:108–115; Durbec et al., 1992, J. Cell. Biol., 117:877–887; Gennarini et al., 1989, J. Cell. Biol., 109:755–788). Its neural receptor has been identified as the recognition molecule Nr-CAM (Morales et al., 1993, Neuron 11:1113–1122). On the other hand, contactin itself is a receptor present on neurons and mediates their repulsion by the extracellular matrix protein janusin (Pesheva et al., 1993, Neuron, 10:69–82). The results described in the example of Section 6.1 indicate that the CAH domain of RPTPβ can bind to contactin on cells. To analyze effects of this binding on neurons, chick tectal cells, known to express contactin, were plated on dishes previously coated with βCF-Fc fusion protein or with Ng-CAM or laminin as controls. Cells attached and grow processes on both of these substrates. Treatment of the cells with PI-PLC prior to plating completely abolished cell attachment and neurite extension on RPTPβ. In contrast, PI-PLC did not have a dramatic effect on cells growing on Ng-CAM or laminin as substrate. Thus, it was concluded that the CAH domain of RPTPβ is a permissive substrate for neuronal adhesion and neurite growth. Moreover, the cell adhesion and axonal elongation induced by RPTPβ is mediated through a GPI-anchored receptor.

Next it was investigated whether contactin could be the neuronal receptor for the CAH domain of RPTPβ. To this aim, a human neuroblastoma cell line IMR-32 was used that has the capacity to differentiate and to elaborate neurites in response to different stimuli (Lüdecke and Unnsicker, 1990, Cancer, 65:2270–2278). These cells have fibroblastic morphology when crown on petri dishes coated with fibronectin, but on laminin substrates they assume a neuronal phenotype and extend processes with growth cones. A similar morphologic differentiation was seen after plating the cells on the CAH domain of RPTPβ. In contrast, the CAH domain of RPTPγ had no effect on cell adhesion and differentiation. These results show that IMR-32 cells respond specifically to the carbonic anhydrase domain of RPTPβ. To determine whether contactin could be acting as a receptor on the IMR-32 cells for RPTPβ, the effects of antibodies against contactin on the growth of cells on different substrates were tested. Antibodies against contactin inhibited the growth of processes on βC-Fc and βCF-Fc but not on laminin. In the presence of these antibodies, the IMR-32 cells also retracted their processes and many cells lifted off the dish yielding fewer cells after 2 days of incubation. No effect was observed with control antibodies. Thus, the neurite growth, differentiation and survival induced by the carbonic anhydrase-like domain of RPTPβ is mediated by contactin present in the neurons.

8. EXAMPLE

THE CLONING OF p190 AND THE INTERACTION BETWEEN IT AND CONTACTIN

The subsections below describe the purification and sequencing of p190 protein and the subsequent cloning of rat and human p190 cDNA. The interaction between p190 and contactin is also demonstrated.

8.1 MATERIALS AND METHODS 8.1.1 Protein Purification and Sequencing

Solubilized membrane lysate was prepared from $3 \times 10^9$ GH3 cells and loaded on a column of βCF-Fc bound to Sepharose protein A (Pharmacia) as described previously (Peles et al., 1995, Cell, 82:251–260). Bound proteins were separated on 6.5% SDS gel, blotted to ProBlot membrane (Applied Biosystem, Inc.) and stained with Coomassie R-250. To obtain internal peptide sequence, the blotted 190 kDa band was moistened with neat acetonitrile and then reduced by the addition of 200 ul of 0.1M Tris pH 8.5, 10 mM dithiothreitol, 10% acetonitrile. Digestion was performed for 16 hours with 1 μg modified trypsin (Promega) in 50 μl of 0.1M Tris pH 8.0, 10% acetonitrile, 1% octyl-glucoside. Digestion was stopped by the addition of 2 μl of neat trifluoroacetic acid (TFA). Peptides were separated on a 1 mm×200 mm Reliasil C-18 reverse phase column on a Michrom UMA HPLC run at 50 ul per minute. Solvents used were 0.1% TFA in water and 0.085% TFA in 95% acetonitrile/5% water. A linear gradient of 5 to 65% B was run over 60 minutes. Absorbance was monitored at 214 nm and peaks were collected manually into a 96 well polyethylene microtiter plate. Purified peptides were sequenced as described (Peles et al., 1995, Cell, 82:251–260).

8.1.2 Cloning of Rat an Human CASPR/p190 cDNA

The sequence of one tryptic peptide obtained from the purified protein (QNLPQILEES) (SEQ ID NO: 29) was found in a 900 bp EST fragment B102/LF98 from the BRCA1 region on chromosome 17q21 (Friedman et al., 1994, Cancer Res., 54:6374–6382). Primers corresponding to this region ($_5$' primer: TCG CAG GCT ATG AGC CTG GCT ACA TCC (SEQ ID NO: 30); 3' primer: GTG GGT AGG GGA GGT TTG CTG CCA GG) (SEQ ID NO: 31) were use for RT-PCR to clone this DNA fragment from rat GH3 cells. A 600 bp DNA fragment derived from this region was further used as a probe to screen a ZAPEX-GH3 cDNA library. This cDNA library was constructed in ZAP-Express phage (Stratagene, San Diego, Calif.), using oligo dT priming. Plate hybridization and other cloning techniques were performed according to standard procedures (Sambrook et al., 1989, Molecular cloning: A Laboratory Manual, 2nd Edition (Cold Spring Harbor, N.Y.: Cold Spring Harbor Laboratory)). Clone ZX5 had a 2.5 kb insert that contained in addition to the B102 fragment, a sequence downstream that matched additional peptide sequence. A second cDNA library was made from GH3 mRNA by priming with a specific oligonucleotide GGA GGT CTC CTT TAG (SEQ ID NO: 32) according to the sequence that was found in the 5' end of clone ZX5. This cDNA was cloned into ZAP-Express (Stratagene, San Diego, Calif.) to generate ZB-GH3 library. This library was use to isolate multiple clones that overlapped with ZX5 and contained the 5' end of the gene. To clone the human gene a cDNA library was made from IMR32 neuroblastoma cells in ZAP-Express (ZX-IMR). Probes were generated by PCR from the 5' ends of rat clone ZB181 and from IMR32 cDNA according to the B102 sequence as described above for the rat gene. Several clones had a 5 kb insert that contained the full length gene. DNA sequence determination was carried out using the dideoxy-chain termination method with Sequenase 2.0 (United States Biochemical Corporation, Cleveland, Ohio). Sequencing was performed on both strands by priming with synthetic oligonucleotides.

8.1.3. Expression Constructs

An EcoRI-XhoI fragment containing the 5' end of rat CASPR/p190 (from clone ZB161) was ligated with an XhoI-EcoRI fragment containing the 3' end of the gene (from clone ZB181) and cloned into pCMP1 (Peles et al., 1995, Cell, 82:251–260) to generate pCM190R. An HA-tagged version of the gene was constructed by replacing an EcoRI-AccI fragment with a PCR-generated fragment containing the HA-tag sequence. This resulted in the addition of the HA sequence to the 3' end of the coding region of rat CASPR/p190 to generate pCM190HA. Construction of contactin expression vectors was previously described (Peles et al., 1995, Cell, 82:251–260). The plasmids pSGT-cSRC and pSGT-fyn, containing human src and fyn genes and the plasmids used for generation of the GST-SH3s fusions were described previously (Erplel et al., 1995, EMBO J., 14:963–975). To generate a GST-fusion protein containing the cytoplasmic tail of rat CASPR/p190, the corresponding region (aa 1308–1380) was amplified by PCR and cloned into pGEX-4T (Pharmacia). The sequence of the final construct was verified by DNA sequencing.

8.1.4. Northern Blot Analysis

Multiple tissue northern blots (MTN Blots, Clontech) were Used. A DNA fragment (position 3600–4232 of human CASPR/p190) was generated by RT-PCR from IMR32 mRNA. This fragment was labeled by random priming ("prime it"; Stratagene, San Diego, Calif.), purified using PCR-clean column (Qiagen) and used as a probe. Hybridization was carried out for 16 hours in a buffer containing 5×SSC, 5×Denhart's solution, 50% formamide, 0.2% SDS and 100 ug/ml denatured salmon sperm DNA at 42oC. The blots were washed at 6° C. twice in a buffer containing 0.5×SSC, 0.1% SDS and once with 0.1×SSC, 0.2% SDS. Signals were detected by autoradiography. The same membranes were reprobed with a 2 kb human β-actin cDNA as a control probe (Clontech, Palo Alto, Calif.).

8.1.5. Imunohistochemistry and Ig-Fusion Binding

Production of different Ig-fusion chimeric proteins and cell binding experiments were done exactly as described previously (Peles et al., 1995, Cell, 82:251–260). Staining of tissue sections with antibodies was done essentially as described (Milev et al., 1994, J. Cell Biol., 127:1703–1715).

8.1.6. Generation of Antibodies

Polyclonal antibodies against CASPR/p190 were generated according to standard procedures (Harlow, 1990, Antibodies: A Laboratory Manual). Ab60 was obtained by immunizing rabbits with a GST-fusion protein containing all the cytoplasmic domain of rat CASPR/p190 (GST-190CT). Affinity purification was achieved first by passing the serum on a column of Sepharose-GST. Then, the unbound material was loaded on a column of GST-190CT Sepharose. Bound antibodies were eluted with 100 mM sodium citrate pH 2.8 and 1.5 M $MgCl_2$. Eluted material was precipitated with ammonium sulfate, resuspended in DDW and extensively dialysis against PBS. Antibody 87AP was generated against an eight aa long peptide corresponding to the C-terminal sequence of rat CASPR/p190. Affinity purification on a Sepharose-peptide column was done essentially as described above for Ab60. Antibodies against F3 were previously described (Faivre-Sarrailh et al., 1992, J. Neurosci., 12:257–267). Antibody CST1 that recognize Src, Fyn and Yes was previously described (Erplel et al., 1995, EMBO J., 14:963–975). Ab18 against Src and Ab16 against Fyn were purchased from Santa Cruz Antibodies (Santa Cruz, Calif.). Monoclonal antibody against HA-tag was purchase from Boehringer. Mouse polyclonal antibody against contactin was generated by immunization of mice with purified human contactin-Ig fusion protein according to Yoshihara et al, 1994, Neuron, 13:415–426.

8.1.7. Generation of Anti HCon-Ig Sera

Immunoprecipitation and Western blot analysis: COS transfection protocol using Lipofectamine (Gibco-BRL) was previously described (Peles et al., 1995, Cell, 82:251–260). To detect the association between Contactin and CASPR/p190 the cells were grown to subconfluency and were metabolically labeled with 100 mCi/ml [$^{35}$S]-methionine and cysteine mix (NEN, Boston, Mass.) for four hours at 37° C. Membranes were prepared from the cells and further solubilized in SML buffer (2% Sodium monolaurate, 2 mM $MgCl^2$, 2 mM PMSF in PBS). βC-Fc bound to Sepharose-protein A beads was added to a tenfold adiluted supernatant and incubated for two hours at 4° C. The beads were washed twice with 0.15% sodium monolaurate in PBS and once in PBS before the addition of SDS sample buffer. The precipitated proteins were separated on 7.5% gel and subjected to autoradiography.

Preparation of rat brain membranes: five P7 rat brains were pooled and homogenized in a glass homogenizer in a buffer containing 20 mM Hepes pH 7.4, 0.32 M sucrose, 1 mM EGTA, 1.5 mM $MgSO_4$, 10 µg/ml Aprotinin and Leupeptin and 1 mM PMSF. Nuclei and heavy cell debris were removed by low speed centrifugation (3000g×10 minutes at 4° C.), and the supernatant was then subjected to high speed centrifugation at 40,000 g for 60 minutes. The membrane pellet was resuspended in SML solubilization buffer. After one hour incubation on ice the detergent-insoluble materials was removed by centrifugation. The sample was diluted four to tenfold with PBS containing 2 mM $MgCl_2$ and subjected to precipitation with antibodies or Ig-fusions.

Biotinylation of cell surface molecules was carried out for 20 minutes at 23° C. using 50 µg/ml Biotin-LC-NHS (Pierce). The reaction was stopped by adding $NH_4Cl$ to final concentration of 10 mM followed by two washes with TBS-glycine buffer (50 mM Tris pH 7.4, 150 mM NaCl and 50 mM glycine) on ice prior to solubilization.

Immunoprecipitation and western blotting was performed as described previously (Peles et al, 1992, Cell, 69:205–216). Blots were reacted with streptavidin-linked peroxidase (Amersham) and detected using chemiluminescence reagent (Pierce).

8.2. RESULTS

8.2.1. CASPR/p190 Gene and Geone Products

The 190 kD protein which associates with the CAH-contactin complex was purified using affinity chromatography with βC-Fc, utilizing the techniques described, above, in Section 8.1. Briefly, membrane lysates from GH3 cells were applied to a βC-Fc column and bound proteins were separated by SDS-PAGE. The protein believed to correspond to p190 was excised and subjected to trypsin digestion. The amino acid sequences of two tryptic peptides were determined using a gas-phase microsequencer. The amino acid sequences obtained were then utilized to identify corresponding DNA fragments encoding such sequences, as described, above, in Section 8.1. The DNA fragments thus obtained were in turn used to isolate cDNA molecules encoding the full length p190 gene products of both human and rat.

The human CASPR/p190 nucleic acid sequence is depicted in SEQ ID NO:1, and the human CASPR/p190 amino acid sequence is depicted in SEQ ID NO:2. The rat CASPR/p190 nucleic acid sequence is depicted in SEQ ID NO:3, and the rat CASPR/p190 amino acid sequence is depicted in SEQ ID NO:4.

The human and rat CASPR/p190 transcripts have open reading frames that encode for 1384 and 1381 amino acids, respectively, and share 93% identity at the amino acid level. CASPR/p190 is a putative type I transmembrane protein with a short proline-rich cytoplasmic domain. (The transmembrane domain is marked as TMD in FIGS. 1A and 1B).

The first p190 methionine is followed by a stretch of 19–20 amino acid residues rich in hydrophobic residues, which probably acts as a signal sequence. The extracellular domains of rat and human CASPR/p190 contain 1281 and 1282 amino acid residues, respectively. The extracellular region of CASPR/p190 contains 16 potential N-linked glycosylation sites followed by a second hydrophobic stretch that is a typical transmembrane domain.

The CASPR/p190 extracellular domain is a mosaic of several motifs known to mediate protein-protein interactions. Near the N-terminus of mature CASPR/p190 (109 amino acid residues) is a domain with 31–33% amino acid identity to the C1 and C2 terminal domains of coagulation factors V and VIII (Jenny et al., 1987, Proc. Natl. Acad. Sci. U.S.A., 84:4846–50; Wood et al., 1984, Nature, 312:330–37) and 26% identity with the neuronal adhesion molecule neurophilin (previously known as the neuronal A5 antigen) and 20% identity to a region of discoidin I, a lectin from the slime mold Dictyostelium discoideum (Takagi et al., 1991, Neuron, 7:295–307). The domain is marked as DISC in FIGS. 1A and 1B. The extracellular domain of CASPR/p190 also contains four repeats, of approximately 140 amino acid residues each, with homology to neurexins, a family of polymorphic neuronal cell surface proteins. These domains are marked as NX1–NX4 in FIGS. 1A and 1B. There are 6 copies of the motif in the $\alpha$-neurexins, one in the $\beta$-neurexins, and one to five in the C-terminal portions of laminin A, agrin, slit, and perlecan (Ushkaryov et al., 1992, Science, 257:50–56). Together, the five motifs in the basement membrane protein laminin A are referred to as the G domain, a region suggested to mediate cell adhesion. The first three neurexin motifs of CASPR/p190 share 29–32% amino acid identity to regions of rat neurexinIII-$\alpha$ and neurexinII-$\alpha$, whereas the fourth motif is most similar to agrin (34% identity). CASPR/p190 also contains two epidermal growth factor (EGF)-like modules (marked as EGF1–EGF2 in FIGS. 1A and 1B); both of which are most related to repeats within the drosophila neurogenic proteins Notch and slit (39–46% identity) (Rothberg et al., 1988, Cell, 55:1047–59; Wharton et al., 1985, Cell, 43:567–81). A single domain related to the C-terminal region of fibrinogen beta/gamma (marked as FIB in FIGS. 1A and 1B) is flanked by an EGF and neurexin motif. Finally, there is a stretch of 47 amino acids, that is identical between human and rat CASPR/p190, and contains seven copies of Pro-Gly-Tyr-$X_{1-2}$ and three additional imperfect repeats of this sequence (marked as PGY in FIGS. 1A and 1B). The Pro-Gly-Tyr repeat is found in a molluscan adhesive protein (SW:A61077, and a putative chicken prior protein (SW:A46280), whereas the Pro-X-Tyr repeat is present in multiple copies in a soybean cell wall protein (SW:A29324) and the X-Gly-Tyr repeat in heterogeneous nuclear RNP proteins (SW:B41732). The cytoplasmic domain of human and rat CASPR/p190 contain 78 and 74 amino acids, respectively. These include a 38–42 amino acid proline-rich motif (38% proline), the majority of which consists of proline residues alternating with alanine, glycine, or threonine residues (marked as PRO in FIGS. 1A and 1B). Alignment of this region with the non-redundant protein database revealed several proteins containing such "PAPA" motifs. Proline-rich domains can serve as binding sites for SH3-containing protein, yet none of the proteins that align with this domain of CASPR/p190 are known to interact with an SH3 motif.

8.2.2. CASPR/p90 Expression

Northern blot analysis of mRNA isolated from human tissues reveals that CASPR/p190 was expressed predominantly in the brain as a 6.2 kb transcript. Weak expression of CASPR/p190 was detected in ovary, as well as in the pancreas, colon, lung, heart, intestine and testis. Similar results wee obtained for rat tissue hybridized with a rat CASPR/p190 probe.

A high level of CASPR/p190 was detected in different regions of the adult human nervous system, including high expression in the cortex, cerebellum and in the thalamus, while weaker expression is detected in the spinal cord and in the corpus callosum. These analyses demonstrated that the CASPR/p190 gene was expressed predominantly in the central nervous system.

Polyclonal rabbit antibodies raised against a GST fusion protein containing the CASPR/p190 cytoplasmic domain were raised and used to stain permeabilized human IMR-32 neuroblastoma and rat GH3 neuroendocrine cell lines found to express CASPR/p190. These studies revealed recognition of a 190 kD protein.

Similar results were obtained staining COS7 cell lysates that had been transfected with an expression vector directing the synthesis of CASPR/p190. No CASPR/p190 was detected in mock-transfected or untransfected cells.

Immunohistochemistry studies were then performed which demonstrated that CASPR/p190 and contactin localized in the rat retina. Specific CASPR/p190 staining was seen in the ganglion cell fiber layer and in the inner plexiform layers. Similar staining was observed for contactin, with the highest expression in the nerve fiber layer containing the axons that project from the ganglion cells into the optic nerve. Thus, CASPR/p190 and contactin colocalize on neurons in fiber-rich areas of the retina. Further, increased CASPR/p190 staining was detected in membrane preparations from rat brains from E18 to post-natal day eight, a period of extensive axonal outgrowth and synaptogenesis. A similar temporal expression pattern was detected in this tissue in the same period (Gennarini et al., 1989, J. Cell Biol. 109:755–788).

8.2.3. Lateral Interaction in the Plasma Membrane Between CASPR/p190 and Contactin The interaction between contactin, RPTP$\beta$ and CASPR/p190 was then investigated using soluble and membrane-associated variants of these proteins. Specifically, the possibility that the interaction between contactin and CASPR/p190 requires that both proteins be present on the same cell (cis interaction) was studied.

To examine this possibility, COS7 cells were transfected with expression vectors that expressed either CASPR/p190 alone or together with contactin. Lysates of transfected cells were subject to precipitation analysis with the CAH domain of RPTP$\beta$ ($\beta$C-Fc). The CAH domain of RPTP$\beta$ only precipitated CASPR/p190 from cells co-expressing contactin. Thus, it appears that the CAH domain of RPTP$\beta$ can form a ternary complex with contactin and CASPR/p190 proteins. Similar results were obtained using an expression vector expressing tagged CASPR/p190.

Moreover, soluble contactin molecules did not associate with CASPR/p190 when RPTP$\beta$ and CASPR/p190 were co-expressed in the same cells.

On the basis of these experiments, it appears that the CAH domain of RPTP$\beta$ does not bind directly to CASPR/p190 and that contactin and CASPR/p190 are complexed by means of lateral interactions (cis) in the membrane, thus explaining the reason why the protein is referred to as CASPR (ie., Contactin-associated protein).

8.2.4. Complex Formation Between CASPR/p190 and Contactin

The role of RPTP$\beta$ in formation of the CASPR/p190-contactin complex was next examined. IMR-32 cell lysates were subjected to immunoprecipitation with CASPR/p190 antibodies followed by immunoblotting with contactin antibodies. These experiments demonstrated that contactin and CASPR/p190 were constitutively associated on the surface of the IMR-32 cells. In this cell line, it appeared that virtually all CASPR/p190 molecules were associated with contactin.

The existence of an in vivo contactin-CASPR/p190 complex was also demonstrated using rat brain tissue. Lysates of P7 rat brain membranes were subjected to precipitation with βC-Fc followed by immunoblotting with antibodies specific to either contactin of CASPR/p190.

Taken together, these data demonstrate that contactin and CASPR/p190 are constitutively complexed in neuronal cell lines and tissues and that complex formation between these two proteins does not require RPTPβ.

2.5. Interaction Between CASPR/p190 and SH3 Domains of Signaling Molecules

Experiments described herein demonstrated that the CASPR/p190 cytoplasmic domain can serve as a binding site for SH3 domains of signalling molecules which will transmit the signal initiated by RPTPβ binding to the contactin-CASPR/p190 complex.

Specifically, four of seven GST-SH3 domains of signalling molecules were able to bind selectively to the CASPR/p190 protein, including the SH3 domains of Src, Fyn, p85 and PLCγ. Association was not detected with Csk, Grb2 or Gap SH3 domains. CASPR/p190 did not bind to a mutant Src SH3 domain in which a conserved Trp at position 118 was replaced with an Ala residue.

Next it was determined that c-Src could associate with CASPR/p190 fusion proteins in transiently infected COS7 cells. Specifically, lysates of transfected cells were subjected to immunoprecipitation with antibodies against c-Src, followed by immunoblotting with anti-fusion antibodies.

Further, the association between endogenous c-Src and CASPR/p190 in IMR-32 or GH3 cells was investigated using a similar immunoprecipitation/immunoblotting strategy with Src and CASPR/p190 antibodies. Results of such experiments detected no association between c-Src and CASPR/p190.

These experiments raise the possibility that the cytoplasmic domain of CASPR/p190 can serve as a target for SH3 domains of signalling molecules.

What is claimed is:

1. An isolated nucleic acid molecule comprising a nucleotide sequence that:

(a) encodes the amino acid sequence SEQ ID NO:2; or
(b) encodes the amino acid sequence SEQ ID NO:4.

2. An isolated nucleic acid molecule comprising a nucleotide sequence that hybridizes under highly stringent conditions to the full complement of the nucleic acid molecule of claim 1, and encodes a naturally occurring p190 polypeptide, wherein the highly stringent hybridization conditions comprise washing in 0.1×SSC/0.1% SDS at 68° C.

3. An isolated nucleic acid molecule which comprises (a) a nucleotide sequence that encodes a polypeptide having the amino acid sequence shown in SEQ ID NO:2 from amino acid residues 40–168, 199–330, 362–486, 544–576, 582–739, 809–938, 961–985, 1031–1077, 1083–1218, or 1328–1369; or (b) a nucleotide sequence that is fully complementary to the nucleotide sequence of (a).

4. An isolated nucleic acid molecule which comprises
   (a) a nucleotide sequence that encodes a p190 polypeptide lacking at least one, but not all, of the following segments of amino acid residues: 40–168, 199–330, 362–486, 544–576, 582–739, 809–938, 961–985, 1031–1077, 1083–1218, 1282–1306, or 1328–1369 of SEQ ID NO:2; or;
   (b) a nucleotide sequence that is fully complementary to the nucleotide sequence of (a).

5. A recombinant vector comprising the nucleic acid molecule of claim 1, 2, 3, or 4.

6. The recombinant vector of claim 5 wherein the nucleic acid molecule is operatively associated with an element that controls the expression of the nucleic acid molecule in a host cell.

7. A recombinant heterologous host cell comprising the nucleic acid molecule of claim 1.

8. A recombinant heterologous host cell comprising the nucleic acid molecule of claim 1, 2, 3, or 4 operatively associated with an element that controls the expression of the nucleic acid molecule by the host cell.

9. The host cell of claim 7 which is eukaryotic.

10. The host cell of claim 7 which is prokaryotic.

11. A method for preparing a p190 polypeptide comprising:
   (a) culturing a eukaryotic host cell which comprises the nucleotide sequence of claim 1, 2, 3, or 4 operatively associated with an element that controls expression of the DNA sequence so that a p190 polypeptide is expressed by the host cell; and
   (b) recovering the p190 polypeptide from the culture.

12. A method for preparing a p190 polypeptide comprising:
   (a) culturing a prokaryotic host cell which comprises the nucleotide sequence of claim 1, 2, 3, or 4 operatively associated with an element that controls expression of the DNA sequence so that a p190 polypeptide is expressed by the host cell; and
   (b) recovering the p190 polypeptide from the culture.

13. The isolated nucleic acid molecule of claim 1 wherein the nucleotide sequence comprises the nucleotide sequence of SEQ ID NO:1, SEQ ID NO:3, SEQ ID NO:5 or SEQ ID NO:6.

14. An isolated nucleic acid molecule comprising a nucleotide sequence that is fully complementary to the nucleic acid molecule of claim 1.

15. A recombinant vector containing a nucleic acid molecule comprising the nucleic acid molecule of claim 14.

16. A recombinant heterologous host cell containing a nucleic acid molecule comprising the nucleic acid molecule of claim 14.

17. An isolated nucleic acid molecule comprising a nucleotide sequence that is fully complementary to the nucleic acid molecule of claim 2.

18. A recombinant vector containing a nucleic acid molecule comprising the nucleic acid molecule of claim 17.

19. A recombinant heterologous host cell containing a nucleic acid molecule comprising the nucleic acid molecule of claim 17.

20. The host cell of claim 8 which is eukaryotic.

21. The host cell of claim 16 which is eukaryotic.

22. The host cell of claim 8 which is prokaryotic.

23. The host cell of claim 16 which is prokaryotic.

* * * * *

SEQUENCE LISTING

<160> NUMBER OF SEQ ID NOS: 32

<210> SEQ ID NO 1
<211> LENGTH: 5294
<212> TYPE: DNA
<213> ORGANISM: Homo sapiens
<220> FEATURE:
<221> NAME/KEY: CDS
<222> LOCATION: (218)..(4369)

<400> SEQUENCE: 1

```
caagagcgga ggaccaggaa ccagagagag agagagagaa aagagagagg agagacagag      60
cgcttggggg cgaaaggaga gagggaggga agggtgggta aggaggagag agcggtctgc     120
tgcaaacccc aggaggagag cttggagccc aagccagaac tcgagcccta gccggagccg     180
ttcacaggga ggcggctgcc gggaccgtca gccctgc atg atg cat ctc cgg ctc      235
                                         Met Met His Leu Arg Leu
                                           1               5 ttc tgc atc ctg ctc gcc gcg gtc tca gga gcc gag ggc tgg ggc tac       283
Phe Cys Ile Leu Leu Ala Ala Val Ser Gly Ala Glu Gly Trp Gly Tyr
           10                  15                  20 tac ggc tgc gac gag gag ctg gtg ggt ccc ctg tat gca cgc tcc ctg       331
Tyr Gly Cys Asp Glu Glu Leu Val Gly Pro Leu Tyr Ala Arg Ser Leu
       25                  30                  35 ggc gcc tcc tcc tac tac agt ctc ctt act gcg ccg cga ttc gcc agg       379
Gly Ala Ser Ser Tyr Tyr Ser Leu Leu Thr Ala Pro Arg Phe Ala Arg
   40                  45                  50 ctg cac ggc ata agc ggg tgg tca cca cgg att ggg gat ccg aat ccc       427
Leu His Gly Ile Ser Gly Trp Ser Pro Arg Ile Gly Asp Pro Asn Pro
55                  60                  65                  70 tgg ctc cag ata gac tta atg aag aag cac cgg atc cgg gcc gtg gcc       475
Trp Leu Gln Ile Asp Leu Met Lys Lys His Arg Ile Arg Ala Val Ala
               75                  80                  85 aca cag ggc tcc ttt aat tct tgg gac tgg gtc aca cgt tac atg cta       523
Thr Gln Gly Ser Phe Asn Ser Trp Asp Trp Val Thr Arg Tyr Met Leu
           90                  95                 100 ctc tac ggc gac cga gtg gac agc tgg aca ccg ttc tac cag cga ggg       571
Leu Tyr Gly Asp Arg Val Asp Ser Trp Thr Pro Phe Tyr Gln Arg Gly
       105                 110                 115
```

-continued

```
cac aac tcg acc ttc ttt ggt aac gtg aac gag tcg gcg gtg gtg cgc      619
His Asn Ser Thr Phe Phe Gly Asn Val Asn Glu Ser Ala Val Val Arg
    120                 125                 130 cat gac ctg cac ttc cac ttc act gcg cgc tac atc cgc atc gtg ccc      667
His Asp Leu His Phe His Phe Thr Ala Arg Tyr Ile Arg Ile Val Pro
135                 140                 145                 150 ctg gcc tgg aac cca cgc ggc aag atc ggc ctg agg ctc ggc ctc tat      715
Leu Ala Trp Asn Pro Arg Gly Lys Ile Gly Leu Arg Leu Gly Leu Tyr
                    155                 160                 165 ggc tgc cca tac aag gcc gac ata ctc tat ttc gac ggc gac gat gcc      763
Gly Cys Pro Tyr Lys Ala Asp Ile Leu Tyr Phe Asp Gly Asp Asp Ala
                170                 175                 180 atc tcc tac cgc ttc ccg cga ggg gtc agc cga agc ctg tgg gac gtg      811
Ile Ser Tyr Arg Phe Pro Arg Gly Val Ser Arg Ser Leu Trp Asp Val
            185                 190                 195 ttc gcc ttc agc ttc aag acc gag gag aag gac ggt ctt ctg ctg cac      859
Phe Ala Phe Ser Phe Lys Thr Glu Glu Lys Asp Gly Leu Leu Leu His
        200                 205                 210 gcc gag ggc gcc cag ggc gac tac gtg acg ctc gag ctg gag ggg gca      907
Ala Glu Gly Ala Gln Gly Asp Tyr Val Thr Leu Glu Leu Glu Gly Ala
215                 220                 225                 230 cac ctg ctg ctg cac atg agc ctg ggc agc agc cct atc cag cca aga      955
His Leu Leu Leu His Met Ser Leu Gly Ser Ser Pro Ile Gln Pro Arg
                    235                 240                 245 cca ggt cac acc acc gtg agc gca ggc gga gtc ctc aat gac cag cac     1003
Pro Gly His Thr Thr Val Ser Ala Gly Gly Val Leu Asn Asp Gln His
                250                 255                 260 tgg cac tat gtg cgg gtg gac cga ttt ggc cgc gat gta aat ttc acc     1051
Trp His Tyr Val Arg Val Asp Arg Phe Gly Arg Asp Val Asn Phe Thr
            265                 270                 275 ctg gac ggc tat gtg cag cgc ttt att ctc aat gga gac ttc gag agg     1099
Leu Asp Gly Tyr Val Gln Arg Phe Ile Leu Asn Gly Asp Phe Glu Arg
        280                 285                 290 ctg aac ctg gac act gag atg ttc atc gga ggt ctg gtg ggc gcc gcg     1147
Leu Asn Leu Asp Thr Glu Met Phe Ile Gly Gly Leu Val Gly Ala Ala
295                 300                 305                 310 cgg aag aac ctg gcc tat cgg cat aac ttc cgc ggc tgc ata gaa aac     1195
Arg Lys Asn Leu Ala Tyr Arg His Asn Phe Arg Gly Cys Ile Glu Asn
                    315                 320                 325 gta atc ttc aac cgc gtc aac atc gca gac ctg gcc gtg cgg cgc cat     1243
Val Ile Phe Asn Arg Val Asn Ile Ala Asp Leu Ala Val Arg Arg His
                330                 335                 340 tcc cgg atc acc ttc gag ggt aag gtg gct ttt cgt tgc ctg gac ccg     1291
Ser Arg Ile Thr Phe Glu Gly Lys Val Ala Phe Arg Cys Leu Asp Pro
            345                 350                 355 gta ccg cac cct atc aac ttc gga ggc cct cac aac ttc gtt caa gtg     1339
Val Pro His Pro Ile Asn Phe Gly Gly Pro His Asn Phe Val Gln Val
        360                 365                 370 ccc ggt ttc cca cgc cgt ggc cgc ctg gca gtc tca ttt cgc ttc cgc     1387
Pro Gly Phe Pro Arg Arg Gly Arg Leu Ala Val Ser Phe Arg Phe Arg
375                 380                 385                 390 acc tgg gac ctc acc ggg ctt ctc ctt ttc tcc cgt ctg ggg gac ggg     1435
Thr Trp Asp Leu Thr Gly Leu Leu Leu Phe Ser Arg Leu Gly Asp Gly
                    395                 400                 405 ctg ggc cac gtg gag ctg acg ctc agc gaa ggg cag gtc aac gtg tcc     1483
Leu Gly His Val Glu Leu Thr Leu Ser Glu Gly Gln Val Asn Val Ser
                410                 415                 420 atc gcg cag agc ggc cga aag aag ctt cag ttc gct gct ggg tac cga     1531
Ile Ala Gln Ser Gly Arg Lys Lys Leu Gln Phe Ala Ala Gly Tyr Arg
```

-continued

```
              425                 430                 435
ctg aat gac ggc ttt tgg cac gag gtg aat ttt gtg gca cag gaa aac      1579
Leu Asn Asp Gly Phe Trp His Glu Val Asn Phe Val Ala Gln Glu Asn
    440                 445                 450 cat gca gtt atc agc att gat gat gtg gaa ggg gca gag gtc agg gtc      1627
His Ala Val Ile Ser Ile Asp Asp Val Glu Gly Ala Glu Val Arg Val
455                 460                 465                 470 tca tac ccg ttg ctg atc cgg aca ggg acc tca tat ttc ttt ggg ggt      1675
Ser Tyr Pro Leu Leu Ile Arg Thr Gly Thr Ser Tyr Phe Phe Gly Gly
                475                 480                 485 tgt ccc aag cca gcc agt cga tgg gac tgc cac tcc aac cag acg gca      1723
Cys Pro Lys Pro Ala Ser Arg Trp Asp Cys His Ser Asn Gln Thr Ala
            490                 495                 500 ttc cat ggc tgc atg gag ctg ctc aag gtg gat ggt caa ctg gtc aac      1771
Phe His Gly Cys Met Glu Leu Leu Lys Val Asp Gly Gln Leu Val Asn
        505                 510                 515 ctg act ctg gtg gag ggc cgg cgg ctt gga ttc tat gct gag gtc ctc      1819
Leu Thr Leu Val Glu Gly Arg Arg Leu Gly Phe Tyr Ala Glu Val Leu
    520                 525                 530 ttt gat aca tgt ggc atc act gat agg tgc agc cct aac atg tgt gag      1867
Phe Asp Thr Cys Gly Ile Thr Asp Arg Cys Ser Pro Asn Met Cys Glu
535                 540                 545                 550 cat gat gga cgc tgc tac cag tct tgg gat gac ttc att tgc tac tgc      1915
His Asp Gly Arg Cys Tyr Gln Ser Trp Asp Asp Phe Ile Cys Tyr Cys
                555                 560                 565 gaa ctg acg ggc tac aag gga gag acc tgc cac aca cct ttg tat aag      1963
Glu Leu Thr Gly Tyr Lys Gly Glu Thr Cys His Thr Pro Leu Tyr Lys
            570                 575                 580 gaa tcc tgt gag gct tat cgg ctc agt ggg aaa act tct gga aac ttc      2011
Glu Ser Cys Glu Ala Tyr Arg Leu Ser Gly Lys Thr Ser Gly Asn Phe
        585                 590                 595 acc att gat cct gat ggc agt ggc ccc ctg aag cca ttt gta gtg tac      2059
Thr Ile Asp Pro Asp Gly Ser Gly Pro Leu Lys Pro Phe Val Val Tyr
    600                 605                 610 tgt gat atc cga gag aac cga gcg tgg aca gtt gtg cgg cat gac agg      2107
Cys Asp Ile Arg Glu Asn Arg Ala Trp Thr Val Val Arg His Asp Arg
615                 620                 625                 630 ctg tgg aca act cga gtg aca ggt ccc agc atg gag cgg cca ttc ctg      2155
Leu Trp Thr Thr Arg Val Thr Gly Ser Ser Met Glu Arg Pro Phe Leu
                635                 640                 645 ggg gct atc cag tac tgg aat gca tcc tgg gag gaa gtc agt gcc ctt      2203
Gly Ala Ile Gln Tyr Trp Asn Ala Ser Trp Glu Glu Val Ser Ala Leu
            650                 655                 660 gcc aat gct tcc cag cat tgt gaa cag tgg atc gag ttc tcc tgc tac      2251
Ala Asn Ala Ser Gln His Cys Glu Gln Trp Ile Glu Phe Ser Cys Tyr
        665                 670                 675 aat tcc cgg ctc ctc aac act gca gga ggc tac ccc tac agc ttt tgg      2299
Asn Ser Arg Leu Leu Asn Thr Ala Gly Gly Tyr Pro Tyr Ser Phe Trp
    680                 685                 690 att ggc cga aat gag gag cag cac ttc tac tgg gga ggc tcc cag cct      2347
Ile Gly Arg Asn Glu Glu Gln His Phe Tyr Trp Gly Gly Ser Gln Pro
695                 700                 705                 710 ggg atc cag cgc tgt gcc tgt ggt ctg gac cgg agc tgt gtg gac cct      2395
Gly Ile Gln Arg Cys Ala Cys Gly Leu Asp Arg Ser Cys Val Asp Pro
                715                 720                 725 gcc ttg tac tgc aac tgt gac gct gac cag ccc cag tgg aga act gac      2443
Ala Leu Tyr Cys Asn Cys Asp Ala Asp Gln Pro Gln Trp Arg Thr Asp
            730                 735                 740 aag gga ctg ctg acc ttt gtg gac cat ctg cct gtc act cag gta gtg      2491
```

```
Lys Gly Leu Leu Thr Phe Val Asp His Leu Pro Val Thr Gln Val Val
        745                 750                 755 ata ggg gat acg aac cgc tcc act tct gag gcc cag ttc ttc ctg agg    2539
Ile Gly Asp Thr Asn Arg Ser Thr Ser Glu Ala Gln Phe Phe Leu Arg
760                 765                 770 cct ctg cgc tgc tat ggc gat cga aat tcc tgg aac acc att tcc ttc    2587
Pro Leu Arg Cys Tyr Gly Asp Arg Asn Ser Trp Asn Thr Ile Ser Phe
775                 780                 785                 790 cac acc ggg gct gca cta cgc ttc ccc cca atc cgt gcc aac cac agc    2635
His Thr Gly Ala Ala Leu Arg Phe Pro Pro Ile Arg Ala Asn His Ser
                795                 800                 805 ctg gat gtc tcc ttc tac ttc agg acc tct gct ccc tcg ggg gtc ttc    2683
Leu Asp Val Ser Phe Tyr Phe Arg Thr Ser Ala Pro Ser Gly Val Phe
            810                 815                 820 cta gag aat atg ggg ggc cct tac tgc cag tgg cgc gac cct tat gtg    2731
Leu Glu Asn Met Gly Gly Pro Tyr Cys Gln Trp Arg Arg Pro Tyr Val
        825                 830                 835 cgg gtg gaa ctc aac aca tcc cgg gat gtg gtc ttc gcc ttt gat gtg    2779
Arg Val Glu Leu Asn Thr Ser Arg Asp Val Val Phe Ala Phe Asp Val
840                 845                 850 ggg aat ggg gat gag aac ctc aca gta cac tca gac gac ttt gag ttc    2827
Gly Asn Gly Asp Glu Asn Leu Thr Val His Ser Asp Asp Phe Glu Phe
855                 860                 865                 870 aat gat gac gag tgg cac ctg gtc cgg gct gaa atc aac gtg aag cag    2875
Asn Asp Asp Glu Trp His Leu Val Arg Ala Glu Ile Asn Val Lys Gln
                875                 880                 885 gcc cgg ctc cga gtg gat cac cgg ccc tgg gtt ctg cgg cct atg cca    2923
Ala Arg Leu Arg Val Asp His Arg Pro Trp Val Leu Arg Pro Met Pro
            890                 895                 900 ctg cag acc tac atc tgg atg gag tat gac cag ccc ctc tat gtg gga    2971
Leu Gln Thr Tyr Ile Trp Met Glu Tyr Asp Gln Pro Leu Tyr Val Gly
        905                 910                 915 tct gca gag ctt aag aga cgc ccc ttt gtg ggt tgc ttg agg gcc atg    3019
Ser Ala Glu Leu Lys Arg Arg Pro Phe Val Gly Cys Leu Arg Ala Met
920                 925                 930 cgt ctg aac gga gtg act ctg aac ctg gag ggc cgt gcc aat gcc tct    3067
Arg Leu Asn Gly Val Thr Leu Asn Leu Glu Gly Arg Ala Asn Ala Ser
935                 940                 945                 950 gag ggt acc tca ccc aac tgc aca ggc cac tgt gcc cac cct cgg ctc    3115
Glu Gly Thr Ser Pro Asn Cys Thr Gly His Cys Ala His Pro Arg Leu
                955                 960                 965 ccc tgt ttc cat gga ggc cgc tgc gtg gag cgc tat agc tac tac acg    3163
Pro Cys Phe His Gly Gly Arg Cys Val Glu Arg Tyr Ser Tyr Tyr Thr
            970                 975                 980 tgt gac tgt gac ctc acg gct ttt gat ggg cca tac tgc aac cac gat    3211
Cys Asp Cys Asp Leu Thr Ala Phe Asp Gly Pro Tyr Cys Asn His Asp
        985                 990                 995 att ggt ggt ttc ttt gag ccg ggc acc tgg atg cgc tat aac cta cag    3259
Ile Gly Gly Phe Phe Glu Pro Gly Thr Trp Met Arg Tyr Asn Leu Gln
1000                1005                1010 tca gcg ctg cgc tct gca gcc agg gag ttc tcc cac atg ctg agc cgg    3307
Ser Ala Leu Arg Ser Ala Ala Arg Glu Phe Ser His Met Leu Ser Arg
1015                1020                1025                1030 cca gtg cca ggc tat gag cct ggc tac atc ccg ggc tat gat act ccg    3355
Pro Val Pro Gly Tyr Glu Pro Gly Tyr Ile Pro Gly Tyr Asp Thr Pro
                1035                1040                1045 ggc tat gtg cct ggc tac cat ggc ccc ggg tac cgc ctg ccc gac tac    3403
Gly Tyr Val Pro Gly Tyr His Gly Pro Gly Tyr Arg Leu Pro Asp Tyr
            1050                1055                1060
```

```
ccc cgg cct ggt cgg cct gtg ccc ggt tac cgt ggg cct gtc tac aac    3451
Pro Arg Pro Gly Arg Pro Val Pro Gly Tyr Arg Gly Pro Val Tyr Asn
        1065                1070                1075 gtt acg gga gag gag gtc tcc ttc agc ttc agc acc agc tcc gcc cct    3499
Val Thr Gly Glu Glu Val Ser Phe Ser Phe Ser Thr Ser Ser Ala Pro
    1080                1085                1090 gct gtc ctg ctc tac gtc agt tcc ttt gtt cgt gac tac atg gct gtg    3547
Ala Val Leu Leu Tyr Val Ser Ser Phe Val Arg Asp Tyr Met Ala Val
1095                1100                1105                1110 ctc atc aag gat gat ggg acc ctt cag ctg cga tat cag ctg ggc acc    3595
Leu Ile Lys Asp Asp Gly Thr Leu Gln Leu Arg Tyr Gln Leu Gly Thr
            1115                1120                1125 agt ccc tac gtg tac cag cta acc act cga cca gtg acc gat ggc cag    3643
Ser Pro Tyr Val Tyr Gln Leu Thr Thr Arg Pro Val Thr Asp Gly Gln
        1130                1135                1140 ccc cat agc atc aat atc acc cgt gtt tac cgg aac ctc ttc atc cag    3691
Pro His Ser Ile Asn Ile Thr Arg Val Tyr Arg Asn Leu Phe Ile Gln
    1145                1150                1155 gtg gac tac ttc cca ctg aca gag cag aag ttc tcg ctg ttg gtg gac    3739
Val Asp Tyr Phe Pro Leu Thr Glu Gln Lys Phe Ser Leu Leu Val Asp
1160                1165                1170 agc cag ttg gac tca ccc aag gcc ttg tat tta ggg cgt gtg atg gag    3787
Ser Gln Leu Asp Ser Pro Lys Ala Leu Tyr Leu Gly Arg Val Met Glu
1175                1180                1185                1190 aca gga gtc att gac ccg gag atc cag cgc tac aac acc cca ggt ttc    3835
Thr Gly Val Ile Asp Pro Glu Ile Gln Arg Tyr Asn Thr Pro Gly Phe
            1195                1200                1205 tca ggc tgc ctg tct ggt gtt cga ttc aac aac gtg gct ccc ctc aag    3883
Ser Gly Cys Leu Ser Gly Val Arg Phe Asn Asn Val Ala Pro Leu Lys
        1210                1215                1220 acc cac ttc cga acc cct cga ccc atg act gct gag cta gct gag gcc    3931
Thr His Phe Arg Thr Pro Arg Pro Met Thr Ala Glu Leu Ala Glu Ala
    1225                1230                1235 ctt cga gtt cag gga gaa ctg tcc gaa tct aat tgc gga gct atg cca    3979
Leu Arg Val Gln Gly Glu Leu Ser Glu Ser Asn Cys Gly Ala Met Pro
1240                1245                1250 cgt ctt gtt tca gag gtg cca cct gag ctt gat ccc tgg tat ctg ccc    4027
Arg Leu Val Ser Glu Val Pro Pro Glu Leu Asp Pro Trp Tyr Leu Pro
1255                1260                1265                1270 cca gac ttc ccc tac tac cat gat gaa gga tgg gtt gcc ata ctt tta    4075
Pro Asp Phe Pro Tyr Tyr His Asp Glu Gly Trp Val Ala Ile Leu Leu
            1275                1280                1285 ggc ttt ttg gtg gcc ttt ctg ctg ctg ggg ctg gtg gga atg ttg gtg    4123
Gly Phe Leu Val Ala Phe Leu Leu Leu Gly Leu Val Gly Met Leu Val
        1290                1295                1300 ctc ttc tat ctg caa aat cat cgc tat aag ggc tcc tac cat acc aat    4171
Leu Phe Tyr Leu Gln Asn His Arg Tyr Lys Gly Ser Tyr His Thr Asn
    1305                1310                1315 gag ccc aag gct gcc cac gag tac cat cct ggc agc aaa cct ccc cta    4219
Glu Pro Lys Ala Ala His Glu Tyr His Pro Gly Ser Lys Pro Pro Leu
1320                1325                1330 ccc act tca ggc cct gcc cag gtc ccc acc cct aca gca gct ccc aac    4267
Pro Thr Ser Gly Pro Ala Gln Val Pro Thr Pro Thr Ala Ala Pro Asn
1335                1340                1345                1350 caa gct cca gcc tca gcc cca gcc cca gcc cca act cca gcc cca gcc    4315
Gln Ala Pro Ala Ser Ala Pro Ala Pro Ala Pro Thr Pro Ala Pro Ala
            1355                1360                1365 cct ggc ccc cgg gat cag aac cta ccc cag atc ctg gag gag tcc agg    4363
Pro Gly Pro Arg Asp Gln Asn Leu Pro Gln Ile Leu Glu Glu Ser Arg
        1370                1375                1380
```

-continued

```
tct gaa tgagtcagaa gggcttctgg gaccaattcc agctcctgac attcccccag    4419
Ser Glu tsrgcctgcc tctcccccat cctatcaggg acatttggct cttagctggc tctgctcatc    4479
cagaggatat tcccccatcc ccccccatc aagtttggtg ggcagagcta cagatgggac    4539
ccaagggagt ggccgagcct cactgcctaa accaatgccc ttctcatccc tgtttcccca    4599
ggctcctggc tgtttatctg ccccaaagga gaagcctcat ggggttgaca taggtccttt    4659
ctgccatctc tgttccagct gctgtcaggg attaacaaca gagtgtaggg gagattaact    4719
gcctcccttc caatagacac tatcagcagg gacagatgtg tgggagtgca gggctgcaga    4779
gggtatgggg ggaggaggct gctaaaccct atcccccagc ctcccccctg ccctgaagat    4839
cttccatttg cttccactca gctggaggct caagagggct tgatggctgt ccctgcccc    4899 cctcctttg ttttgtacac agagaccaag aggcctcagt ttagcacctt agtacctccg    4959
ctgcttcact tgctttagcc aaagccataa aaaacctgca acgtagagaa ataatgcag    5019 atacccctgac tagccagccc tctactcctc caacctttc caagatatgc aatggccttt    5079
gtgcctgccc aaaggcttcg ccccctccag tgcatgagga accctcttc ctccgctcag    5139 agatgctgct tcatttaccc aggaggtcat attctttata tatatttttt gttgcaaagt    5199
gtctctctag agaaactcta tatattattc gaattttaa attatttgtt tatatataaa    5259
agaaaagctc aattggcaaa aaaaaaaaaa aaaaa    5294
```

<210> SEQ ID NO 2
<211> LENGTH: 1384
<212> TYPE: PRT
<213> ORGANISM: Homo sapiens

<400> SEQUENCE: 2

```
Met Met His Leu Arg Leu Phe Cys Ile Leu Leu Ala Ala Val Ser Gly
 1               5                  10                  15

Ala Glu Gly Trp Gly Tyr Tyr Gly Cys Asp Glu Glu Leu Val Gly Pro
            20                  25                  30

Leu Tyr Ala Arg Ser Leu Gly Ala Ser Ser Tyr Tyr Ser Leu Leu Thr
        35                  40                  45

Ala Pro Arg Phe Ala Arg Leu His Gly Ile Ser Gly Trp Ser Pro Arg
    50                  55                  60

Ile Gly Asp Pro Asn Pro Trp Leu Gln Ile Asp Leu Met Lys Lys His
65                  70                  75                  80

Arg Ile Arg Ala Val Ala Thr Gln Gly Ser Phe Asn Ser Trp Asp Trp
                85                  90                  95

Val Thr Arg Tyr Met Leu Leu Tyr Gly Asp Arg Val Asp Ser Trp Thr
            100                 105                 110

Pro Phe Tyr Gln Arg Gly His Asn Ser Thr Phe Gly Asn Val Asn
        115                 120                 125

Glu Ser Ala Val Val Arg His Asp Leu His Phe His Phe Thr Ala Arg
    130                 135                 140

Tyr Ile Arg Ile Val Pro Leu Ala Trp Asn Pro Arg Gly Lys Ile Gly
145                 150                 155                 160

Leu Arg Leu Gly Leu Tyr Gly Cys Pro Tyr Lys Ala Asp Ile Leu Tyr
                165                 170                 175

Phe Asp Gly Asp Asp Ala Ile Ser Tyr Arg Phe Pro Arg Gly Val Ser
            180                 185                 190

Arg Ser Leu Trp Asp Val Phe Ala Phe Ser Phe Lys Thr Glu Glu Lys
```

-continued

```
            195                 200                 205
Asp Gly Leu Leu His Ala Glu Gly Ala Gln Gly Asp Tyr Val Thr
    210                 215                 220
Leu Glu Leu Glu Gly Ala His Leu Leu His Met Ser Leu Gly Ser
225                 230                 235                 240
Ser Pro Ile Gln Pro Arg Pro Gly His Thr Thr Val Ser Ala Gly Gly
                245                 250                 255
Val Leu Asn Asp Gln His Trp His Tyr Val Arg Val Asp Arg Phe Gly
                260                 265                 270
Arg Asp Val Asn Phe Thr Leu Asp Gly Tyr Val Gln Arg Phe Ile Leu
            275                 280                 285
Asn Gly Asp Phe Glu Arg Leu Asn Leu Asp Thr Glu Met Phe Ile Gly
            290                 295                 300
Gly Leu Val Gly Ala Ala Arg Lys Asn Leu Ala Tyr Arg His Asn Phe
305                 310                 315                 320
Arg Gly Cys Ile Glu Asn Val Ile Phe Asn Arg Val Asn Ile Ala Asp
                325                 330                 335
Leu Ala Val Arg Arg His Ser Arg Ile Thr Phe Glu Gly Lys Val Ala
            340                 345                 350
Phe Arg Cys Leu Asp Pro Val Pro His Pro Ile Asn Phe Gly Gly Pro
            355                 360                 365
His Asn Phe Val Gln Val Pro Gly Phe Pro Arg Arg Gly Arg Leu Ala
    370                 375                 380
Val Ser Phe Arg Phe Arg Thr Trp Asp Leu Thr Gly Leu Leu Leu Phe
385                 390                 395                 400
Ser Arg Leu Gly Asp Gly Leu Gly His Val Glu Leu Thr Leu Ser Glu
                405                 410                 415
Gly Gln Val Asn Val Ser Ile Ala Gln Ser Gly Arg Lys Lys Leu Gln
            420                 425                 430
Phe Ala Ala Gly Tyr Arg Leu Asn Asp Gly Phe Trp His Glu Val Asn
            435                 440                 445
Phe Val Ala Gln Glu Asn His Ala Val Ile Ser Ile Asp Asp Val Glu
    450                 455                 460
Gly Ala Glu Val Arg Val Ser Tyr Pro Leu Leu Ile Arg Thr Gly Thr
465                 470                 475                 480
Ser Tyr Phe Phe Gly Gly Cys Pro Lys Pro Ala Ser Arg Trp Asp Cys
                485                 490                 495
His Ser Asn Gln Thr Ala Phe His Gly Cys Met Glu Leu Leu Lys Val
                500                 505                 510
Asp Gly Gln Leu Val Asn Leu Thr Leu Val Glu Gly Arg Arg Leu Gly
            515                 520                 525
Phe Tyr Ala Glu Val Leu Phe Asp Thr Cys Gly Ile Thr Asp Arg Cys
            530                 535                 540
Ser Pro Asn Met Cys Glu His Asp Gly Arg Cys Tyr Gln Ser Trp Asp
545                 550                 555                 560
Asp Phe Ile Cys Tyr Cys Glu Leu Thr Gly Tyr Lys Gly Glu Thr Cys
                565                 570                 575
His Thr Pro Leu Tyr Lys Glu Ser Cys Glu Ala Tyr Arg Leu Ser Gly
                580                 585                 590
Lys Thr Ser Gly Asn Phe Thr Ile Asp Pro Asp Gly Ser Gly Pro Leu
            595                 600                 605
Lys Pro Phe Val Val Tyr Cys Asp Ile Arg Glu Asn Arg Ala Trp Thr
    610                 615                 620
```

```
Val Val Arg His Asp Arg Leu Trp Thr Thr Arg Val Thr Gly Ser Ser
625                 630                 635                 640

Met Glu Arg Pro Phe Leu Gly Ala Ile Gln Tyr Trp Asn Ala Ser Trp
            645                 650                 655

Glu Glu Val Ser Ala Leu Ala Asn Ala Ser Gln His Cys Glu Gln Trp
                660                 665                 670

Ile Glu Phe Ser Cys Tyr Asn Ser Arg Leu Leu Asn Thr Ala Gly Gly
            675                 680                 685

Tyr Pro Tyr Ser Phe Trp Ile Gly Arg Asn Glu Gln His Phe Tyr
690                 695                 700

Trp Gly Gly Ser Gln Pro Gly Ile Gln Arg Cys Ala Cys Gly Leu Asp
705                 710                 715                 720

Arg Ser Cys Val Asp Pro Ala Leu Tyr Cys Asn Cys Asp Ala Asp Gln
                725                 730                 735

Pro Gln Trp Arg Thr Asp Lys Gly Leu Leu Thr Phe Val Asp His Leu
            740                 745                 750

Pro Val Thr Gln Val Val Ile Gly Asp Thr Asn Arg Ser Thr Ser Glu
            755                 760                 765

Ala Gln Phe Phe Leu Arg Pro Leu Arg Cys Tyr Gly Asp Arg Asn Ser
770                 775                 780

Trp Asn Thr Ile Ser Phe His Thr Gly Ala Ala Leu Arg Phe Pro Pro
785                 790                 795                 800

Ile Arg Ala Asn His Ser Leu Asp Val Ser Phe Tyr Phe Arg Thr Ser
                805                 810                 815

Ala Pro Ser Gly Val Phe Leu Glu Asn Met Gly Gly Pro Tyr Cys Gln
            820                 825                 830

Trp Arg Arg Pro Tyr Val Arg Val Glu Leu Asn Thr Ser Arg Asp Val
            835                 840                 845

Val Phe Ala Phe Asp Val Gly Asn Gly Asp Glu Asn Leu Thr Val His
850                 855                 860

Ser Asp Asp Phe Glu Phe Asn Asp Asp Glu Trp His Leu Val Arg Ala
865                 870                 875                 880

Glu Ile Asn Val Lys Gln Ala Arg Leu Arg Val Asp His Arg Pro Trp
                885                 890                 895

Val Leu Arg Pro Met Pro Leu Gln Thr Tyr Ile Trp Met Glu Tyr Asp
            900                 905                 910

Gln Pro Leu Tyr Val Gly Ser Ala Glu Leu Lys Arg Arg Pro Phe Val
            915                 920                 925

Gly Cys Leu Arg Ala Met Arg Leu Asn Gly Val Thr Leu Asn Leu Glu
930                 935                 940

Gly Arg Ala Asn Ala Ser Glu Gly Thr Ser Pro Asn Cys Thr Gly His
945                 950                 955                 960

Cys Ala His Pro Arg Leu Pro Cys Phe His Gly Arg Cys Val Glu
                965                 970                 975

Arg Tyr Ser Tyr Tyr Thr Cys Asp Cys Asp Leu Thr Ala Phe Asp Gly
            980                 985                 990

Pro Tyr Cys Asn His Asp Ile Gly Gly Phe Glu Pro Gly Thr Trp
995                 1000                1005

Met Arg Tyr Asn Leu Gln Ser Ala Leu Arg Ser Ala Ala Arg Glu Phe
    1010                1015                1020

Ser His Met Leu Ser Arg Pro Val Pro Gly Tyr Glu Pro Gly Tyr Ile
1025                1030                1035                1040
```

-continued

```
Pro Gly Tyr Asp Thr Pro Gly Tyr Val Pro Gly Tyr His Gly Pro Gly
            1045                1050                1055
Tyr Arg Leu Pro Asp Tyr Pro Arg Pro Gly Arg Pro Val Pro Gly Tyr
        1060                1065                1070
Arg Gly Pro Val Tyr Asn Val Thr Gly Glu Glu Val Ser Phe Ser Phe
    1075                1080                1085
Ser Thr Ser Ser Ala Pro Ala Val Leu Leu Tyr Val Ser Phe Val
1090                1095                1100
Arg Asp Tyr Met Ala Val Leu Ile Lys Asp Asp Gly Thr Leu Gln Leu
1105                1110                1115                1120
Arg Tyr Gln Leu Gly Thr Ser Pro Tyr Val Tyr Gln Leu Thr Thr Arg
            1125                1130                1135
Pro Val Thr Asp Gly Gln Pro His Ser Ile Asn Ile Thr Arg Val Tyr
            1140                1145                1150
Arg Asn Leu Phe Ile Gln Val Asp Tyr Phe Pro Leu Thr Glu Gln Lys
            1155                1160                1165
Phe Ser Leu Leu Val Asp Ser Gln Leu Asp Ser Pro Lys Ala Leu Tyr
        1170                1175                1180
Leu Gly Arg Val Met Glu Thr Gly Val Ile Asp Pro Glu Ile Gln Arg
1185                1190                1195                1200
Tyr Asn Thr Pro Gly Phe Ser Gly Cys Leu Ser Gly Val Arg Phe Asn
            1205                1210                1215
Asn Val Ala Pro Leu Lys Thr His Phe Arg Thr Pro Arg Pro Met Thr
        1220                1225                1230
Ala Glu Leu Ala Glu Ala Leu Arg Val Gln Gly Glu Leu Ser Glu Ser
            1235                1240                1245
Asn Cys Gly Ala Met Pro Arg Leu Val Ser Glu Val Pro Pro Glu Leu
    1250                1255                1260
Asp Pro Trp Tyr Leu Pro Pro Asp Phe Pro Tyr Tyr His Asp Glu Gly
1265                1270                1275                1280
Trp Val Ala Ile Leu Leu Gly Phe Leu Val Ala Phe Leu Leu Gly
            1285                1290                1295
Leu Val Gly Met Leu Val Leu Phe Tyr Leu Gln Asn His Arg Tyr Lys
            1300                1305                1310
Gly Ser Tyr His Thr Asn Glu Pro Lys Ala Ala His Gly Tyr His Pro
            1315                1320                1325
Gly Ser Lys Pro Pro Leu Pro Thr Ser Gly Pro Ala Gln Val Pro Thr
    1330                1335                1340
Pro Thr Ala Ala Pro Asn Gln Ala Pro Ala Ser Ala Pro Ala Pro Ala
1345                1350                1355                1360
Pro Thr Pro Ala Pro Ala Pro Gly Pro Arg Asp Gln Asn Leu Pro Gln
            1365                1370                1375
Ile Leu Glu Glu Ser Arg Ser Glu
            1380

<210> SEQ ID NO 3
<211> LENGTH: 5350
<212> TYPE: DNA
<213> ORGANISM: Rattus norvegicus
<220> FEATURE:
<221> NAME/KEY: CDS
<222> LOCATION: (154)..(4296)

<400> SEQUENCE: 3
gattttgact gggggtagga gaaagggaag ggtgggtgag gacggaaaaa gcagcatcgg     60
```

-continued

```
tcagccgcga acccccaggag aaaagctggg ggcctgagcc agaaccggag ccctagcggc      120
acaaggcaga cacccagggt tggtcagctc cgc atg atg agt ctc cgg ctt ttc      174
                                     Met Met Ser Leu Arg Leu Phe
                                       1               5 agc att ctg ctc gcc gct gtg gtc tct gga gcc cag ggc tgg ggc tac      222
Ser Ile Leu Leu Ala Ala Val Val Ser Gly Ala Gln Gly Trp Gly Tyr
         10                  15                  20 tat ggc tgc aat gag gag ctg gtg ggg cct ctg tat gca cgg tct ctg      270
Tyr Gly Cys Asn Glu Glu Leu Val Gly Pro Leu Tyr Ala Arg Ser Leu
 25                  30                  35 ggt gct tcc tcc tac tat gga ctc ttt acc aca gcc cgc ttt gcc cgg      318
Gly Ala Ser Ser Tyr Tyr Gly Leu Phe Thr Thr Ala Arg Phe Ala Arg
 40                  45                  50                  55 cta cac ggc atc agt gga tgg tcg ccc cgg att ggg gac ccg aat ccc      366
Leu His Gly Ile Ser Gly Trp Ser Pro Arg Ile Gly Asp Pro Asn Pro
                 60                  65                  70 tgg ctc cag ata gac tta atg aag aag cat cga atc cgg gct gtg gcc      414
Trp Leu Gln Ile Asp Leu Met Lys Lys His Arg Ile Arg Ala Val Ala
             75                  80                  85 aca cag gga gcc ttt aat tct tgg gat tgg gtc aca cgt tac atg ctg      462
Thr Gln Gly Ala Phe Asn Ser Trp Asp Trp Val Thr Arg Tyr Met Leu
         90                  95                 100 ctc tac ggg gac cgt gtg gac agc tgg aca cca ttc tac caa caa ggg      510
Leu Tyr Gly Asp Arg Val Asp Ser Trp Thr Pro Phe Tyr Gln Gln Gly
105                 110                 115 cac aac gcg acc ttc ttc ggt aat gtc aac gac tcg gcg gtg gta cgc      558
His Asn Ala Thr Phe Phe Gly Asn Val Asn Asp Ser Ala Val Val Arg
120                 125                 130                 135 cat gac ctg cac tac cat ttt acg gct cgc tac atc cgc atc gtg cca      606
His Asp Leu His Tyr His Phe Thr Ala Arg Tyr Ile Arg Ile Val Pro
                140                 145                 150 ctg gcc tgg aac ccc cgc ggc aag att ggc ttg agg ctg ggc atc tac      654
Leu Ala Trp Asn Pro Arg Gly Lys Ile Gly Leu Arg Leu Gly Ile Tyr
            155                 160                 165 ggt tgt ccc tac acg tcc aac atc ctg tat ttt gac ggc gat gat gcc      702
Gly Cys Pro Tyr Thr Ser Asn Ile Leu Tyr Phe Asp Gly Asp Asp Ala
        170                 175                 180 att tca tac cgc ttc cag cga ggg gcc agt caa agt ctt tgg gac gtg      750
Ile Ser Tyr Arg Phe Gln Arg Gly Ala Ser Gln Ser Leu Trp Asp Val
    185                 190                 195 ttc gct ttt agt ttc aag aca gag gag aag gac ggg ctg ctg ttg cac      798
Phe Ala Phe Ser Phe Lys Thr Glu Glu Lys Asp Gly Leu Leu Leu His
200                 205                 210                 215 acc gaa ggc tcc cag ggg gat tat gtg acg ctt gaa ctg caa gga gca      846
Thr Glu Gly Ser Gln Gly Asp Tyr Val Thr Leu Glu Leu Gln Gly Ala
                220                 225                 230 cac ctg ctg ctg cac atg agc ctg ggc agc agc ccc atc cag ccg aga      894
His Leu Leu Leu His Met Ser Leu Gly Ser Ser Pro Ile Gln Pro Arg
            235                 240                 245 cct ggt cac acc acg gtg agc gct ggt ggc gta ctt aat gac cta agc      942
Pro Gly His Thr Thr Val Ser Ala Gly Gly Val Leu Asn Asp Leu Ser
        250                 255                 260 tgg cat tat gtg cgg gtg gac cga tac ggc cga gaa gca aat ctc acc      990
Trp His Tyr Val Arg Val Asp Arg Tyr Gly Arg Glu Ala Asn Leu Thr
    265                 270                 275 ctg gat ggt tac gta cat cgc ttt gtg ctc aac ggc gac ttt gaa agg     1038
Leu Asp Gly Tyr Val His Arg Phe Val Leu Asn Gly Asp Phe Glu Arg
280                 285                 290                 295 ctg aat ctc gaa aat gag ata ttc atc gga ggt cta gtg ggc gca gcg     1086
```

-continued

| | | | | | | | | | | | | |
|---|---|---|---|---|---|---|---|---|---|---|---|---|
| Leu | Asn | Leu | Glu | Asn | Glu | Ile | Phe | Ile | Gly | Gly | Leu | Val | Gly | Ala | Ala |
| | | | 300 | | | | | 305 | | | | 310 | | | |

```
cgt aag aac ctg gcc tac cgc cat aac ttc cgt ggc tgt ata gaa aac      1134
Arg Lys Asn Leu Ala Tyr Arg His Asn Phe Arg Gly Cys Ile Glu Asn
            315                 320                 325 gtg atc tac aac cgg atc aac ata gct gaa atg gca gtg cag cgc cat      1182
Val Ile Tyr Asn Arg Ile Asn Ile Ala Glu Met Ala Val Gln Arg His
        330                 335                 340 tcg cgg atc acc ttc gag ggt aat gtg gct ttc cgg tgc ttg gat ccc      1230
Ser Arg Ile Thr Phe Glu Gly Asn Val Ala Phe Arg Cys Leu Asp Pro
    345                 350                 355 gtt cca cac ccc atc aac ttc gga ggc cct cac aac ttc gtc caa gtg      1278
Val Pro His Pro Ile Asn Phe Gly Gly Pro His Asn Phe Val Gln Val
360                 365                 370                 375 cct ggc ttt cca cgt cga ggc cgc ctt gct gtc tcc ttc cgc ttc cgc      1326
Pro Gly Phe Pro Arg Arg Gly Arg Leu Ala Val Ser Phe Arg Phe Arg
                380                 385                 390 acc tgg gac ctc aca ggg ctg ctc ctt ttc tcc cgc ttg ggg gat ggg      1374
Thr Trp Asp Leu Thr Gly Leu Leu Leu Phe Ser Arg Leu Gly Asp Gly
            395                 400                 405 ctg ggt cat gtg gag ctg atg ctt agt gaa ggg caa gtc aat gta tcc      1422
Leu Gly His Val Glu Leu Met Leu Ser Glu Gly Gln Val Asn Val Ser
        410                 415                 420 atc gcg cag act ggc cgc aag aag ctt cag ttt gct gcg ggg tac cgc      1470
Ile Ala Gln Thr Gly Arg Lys Lys Leu Gln Phe Ala Ala Gly Tyr Arg
    425                 430                 435 ctg aat gat ggc ttc tgg cat gag gtg aac ttt gtg gca cag gaa aac      1518
Leu Asn Asp Gly Phe Trp His Glu Val Asn Phe Val Ala Gln Glu Asn
440                 445                 450                 455 cat gcg gtc atc agt att gat gat gtg gag ggg gca gag gtc agg gta      1566
His Ala Val Ile Ser Ile Asp Asp Val Glu Gly Ala Glu Val Arg Val
                460                 465                 470 tca tac cca ctg ctg atc cgc aca ggg act tca tac ttc ttt ggt ggt      1614
Ser Tyr Pro Leu Leu Ile Arg Thr Gly Thr Ser Tyr Phe Phe Gly Gly
            475                 480                 485 tgt ccc aaa cca gcc agt cga tgg ggc tgc cac tcc aac cag aca gca      1662
Cys Pro Lys Pro Ala Ser Arg Trp Gly Cys His Ser Asn Gln Thr Ala
        490                 495                 500 ttc cat ggc tgc atg gag ctg ctc aag gtg gat ggt caa ctg gtc aac      1710
Phe His Gly Cys Met Glu Leu Leu Lys Val Asp Gly Gln Leu Val Asn
    505                 510                 515 ctc act ctg gta gag ttt cgg aag ctt ggt tac ttt gct gag gtc ctc      1758
Leu Thr Leu Val Glu Phe Arg Lys Leu Gly Tyr Phe Ala Glu Val Leu
520                 525                 530                 535 ttt gac aca tgt ggc atc aca gac aga tgc agc cct aat atg tgt gag      1806
Phe Asp Thr Cys Gly Ile Thr Asp Arg Cys Ser Pro Asn Met Cys Glu
                540                 545                 550 cat gat ggg cgc tgc tac cag tct tgg gat gac ttc atc tgc tac tgc      1854
His Asp Gly Arg Cys Tyr Gln Ser Trp Asp Asp Phe Ile Cys Tyr Cys
            555                 560                 565 gaa ctc acc ggc tac aag gga gtt acc tgc cat gaa cca ttg tat aag      1902
Glu Leu Thr Gly Tyr Lys Gly Val Thr Cys His Glu Pro Leu Tyr Lys
        570                 575                 580 gag tcc tgt gaa gcc tat cgc ctc agc ggg aaa tat tct gga aat tac      1950
Glu Ser Cys Glu Ala Tyr Arg Leu Ser Gly Lys Tyr Ser Gly Asn Tyr
    585                 590                 595 acc att gat cct gat ggc agt gga ccc ctg aaa cca ttt gta gtg tat      1998
Thr Ile Asp Pro Asp Gly Ser Gly Pro Leu Lys Pro Phe Val Val Tyr
600                 605                 610                 615
```

-continued

| | |
|---|---|
| tgt gat atc cga gag aac cga gcg tgg aca gtt gtg cga cat gac agg<br>Cys Asp Ile Arg Glu Asn Arg Ala Trp Thr Val Val Arg His Asp Arg<br>620                       625                       630 | 2046 |
| cta tgg acc act cga gtg aca ggt tcc agc atg gac cgg ccc ttt ctg<br>Leu Trp Thr Thr Arg Val Thr Gly Ser Ser Met Asp Arg Pro Phe Leu<br>635                       640                       645 | 2094 |
| ggg gcc atc caa tac tgg aat gcc tcc tgg gag gaa gtc agt gct ctg<br>Gly Ala Ile Gln Tyr Trp Asn Ala Ser Trp Glu Glu Val Ser Ala Leu<br>650                       655                       660 | 2142 |
| gcc aat gct tcc cag cac tgt gag cag tgg atc gag ttc tcc tgc tac<br>Ala Asn Ala Ser Gln His Cys Glu Gln Trp Ile Glu Phe Ser Cys Tyr<br>665                       670                       675 | 2190 |
| aat tcc cgg ctg ctc aac act gca gga ggc tac ccc tac agc ttt tgg<br>Asn Ser Arg Leu Leu Asn Thr Ala Gly Gly Tyr Pro Tyr Ser Phe Trp<br>680                       685                       690                       695 | 2238 |
| att ggc cga aat gaa gaa cag cat ttc tac tgg gga ggc tcc cag cct<br>Ile Gly Arg Asn Glu Glu Gln His Phe Tyr Trp Gly Gly Ser Gln Pro<br>700                       705                       710 | 2286 |
| ggg atc caa cgc tgt gcc tgt ggg ctg gac cag agc tgt ata gac cct<br>Gly Ile Gln Arg Cys Ala Cys Gly Leu Asp Gln Ser Cys Ile Asp Pro<br>715                       720                       725 | 2334 |
| gca ctg cac tgc aac tgc gat gct gac cag cca cag tgg aga aca gac<br>Ala Leu His Cys Asn Cys Asp Ala Asp Gln Pro Gln Trp Arg Thr Asp<br>730                       735                       740 | 2382 |
| aag ggg ctc ctg acc ttt gtg gac cat ctg cct gtc act cag gta gtg<br>Lys Gly Leu Leu Thr Phe Val Asp His Leu Pro Val Thr Gln Val Val<br>745                       750                       755 | 2430 |
| ata ggt gac aca aac cgc tcc agc tct gaa gct cag ttc ttc ctg agg<br>Ile Gly Asp Thr Asn Arg Ser Ser Ser Glu Ala Gln Phe Phe Leu Arg<br>760                       765                       770                       775 | 2478 |
| cct ctg cgc tgt tat ggt gac cgc aat tcc tgg aac act atc tcc ttc<br>Pro Leu Arg Cys Tyr Gly Asp Arg Asn Ser Trp Asn Thr Ile Ser Phe<br>780                       785                       790 | 2526 |
| cgc act gga gct gca ctg cgt ttc cct cca atc cgt gcc aac cac agc<br>Arg Thr Gly Ala Ala Leu Arg Phe Pro Pro Ile Arg Ala Asn His Ser<br>795                       800                       805 | 2574 |
| ctt gat gtc tcc ttc tac ttc agg acc tcg gct ccc tca gga gtc ttc<br>Leu Asp Val Ser Phe Tyr Phe Arg Thr Ser Ala Pro Ser Gly Val Phe<br>810                       815                       820 | 2622 |
| cta gag aac atg ggg ggt cct ttc tgc cag tgg cgc cga cct tac gtg<br>Leu Glu Asn Met Gly Gly Pro Phe Cys Gln Trp Arg Arg Pro Tyr Val<br>825                       830                       835 | 2670 |
| aga gtg gag ctc aac aca tcc cgg gat gtg gtc ttt gcc ttt gat att<br>Arg Val Glu Leu Asn Thr Ser Arg Asp Val Val Phe Ala Phe Asp Ile<br>840                       845                       850                       855 | 2718 |
| ggc aat ggg gat gag aac ctg aca gtg cac tca gat gac ttc gag ttc<br>Gly Asn Gly Asp Glu Asn Leu Thr Val His Ser Asp Asp Phe Glu Phe<br>860                       865                       870 | 2766 |
| aat gat gac gag tgg cat ttg gtc cgg gct gaa atc aac gtg aag cag<br>Asn Asp Asp Glu Trp His Leu Val Arg Ala Glu Ile Asn Val Lys Gln<br>875                       880                       885 | 2814 |
| gcc cgg ctg cga gtg gac cat cgg ccc tgg gtg cta agg ccc atg ccc<br>Ala Arg Leu Arg Val Asp His Arg Pro Trp Val Leu Arg Pro Met Pro<br>890                       895                       900 | 2862 |
| ctg cag acg tac atc tgg ctg gag tat gac caa ccc ctc tat gtg gga<br>Leu Gln Thr Tyr Ile Trp Leu Glu Tyr Asp Gln Pro Leu Tyr Val Gly<br>905                       910                       915 | 2910 |
| tct gca gag ctt aag agg cgc cca ttt gtg ggg tgc ttg agg gcc atg<br>Ser Ala Glu Leu Lys Arg Arg Pro Phe Val Gly Cys Leu Arg Ala Met<br>920                       925                       930                       935 | 2958 |

-continued

```
cgt ttg aat gga gtg act ctg aac ttg gag ggt cgt gcc aat gcc tcc        3006
Arg Leu Asn Gly Val Thr Leu Asn Leu Glu Gly Arg Ala Asn Ala Ser
            940                 945                 950 gag ggc acc ttc ccc aac tgc acg ggc cac tgc acc cac ccc cgg ttc        3054
Glu Gly Thr Phe Pro Asn Cys Thr Gly His Cys Thr His Pro Arg Phe
            955                 960                 965 ccc tgt ttc cac gga gga cgc tgt gtg gag cga tac agc tac tac acg        3102
Pro Cys Phe His Gly Gly Arg Cys Val Glu Arg Tyr Ser Tyr Tyr Thr
            970                 975                 980 tgt gac tgt gac ctc aca gct ttt gat gga cca tat tgt aat cac gat        3150
Cys Asp Cys Asp Leu Thr Ala Phe Asp Gly Pro Tyr Cys Asn His Asp
985                 990                 995 att ggt gga ttc ttt gag act ggc aca tgg atg cgc tat aac ctc cag        3198
Ile Gly Gly Phe Phe Glu Thr Gly Thr Trp Met Arg Tyr Asn Leu Gln
1000                1005                1010                1015 tca gca ctg cgt tct gcg gcc cag gag ttc tct cac atg ctg agc cgg        3246
Ser Ala Leu Arg Ser Ala Ala Gln Glu Phe Ser His Met Leu Ser Arg
                1020                1025                1030 ccg gta ccg ggc tat gag cct ggc tat atc cca ggc tac gac act cct        3294
Pro Val Pro Gly Tyr Glu Pro Gly Tyr Ile Pro Gly Tyr Asp Thr Pro
                1035                1040                1045 ggt tac gtg cct ggg tac cat ggt cct ggg tac cgc cta ccc gac tac        3342
Gly Tyr Val Pro Gly Tyr His Gly Pro Gly Tyr Arg Leu Pro Asp Tyr
                1050                1055                1060 cca agg cct ggc cgg cca gtg ccc gga tac cgg ggg ccc gtg tac aat        3390
Pro Arg Pro Gly Arg Pro Val Pro Gly Tyr Arg Gly Pro Val Tyr Asn
1065                1070                1075 gtt act gga gag gag gtc tcc ttt agc ttc agc acc agc tct gct cct        3438
Val Thr Gly Glu Glu Val Ser Phe Ser Phe Ser Thr Ser Ser Ala Pro
1080                1085                1090                1095 gca gtc ctg ctc tac gtc agc tcc ttt gtg cgt gac tac atg gcc gtg        3486
Ala Val Leu Leu Tyr Val Ser Ser Phe Val Arg Asp Tyr Met Ala Val
                1100                1105                1110 ctc atc aag gaa gat ggg acc cta cag ctt cgc tat cag ctg ggc acc        3534
Leu Ile Lys Glu Asp Gly Thr Leu Gln Leu Arg Tyr Gln Leu Gly Thr
                1115                1120                1125 agt ccc tat gtg tac cag cta acc acc cgg cca gtg acc gat ggc caa        3582
Ser Pro Tyr Val Tyr Gln Leu Thr Thr Arg Pro Val Thr Asp Gly Gln
                1130                1135                1140 ccc cat agt gtc aac atc acc cgg gtc tac cga aac ctc ttt atc cag        3630
Pro His Ser Val Asn Ile Thr Arg Val Tyr Arg Asn Leu Phe Ile Gln
1145                1150                1155 gtg gac tac ttc ccg ctg aca gaa cag aag ttc tct ctc ctg gtg gac        3678
Val Asp Tyr Phe Pro Leu Thr Glu Gln Lys Phe Ser Leu Leu Val Asp
1160                1165                1170                1175 agc cag ctg gac tcc ccc aag gcc ttg tat cta ggg cgt gtg atg gag        3726
Ser Gln Leu Asp Ser Pro Lys Ala Leu Tyr Leu Gly Arg Val Met Glu
                1180                1185                1190 aca gga gtc att gac cca gag att cag cgg tac aac acc cca ggt ttc        3774
Thr Gly Val Ile Asp Pro Glu Ile Gln Arg Tyr Asn Thr Pro Gly Phe
                1195                1200                1205 tca ggc tgc ctg tct ggt gtc cgg ttc aac aat gtg gct cct ctc aag        3822
Ser Gly Cys Leu Ser Gly Val Arg Phe Asn Asn Val Ala Pro Leu Lys
1210                1215                1220 acc cat ttc cga acc cct cgc ccc atg act gct gag ctg gcg gag gcc        3870
Thr His Phe Arg Thr Pro Arg Pro Met Thr Ala Glu Leu Ala Glu Ala
                1225                1230                1235 atg cgg gtt caa gga gaa ctg tcg gag tct aac tgt ggc gct atg cca        3918
Met Arg Val Gln Gly Glu Leu Ser Glu Ser Asn Cys Gly Ala Met Pro
```

| | |
|---|---|
| 1240 1245 1250 1255 | |
| cgc ctt gtc tcc gag gtg cca cca gag ctt gat ccc tgg tac ctg ccc<br>Arg Leu Val Ser Glu Val Pro Pro Glu Leu Asp Pro Trp Tyr Leu Pro<br>1260 1265 1270 | 3966 |
| cca gat ttc cca tac tac cat gac gac gga tgg att gcc ata ctc tta<br>Pro Asp Phe Pro Tyr Tyr His Asp Asp Gly Trp Ile Ala Ile Leu Leu<br>1275 1280 1285 | 4014 |
| ggt ttt ttg gtg gcc ttc ctg ctg ctg ggg ctt gtg gga atg ctg gtg<br>Gly Phe Leu Val Ala Phe Leu Leu Leu Gly Leu Val Gly Met Leu Val<br>1290 1295 1300 | 4062 |
| ctg ttc tat ctg caa aat cat cga tac aag ggc tcc tat cac acc aac<br>Leu Phe Tyr Leu Gln Asn His Arg Tyr Lys Gly Ser Tyr His Thr Asn<br>1305 1310 1315 | 4110 |
| gag ccc aag gcc acc cat gat tcc cac cct ggc ggc aaa gct ccc cta<br>Glu Pro Lys Ala Thr His Asp Ser His Pro Gly Gly Lys Ala Pro Leu<br>1320 1325 1330 1335 | 4158 |
| cct ccc tca ggc cct gcc cag gcc cct gcc ccc act cca gct ccc acc<br>Pro Pro Ser Gly Pro Ala Gln Ala Pro Ala Pro Thr Pro Ala Pro Thr<br>1340 1345 1350 | 4206 |
| cag gtt ccg acc cca gcc cca gcc cca gcc tct ggc cca ggc ccc agg<br>Gln Val Pro Thr Pro Ala Pro Ala Pro Ala Ser Gly Pro Gly Pro Arg<br>1355 1360 1365 | 4254 |
| gac cag aac ctc ccc cag atc ttg gag gag tcc agg tct gaa<br>Asp Gln Asn Leu Pro Gln Ile Leu Glu Glu Ser Arg Ser Glu<br>1370 1375 1380 | 4296 |
| tgagtcacaa gggcttcagg gaccaaggcc aactcctcta agtcccttca gctcctgcct | 4356 |
| ctcctctccc ctgtcaggga catttggctc ttcttagcag gctctgttca ccaggaggat | 4416 |
| cccctcttgc caagtttggt gtgcagagct acagatggga ccaaagggag tggccgagtc | 4476 |
| tcactgccta aaccaatgcc ctgcccccac ccccaccc agctcctggc tgtttgcctg | 4536 |
| ccctacggga gaaagctcat ggagctgagg cgggcctttc ctgccatctc tgtcccagct | 4596 |
| gctggcaagg attaacaacc aagggcaggg gaggtgaact gcctcccttc ctgtgggtat | 4656 |
| tatcagcagg gacagatgtg ggggatcgag gggctgcaca gggcaggcag ggagggaggg | 4716 |
| aggaggctgc taaaacacac cctggagcct ccccctgcc ctgctgaccg gctgtcttcc | 4776 |
| atctgcttcc tctcagctgg ggttgaggga agaacttcat ccccaccccc cacctcaccc | 4836 |
| aaccctttt gttcttacag agaccaagag gcctcagctt agcactttag tacctccact | 4896 |
| gcttcacatg ctttagccaa agccataaaa agcctgcaag tagaagaaat aatgcagacc | 4956 |
| ctgcccagcc agtcctctgc tcctccaccc cttttccaaaa tacgcaatag cctggggtgc | 5016 |
| ctgtgtgcag gcctggcccc tgcgtgcatg aggagcccct cccgctcaga gatgctgcga | 5076 |
| gttcgtccag gaggtcatat tctttatata tatttttgt tgcaaagcct ctctctagag | 5136 |
| aactatatat tactctaatt ttttaattat ctgtttatat ataaaagaac tcagtgggcc | 5196 |
| gtcctgtgct gtgcccagtt tgtagtgagc tccttctgtt ggatgtctca tgagtcctgc | 5256 |
| cagccactca cccgcctgcc gggcctccat tctagagcag gcagagcccg ctgtgccctc | 5316 |
| acctgagcag gttcaataaa agcagagtgg caga | 5350 |

<210> SEQ ID NO 4
<211> LENGTH: 1381
<212> TYPE: PRT
<213> ORGANISM: Rattus norvegicus

<400> SEQUENCE: 4

Met Met Ser Leu Arg Leu Phe Ser Ile Leu Leu Ala Ala Val Val Ser

-continued

```
  1               5                    10                   15
Gly Ala Gln Gly Trp Gly Tyr Tyr Gly Cys Asn Glu Leu Val Gly
             20                  25                  30

Pro Leu Tyr Ala Arg Ser Leu Gly Ala Ser Tyr Tyr Gly Leu Phe
             35                  40                  45

Thr Thr Ala Arg Phe Ala Arg Leu His Gly Ile Ser Gly Trp Ser Pro
 50                  55                  60

Arg Ile Gly Asp Pro Asn Pro Trp Leu Gln Ile Asp Leu Met Lys Lys
 65                  70                  75                  80

His Arg Ile Arg Ala Val Ala Thr Gln Gly Ala Phe Asn Ser Trp Asp
                 85                  90                  95

Trp Val Thr Arg Tyr Met Leu Leu Tyr Gly Asp Arg Val Asp Ser Trp
             100                 105                 110

Thr Pro Phe Tyr Gln Gln Gly His Asn Ala Thr Phe Phe Gly Asn Val
             115                 120                 125

Asn Asp Ser Ala Val Val Arg His Asp Leu His Tyr His Phe Thr Ala
130                 135                 140

Arg Tyr Ile Arg Ile Val Pro Leu Ala Trp Asn Pro Arg Gly Lys Ile
145                 150                 155                 160

Gly Leu Arg Leu Gly Ile Tyr Gly Cys Pro Tyr Thr Ser Asn Ile Leu
                165                 170                 175

Tyr Phe Asp Gly Asp Asp Ala Ile Ser Tyr Arg Phe Gln Arg Gly Ala
                180                 185                 190

Ser Gln Ser Leu Trp Asp Val Phe Ala Phe Ser Phe Lys Thr Glu Glu
            195                 200                 205

Lys Asp Gly Leu Leu His Thr Glu Gly Ser Gln Gly Asp Tyr Val
210                 215                 220

Thr Leu Glu Leu Gln Gly Ala His Leu Leu His Met Ser Leu Gly
225                 230                 235                 240

Ser Ser Pro Ile Gln Pro Arg Pro Gly His Thr Thr Val Ser Ala Gly
            245                 250                 255

Gly Val Leu Asn Asp Leu Ser Trp His Tyr Val Arg Val Asp Arg Tyr
            260                 265                 270

Gly Arg Glu Ala Asn Leu Thr Leu Asp Gly Tyr Val His Arg Phe Val
            275                 280                 285

Leu Asn Gly Asp Phe Glu Arg Leu Asn Leu Glu Asn Glu Ile Phe Ile
290                 295                 300

Gly Gly Leu Val Gly Ala Ala Arg Lys Asn Leu Ala Tyr Arg His Asn
305                 310                 315                 320

Phe Arg Gly Cys Ile Glu Asn Val Ile Tyr Asn Arg Ile Asn Ile Ala
            325                 330                 335

Glu Met Ala Val Gln Arg His Ser Arg Ile Thr Phe Glu Gly Asn Val
            340                 345                 350

Ala Phe Arg Cys Leu Asp Pro Val Pro His Pro Ile Asn Phe Gly Gly
            355                 360                 365

Pro His Asn Phe Val Gln Val Pro Gly Phe Pro Arg Arg Gly Arg Leu
            370                 375                 380

Ala Val Ser Phe Arg Phe Arg Thr Trp Asp Leu Thr Gly Leu Leu Leu
385                 390                 395                 400

Phe Ser Arg Leu Gly Asp Gly Leu Gly His Val Glu Leu Met Leu Ser
                405                 410                 415

Glu Gly Gln Val Asn Val Ser Ile Ala Gln Thr Gly Arg Lys Lys Leu
            420                 425                 430
```

-continued

```
Gln Phe Ala Ala Gly Tyr Arg Leu Asn Asp Gly Phe Trp His Glu Val
        435                 440                 445
Asn Phe Val Ala Gln Glu Asn His Ala Val Ile Ser Ile Asp Asp Val
    450                 455                 460
Glu Gly Ala Glu Val Arg Val Ser Tyr Pro Leu Leu Ile Arg Thr Gly
465                 470                 475                 480
Thr Ser Tyr Phe Phe Gly Gly Cys Pro Lys Pro Ala Ser Arg Trp Gly
                485                 490                 495
Cys His Ser Asn Gln Thr Ala Phe His Gly Cys Met Glu Leu Leu Lys
            500                 505                 510
Val Asp Gly Gln Leu Val Asn Leu Thr Leu Val Glu Phe Arg Lys Leu
        515                 520                 525
Gly Tyr Phe Ala Glu Val Leu Phe Asp Thr Cys Gly Ile Thr Asp Arg
    530                 535                 540
Cys Ser Pro Asn Met Cys Glu His Asp Gly Arg Cys Tyr Gln Ser Trp
545                 550                 555                 560
Asp Asp Phe Ile Cys Tyr Cys Glu Leu Thr Gly Tyr Lys Gly Val Thr
                565                 570                 575
Cys His Glu Pro Leu Tyr Lys Glu Ser Cys Glu Ala Tyr Arg Leu Ser
            580                 585                 590
Gly Lys Tyr Ser Gly Asn Tyr Thr Ile Asp Pro Asp Gly Ser Gly Pro
        595                 600                 605
Leu Lys Pro Phe Val Val Tyr Cys Asp Ile Arg Glu Asn Arg Ala Trp
    610                 615                 620
Thr Val Val Arg His Asp Arg Leu Trp Thr Thr Arg Val Thr Gly Ser
625                 630                 635                 640
Ser Met Asp Arg Pro Phe Leu Gly Ala Ile Gln Tyr Trp Asn Ala Ser
                645                 650                 655
Trp Glu Glu Val Ser Ala Leu Ala Asn Ala Ser Gln His Cys Glu Gln
            660                 665                 670
Trp Ile Glu Phe Ser Cys Tyr Asn Ser Arg Leu Leu Asn Thr Ala Gly
        675                 680                 685
Gly Tyr Pro Tyr Ser Phe Trp Ile Gly Arg Asn Glu Glu Gln His Phe
    690                 695                 700
Tyr Trp Gly Ser Gln Pro Gly Ile Gln Arg Cys Ala Cys Gly Leu
705                 710                 715                 720
Asp Gln Ser Cys Ile Asp Pro Ala Leu His Cys Asn Cys Asp Ala Asp
                725                 730                 735
Gln Pro Gln Trp Arg Thr Asp Lys Gly Leu Leu Thr Phe Val Asp His
            740                 745                 750
Leu Pro Val Thr Gln Val Val Ile Gly Asp Thr Asn Arg Ser Ser Ser
        755                 760                 765
Glu Ala Gln Phe Phe Leu Arg Pro Leu Arg Cys Tyr Gly Asp Arg Asn
    770                 775                 780
Ser Trp Asn Thr Ile Ser Phe Arg Thr Gly Ala Ala Leu Arg Phe Pro
785                 790                 795                 800
Pro Ile Arg Ala Asn His Ser Leu Asp Val Ser Phe Tyr Phe Arg Thr
                805                 810                 815
Ser Ala Pro Ser Gly Val Phe Leu Glu Asn Met Gly Gly Pro Phe Cys
            820                 825                 830
Gln Trp Arg Arg Pro Tyr Val Arg Val Glu Leu Asn Thr Ser Arg Asp
        835                 840                 845
```

-continued

```
Val Val Phe Ala Phe Asp Ile Gly Asn Gly Asp Glu Asn Leu Thr Val
    850                 855                 860

His Ser Asp Asp Phe Glu Phe Asn Asp Asp Glu Trp His Leu Val Arg
865                 870                 875                 880

Ala Glu Ile Asn Val Lys Gln Ala Arg Leu Arg Val Asp His Arg Pro
                885                 890                 895

Trp Val Leu Arg Pro Met Pro Leu Gln Thr Tyr Ile Trp Leu Glu Tyr
            900                 905                 910

Asp Gln Pro Leu Tyr Val Gly Ser Ala Glu Leu Lys Arg Arg Pro Phe
            915                 920                 925

Val Gly Cys Leu Arg Ala Met Arg Leu Asn Gly Val Thr Leu Asn Leu
            930                 935                 940

Glu Gly Arg Ala Asn Ala Ser Glu Gly Thr Phe Pro Asn Cys Thr Gly
945                 950                 955                 960

His Cys Thr His Pro Arg Phe Pro Cys Phe His Gly Arg Cys Val
                965                 970                 975

Glu Arg Tyr Ser Tyr Tyr Thr Cys Asp Cys Asp Leu Thr Ala Phe Asp
            980                 985                 990

Gly Pro Tyr Cys Asn His Asp Ile Gly Gly Phe Phe Glu Thr Gly Thr
            995                 1000                1005

Trp Met Arg Tyr Asn Leu Gln Ser Ala Leu Arg Ser Ala Ala Gln Glu
    1010                1015                1020

Phe Ser His Met Leu Ser Arg Pro Val Pro Gly Tyr Glu Pro Gly Tyr
1025                1030                1035                1040

Ile Pro Gly Tyr Asp Thr Pro Gly Tyr Val Pro Gly Tyr His Gly Pro
                1045                1050                1055

Gly Tyr Arg Leu Pro Asp Tyr Pro Arg Pro Gly Arg Pro Val Pro Gly
                1060                1065                1070

Tyr Arg Gly Pro Val Tyr Asn Val Thr Gly Glu Glu Val Ser Phe Ser
                1075                1080                1085

Phe Ser Thr Ser Ser Ala Pro Ala Val Leu Leu Tyr Val Ser Ser Phe
    1090                1095                1100

Val Arg Asp Tyr Met Ala Val Leu Ile Lys Glu Asp Gly Thr Leu Gln
1105                1110                1115                1120

Leu Arg Tyr Gln Leu Gly Thr Ser Pro Tyr Val Tyr Gln Leu Thr Thr
            1125                1130                1135

Arg Pro Val Thr Asp Gly Gln Pro His Ser Val Asn Ile Thr Arg Val
                1140                1145                1150

Tyr Arg Asn Leu Phe Ile Gln Val Asp Tyr Phe Pro Leu Thr Glu Gln
            1155                1160                1165

Lys Phe Ser Leu Leu Val Asp Ser Gln Leu Asp Ser Pro Lys Ala Leu
    1170                1175                1180

Tyr Leu Gly Arg Val Met Glu Thr Gly Val Ile Asp Pro Glu Ile Gln
1185                1190                1195                1200

Arg Tyr Asn Thr Pro Gly Phe Ser Gly Cys Leu Ser Gly Val Arg Phe
                1205                1210                1215

Asn Asn Val Ala Pro Leu Lys Thr His Phe Arg Thr Pro Arg Pro Met
                1220                1225                1230

Thr Ala Glu Leu Ala Glu Ala Met Arg Val Gln Gly Glu Leu Ser Glu
            1235                1240                1245

Ser Asn Cys Gly Ala Met Pro Arg Leu Val Ser Glu Val Pro Pro Glu
    1250                1255                1260

Leu Asp Pro Trp Tyr Leu Pro Pro Asp Phe Pro Tyr Tyr His Asp Asp
```

-continued

```
                1265                1270                1275                1280
Gly Trp Ile Ala Ile Leu Leu Gly Phe Leu Val Ala Phe Leu Leu Leu
                    1285                1290                1295
Gly Leu Val Gly Met Leu Val Leu Phe Tyr Leu Gln Asn His Arg Tyr
                1300                1305                1310
Lys Gly Ser Tyr His Thr Asn Glu Pro Lys Ala Thr His Asp Ser His
            1315                1320                1325
Pro Gly Gly Lys Ala Pro Leu Pro Pro Ser Gly Pro Ala Gln Ala Pro
        1330                1335                1340
Ala Pro Thr Pro Ala Pro Thr Gln Val Pro Thr Pro Ala Pro Ala Pro
1345                1350                1355                1360
Ala Ser Gly Pro Gly Pro Arg Asp Gln Asn Leu Pro Gln Ile Leu Glu
                1365                1370                1375
Glu Ser Arg Ser Glu
            1380
```

<210> SEQ ID NO 5
<211> LENGTH: 4152
<212> TYPE: DNA
<213> ORGANISM: Homo sapiens

<400> SEQUENCE: 5

```
atgatgcatc tccggctctt ctgcatcctg ctcgccgcgg tctcaggagc cgagggctgg      60
ggctactacg gctgcgacga ggagctggtg ggtccctgt atgcacgctc cctgggcgcc      120
tcctcctact acagtctcct tactgcgccg cgattcgcca ggctgcacgg cataagcggg     180
tggtcaccac ggattgggga tccgaatccc tggctccaga tagacttaat gaagaagcac     240
cggatccggg ccgtggccac acagggctcc tttaattctt gggactgggt cacacgttac     300
atgctactct acggcgaccg agtggacagc tggacaccgt ctaccagcg agggcacaac      360
tcgaccttct ttggtaacgt gaacgagtcg gcggtggtgc gccatgacct gcacttccac     420
ttcactgcgc gctacatccg catcgtgccc tggcctgga acccacgcgg caagatcggc      480
ctgaggctcg gcctctatgg ctgcccatac aaggccgaca tactctattt cgacggcgac     540
gatgccatct cctaccgctt cccgcgaggg gtcagccgaa gctgtgggac gtgttcgcc      600
ttcagcttca agaccgagga aaggacggt cttctgctgc acgccgaggg cgcccagggc      660
gactacgtga cgctcgagct ggaggggca cacctgctgc tgcacatgag cctgggcagc     720
agccctatcc agccaagacc aggtcacacc accgtgagcg caggcggagt cctcaatgac     780
cagcactggc actatgtgcg ggtggaccga tttggccgcg atgtaaattt cacccctgga     840
ggctatgtgc agcgctttat tctcaatgga gacttcgaga ggctgaacct ggacactgag     900
atgttcatcg aggtctggt gggcgccgcg cggaagaacc tggcctatcg cataacttc      960
cgcggctgca tagaaaacgt aatcttcaac gcgtcaaca tcgcagacct ggccgtgcgg    1020
cgccattccc ggatcacctt cgagggtaag gtggcttttc gttgcctgga cccggtaccg    1080
cacctatca acttcggagg ccctcacaac ttcgttcaag tgcccggttt ccacgccgt      1140
ggccgcctgg cagtctcatt tcgcttccgc acctgggacc tcaccgggct tctccttttc    1200
tcccgtctgg gggacgggct gggccacgtg gagctgacgc tcagcgaagg gcaggtcaac    1260
gtgtccatcg cgcagagcgg ccgaaagaag cttcagttcg ctgctgggta ccgactgaat    1320
gacggctttt ggcacgaggt gaatttttgtg gcacaggaaa accatgcagt tatcagcatt    1380
gatgatgtgg aagggcaga ggtcagggtc tcatacccgt tgctgatccg gacagggacc    1440
```

-continued

```
tcatatttct ttgggggttg tcccaagcca gccagtcgat gggactgcca ctccaaccag    1500
acggcattcc atggctgcat ggagctgctc aaggtggatg gtcaactggt caacctgact    1560
ctggtggagg gccggcggct tggattctat gctgaggtcc tctttgatac atgtggcatc    1620
actgataggt gcagccctaa catgtgtgag catgatggac gctgctacca gtcttgggat    1680
gacttcattt gctactgcga actgacgggc tacaagggag agacctgcca cacacctttg    1740
tataaggaat cctgtgaggc ttatcggctc agtgggaaaa cttctggaaa cttcaccatt    1800
gatcctgatg gcagtggccc cctgaagcca tttgtagtgt actgtgatat ccgagagaac    1860
cgagcgtgga cagttgtgcg gcatgacagg ctgtggacaa ctcgagtgac aggttccagc    1920
atggagcggc cattcctggg ggctatccag tactggaatg catcctggga ggaagtcagt    1980
gcccttgcca atgcttccca gcattgtgaa cagtggatcg agttctcctg ctacaattcc    2040
cggctgctca acactgcagg aggctacccc tacagctttt ggattggccg aaatgaggag    2100
cagcacttct actggggagg ctcccagcct gggatccagc gctgtgcctg tggtctggac    2160
cggagctgtg tggaccctgc cttgtactgc aactgtgacg ctgaccagcc ccagtggaga    2220
actgacaagg gactgctgac ctttgtggac catctgcctg tcactcaggt agtgataggg    2280
gatacgaacc gctccacttc tgaggcccag ttcttcctga ggcctctgcg ctgctatggc    2340
gatcgaaatt cctggaacac catttccttc cacaccgggg ctgcactacg cttcccccca    2400
atccgtgcca accacagcct ggatgtctcc ttctacttca ggacctctgc tccctcgggg    2460
gtcttcctag agaatatggg gggcccttac tgccagtggc gccgacctta tgtgcgggtg    2520
gaactcaaca catcccggga tgtggtcttc gcctttgatg tggggaatgg ggatgagaac    2580
ctcacagtac actcagacga ctttgagttc aatgatgacg agtggcacct ggtccgggct    2640
gaaatcaacg tgaagcaggc ccggctccga gtggatcacc ggccctgggt tctgcggcct    2700
atgccactgc agacctacat ctggatggag tatgaccagc ccctctatgt gggatctgca    2760
gagcttaaga gacgcccctt tgtgggttgc ttgagggcca tgcgtctgaa cggagtgact    2820
ctgaacctgg agggccgtgc caatgcctct gagggtacct cacccaactg cacaggccac    2880
tgtgcccacc ctcggctccc ctgtttccat ggaggccgct gcgtggagcg ctatagctac    2940
tacacgtgtg actgtgacct cacggctttt gatgggccat actgcaacca cgatattggt    3000
ggtttctttg agccgggcac ctggatgcgc tataacctac agtcagcgct gcgctctgca    3060
gccagggagt ctccccacat gctgagccgg ccagtgccag gctatgagcc tggctacatc    3120
ccgggctatg atactccggg ctatgtgcct ggctaccatg gccccgggta ccgcctgccc    3180
gactaccccc ggcctggtcg gcctgtgccc ggttaccgtg ggcctgtcta caacgttacg    3240
ggagaggagg tctccttcag cttcagcacc agctccgccc ctgctgtcct gctctacgtc    3300
agttcctttg ttcgtgacta catggctgtg ctcatcaagg atgatgggac ccttcagctg    3360
cgatatcagc tgggcaccag tccctacgtg taccagctaa ccactcgacc agtgaccgat    3420
ggccagcccc atagcatcaa tatcacccgt gtttaccgga acctcttcat ccaggtggac    3480
tacttcccac tgacagagca gaagttctcg ctgttggtgg acagccagtt ggactcaccc    3540
aaggccttgt atttagggcg tgtgatggag acaggagtca ttgacccgga gatccagcgc    3600
tacaacaccc caggtttctc aggctgcctg tctggtgttc gattcaacaa cgtggctccc    3660
ctcaagaccc acttccgaac ccctcgaccc atgactgctg agctagctga ggcccttcga    3720
gttcagggag aactgtccga atctaattgc ggagctatgc cacgtcttgt ttcagaggtg    3780
ccacctgagc ttgatccctg gtatctgccc ccagacttcc cctactacca tgatgaagga    3840
```

-continued

| | |
|---|---|
| tgggttgcca tactttttagg ctttttggtg gcctttctgc tgctggggct ggtgggaatg | 3900 |
| ttggtgctct tctatctgca aaatcatcgc tataagggct cctaccatac caatgagccc | 3960 |
| aaggctgccc acgagtacca tcctggcagc aaacctcccc tacccacttc aggccctgcc | 4020 |
| caggtcccca cccctacagc agctcccaac caagctccag cctcagcccc agcccagcc | 4080 |
| ccaactccag ccccagcccc tggcccccgg gatcagaacc tacccagat cctggaggag | 4140 |
| tccaggtctg aa | 4152 |

<210> SEQ ID NO 6
<211> LENGTH: 4143
<212> TYPE: DNA
<213> ORGANISM: Rattus norvegicus

<400> SEQUENCE: 6

| | |
|---|---|
| atgatgagtc tccggctttt cagcattctg ctcgccgctg tggtctctgg agcccagggc | 60 |
| tggggctact atggctgcaa tgaggagctg gtggggcctc tgtatgcacg gtctctgggt | 120 |
| gcttcctcct actatggact ctttaccaca gcccgctttg cccggctaca cggcatcagt | 180 |
| ggatggtcgc cccggattgg ggacccgaat ccctggctcc agatagactt aatgaagaag | 240 |
| catcgaatcc gggctgtggc cacacaggga gcctttaatt cttgggattg ggtcacacgt | 300 |
| tacatgctgc tctacgggga ccgtgtggac agctggacac cattctacca caagggcac | 360 |
| aacgcgacct tcttcggtaa tgtcaacgac tcggcggtgg tacgccatga cctgcactac | 420 |
| cattttacgg ctcgctacat ccgcatcgtg ccactggcct ggaaccccg cggcaagatt | 480 |
| ggcttgaggc tgggcatcta cggttgtccc tacacgtcca acatcctgta ttttgacggc | 540 |
| gatgatgcca tttcataccg cttccagcga ggggccagtc aaagtctttg gacgtgttc | 600 |
| gcttttagtt tcaagacaga ggagaaggac gggctgctgt tgcacaccga aggctcccag | 660 |
| ggggattatg tgacgcttga actgcaagga gcacacctgc tgctgcacat gagcctgggc | 720 |
| agcagcccca tccagccgag acctggtcac accacggtga cgctggtgg cgtacttaat | 780 |
| gacctaagct ggcattatgt gcgggtggac cgatacggcc gagaagcaaa tctcacccctg | 840 |
| gatggttacg tacatcgctt tgtgctcaac ggcgactttg aaaggctgaa tctcgaaaat | 900 |
| gagatattca tcggaggtct agtgggcgca gcgcgtaaga acctggccta ccgccataac | 960 |
| ttccgtggct gtatagaaaa cgtgatctac aaccggatca acatagctga atggcagtg | 1020 |
| cagcgccatt cgcggatcac cttcgagggt aatgtggctt ccggtgctt ggatcccgtt | 1080 |
| ccacacccca tcaacttcgg aggccctcac aacttcgtcc aagtgcctgg ctttccacgt | 1140 |
| cgaggccgcc ttgctgtctc cttccgcttc cgcacctggg acctcacagg gctgctcctt | 1200 |
| ttctcccgct tgggggatgg gctgggtcat gtggagctga tgcttagtga agggcaagtc | 1260 |
| aatgtatcca tcgcgcagac tggccgcaag aagcttcagt ttgctgcggg gtaccgcctg | 1320 |
| aatgatggct tctggcatga ggtgaacttt gtggcacagg aaaaccatgc ggtcatcagt | 1380 |
| attgatgatg tggagggggc agaggtcagg gtatcatacc cactgctgat ccgcacaggg | 1440 |
| acttcatact tctttggtgg ttgtcccaaa ccagccagtc gatgggctg ccactccaac | 1500 |
| cagacagcat tccatggctg catggagctg ctcaaggtgg atggtcaact ggtcaacctc | 1560 |
| actctggtag agtttcggaa gcttggttac tttgctgagg tcctctttga cacatgtggc | 1620 |
| atcacagaca gatgcagccc taatatgtgt gagcatgatg ggcgctgcta ccagtcttgg | 1680 |
| gatgacttca tctgctactg cgaactcacc ggctacaagg gagttacctg ccatgaacca | 1740 |

-continued

```
ttgtataagg agtcctgtga agcctatcgc ctcagcggga aatattctgg aaattacacc    1800
attgatcctg atggcagtgg accccctgaaa ccatttgtag tgtattgtga tatccgagag    1860
aaccgagcgt ggacagttgt gcgacatgac aaggctatgga ccactcgagt gacaggttcc    1920
agcatggacc ggccctttct gggggccatc aatactggaa atgcctcctg ggaggaagtc    1980
agtgctctgg ccaatgcttc ccagcactgt gagcagtgga tcgagttctc ctgctacaat    2040
tcccggctgc tcaacactgc aggaggctac ccctacagct tttggattgg ccgaaatgaa    2100
gaacagcatt tctactgggg aggctcccag cctgggatcc aacgctgtgc ctgtgggctg    2160
gaccagagct gtatagaccc tgcactgcac tgcaactgcg atgctgacca gccacagtgg    2220
agaacagaca aggggctcct gacctttgtg gaccatctgc ctgtcactca ggtagtgata    2280
ggtgacacaa accgctccag ctctgaagct cagttcttcc tgaggcctct gcgctgttat    2340
ggtgaccgca attcctggaa cactatctcc ttccgcactg gagctgcact gcgtttccct    2400
ccaatccgtg ccaaccacag ccttgatgtc tccttctact tcaggacctc ggctccctca    2460
ggagtcttcc tagagaacat ggggggtcct ttctgccagt ggcgccgacc ttacgtgaga    2520
gtggagctca acacatcccg ggatgtggtc tttgcctttg atattggcaa tggggatgag    2580
aacctgacag tgcactcaga tgacttcgag ttcaatgatg acgagtggca tttggtccgg    2640
gctgaaatca acgtgaagca ggcccggctg cgagtggacc atcggccctg ggtgctaagg    2700
cccatgcccc tgcagacgta catctggctg gagtatgacc aacccctcta tgtgggatct    2760
gcagagctta agaggcgccc atttgtgggg tgcttgaggg ccatgcgttt gaatggagtg    2820
actctgaact tggagggtcg tgccaatgcc tccgagggca ccttccccaa ctgcacgggc    2880
cactgcaccc accccggtt cccctgtttc cacggaggac gctgtgtgga gcgatacagc    2940
tactacacgt gtgactgtga cctcacagct tttgatggac catattgtaa tcacgatatt    3000
ggtggattct ttgagactgg cacatggatg cgctataacc tccagtcagc actgcgttct    3060
gcggcccagg agttctctca catgctgagc cggccggtac cgggctatga gcctggctat    3120
atcccaggct acgacactcc tggttacgtg cctgggtacc atggtcctgg gtaccgccta    3180
cccgactacc caaggcctgg ccggccagtg cccggatacc gggggcccgt gtacaatgtt    3240
actggagagg aggtctcctt tagcttcagc accagctctg ctcctgcagt cctgctctac    3300
gtcagctcct ttgtgcgtga ctacatggcc gtgctcatca aggaagatgg gaccctacag    3360
cttcgctatc agctgggcac cagtccctat gtgtaccagc taaccacccg gccagtgacc    3420
gatggccaac ccatagtgt caacatcacc cgggtctacc gaaacctctt tatccaggtg    3480
gactacttcc gctgacagga acagaagttc tctctcctgg tggacagcca gctggactcc    3540
cccaaggcct tgtatctagg gcgtgtgatg gagacaggag tcattgaccc agagattcag    3600
cggtacaaca ccccaggttt ctcaggctgc ctgtctggtg tccggttcaa caatgtggct    3660
cctctcaaga cccatttccg aaccccctcgc cccatgactg ctgagctggc ggaggccatg    3720
cgggttcaag gagaactgtc ggagtctaac tgtggcgcta tgccacgcct tgtctccgag    3780
gtgccaccag agcttgatcc ctggtacctg cccccagatt tcccatacta ccatgacgac    3840
ggatggattg ccatactctt aggtttttg gtggccttcc tgctgctggg gcttgtggga    3900
atgctggtgc tgttctatct gcaaaatcat cgatacaagg ctcctatca caccaacgag    3960
cccaaggcca cccatgattc ccaccctggc ggcaaagctc ccctacctcc ctcaggcccct    4020
gcccaggccc ctgccccac tccagctccc acccaggttc cgaccccagc ccagcccca    4080
gcctctggcc caggccccag ggaccagaac ctcccccaga tcttggagga gtccaggtct    4140
```

```
gaa                                                              4143
```

<210> SEQ ID NO 7
<211> LENGTH: 129
<212> TYPE: PRT
<213> ORGANISM: Homo sapiens

<400> SEQUENCE: 7

```
Ala Ser Ser Tyr Tyr Ser Leu Leu Thr Ala Pro Arg Phe Ala Arg Leu
 1               5                  10                  15

His Gly Ile Ser Gly Trp Ser Pro Arg Ile Gly Asp Pro Asn Pro Trp
            20                  25                  30

Leu Gln Ile Asp Leu Met Lys Lys His Arg Ile Arg Ala Val Ala Thr
        35                  40                  45

Gln Gly Ser Phe Asn Ser Trp Asp Trp Val Thr Arg Tyr Met Leu Leu
    50                  55                  60

Tyr Gly Asp Arg Val Asp Ser Trp Thr Pro Phe Tyr Gln Arg Gly His
 65                  70                  75                  80

Asn Ser Thr Phe Phe Gly Asn Val Asn Glu Ser Ala Val Val Arg His
                85                  90                  95

Asp Leu His Phe His Phe Thr Ala Arg Tyr Ile Arg Ile Val Pro Leu
            100                 105                 110

Ala Trp Asn Pro Arg Gly Lys Ile Gly Leu Arg Leu Gly Leu Tyr Gly
        115                 120                 125

Cys
```

<210> SEQ ID NO 8
<211> LENGTH: 132
<212> TYPE: PRT
<213> ORGANISM: Homo sapiens

<400> SEQUENCE: 8

```
Phe Ala Phe Ser Phe Lys Thr Glu Glu Lys Asp Gly Leu Leu Leu His
 1               5                  10                  15

Ala Glu Gly Ala Gln Gly Asp Tyr Val Thr Leu Glu Leu Glu Gly Ala
            20                  25                  30

His Leu Leu Leu His Met Ser Leu Gly Ser Ser Pro Ile Gln Pro Arg
        35                  40                  45

Pro Gly His Thr Thr Val Ser Ala Gly Gly Val Leu Asn Asp Gln His
    50                  55                  60

Trp His Tyr Val Arg Val Asp Arg Phe Gly Arg Asp Val Asn Phe Thr
 65                  70                  75                  80

Leu Asp Gly Tyr Val Gln Arg Phe Ile Leu Asn Gly Asp Phe Glu Arg
                85                  90                  95

Leu Asn Leu Asp Thr Glu Met Phe Ile Gly Gly Leu Val Gly Ala Ala
            100                 105                 110

Arg Lys Asn Leu Ala Tyr Arg His Asn Phe Arg Gly Cys Ile Glu Asn
        115                 120                 125

Val Ile Phe Asn
    130
```

<210> SEQ ID NO 9
<211> LENGTH: 125
<212> TYPE: PRT
<213> ORGANISM: Homo sapiens

<400> SEQUENCE: 9

```
Pro Ile Asn Phe Gly Gly Pro His Asn Phe Val Gln Val Pro Gly Phe
 1               5                  10                  15

Pro Arg Arg Gly Arg Leu Ala Val Ser Phe Arg Phe Arg Thr Trp Asp
                20                  25                  30

Leu Thr Gly Leu Leu Leu Phe Ser Arg Leu Gly Asp Gly Leu Gly His
            35                  40                  45

Val Glu Leu Thr Leu Ser Glu Gly Gln Val Asn Val Ser Ile Ala Gln
        50                  55                  60

Ser Gly Arg Lys Lys Leu Gln Phe Ala Ala Gly Tyr Arg Leu Asn Asp
 65                  70                  75                  80

Gly Phe Trp His Glu Val Asn Phe Val Ala Gln Glu Asn His Ala Val
                85                  90                  95

Ile Ser Ile Asp Asp Val Glu Gly Ala Glu Val Arg Val Ser Tyr Pro
                100                 105                 110

Leu Leu Ile Arg Thr Gly Thr Ser Tyr Phe Phe Gly Gly
            115                 120                 125

<210> SEQ ID NO 10
<211> LENGTH: 33
<212> TYPE: PRT
<213> ORGANISM: Homo sapiens

<400> SEQUENCE: 10

Cys Ser Pro Asn Met Cys Glu His Asp Gly Arg Cys Tyr Gln Ser Trp
 1               5                  10                  15

Asp Asp Phe Ile Cys Tyr Cys Glu Leu Thr Gly Tyr Lys Gly Glu Thr
                20                  25                  30

Cys

<210> SEQ ID NO 11
<211> LENGTH: 158
<212> TYPE: PRT
<213> ORGANISM: Homo sapiens

<400> SEQUENCE: 11

Lys Glu Ser Cys Glu Ala Tyr Arg Leu Ser Gly Lys Thr Ser Gly Asn
 1               5                  10                  15

Phe Thr Ile Asp Pro Asp Gly Ser Gly Pro Leu Lys Pro Phe Val Val
                20                  25                  30

Tyr Cys Asp Ile Arg Glu Asn Arg Ala Trp Thr Val Val Arg His Asp
            35                  40                  45

Arg Leu Trp Thr Thr Arg Val Thr Gly Ser Ser Met Glu Arg Pro Phe
        50                  55                  60

Leu Gly Ala Ile Gln Tyr Trp Asn Ala Ser Trp Glu Glu Val Ser Ala
 65                  70                  75                  80

Leu Ala Asn Ala Ser Gln His Cys Glu Gln Trp Ile Glu Phe Ser Cys
                85                  90                  95

Tyr Asn Ser Arg Leu Leu Asn Thr Ala Gly Gly Tyr Pro Tyr Ser Phe
                100                 105                 110

Trp Ile Gly Arg Asn Glu Glu Gln His Phe Tyr Trp Gly Gly Ser Gln
            115                 120                 125

Pro Gly Ile Gln Arg Cys Ala Cys Gly Leu Asp Arg Ser Cys Val Asp
        130                 135                 140

Pro Ala Leu Tyr Cys Asn Cys Asp Ala Asp Gln Pro Gln Trp
145                 150                 155
```

```
<210> SEQ ID NO 12
<211> LENGTH: 130
<212> TYPE: PRT
<213> ORGANISM: Homo sapiens

<400> SEQUENCE: 12

Val Ser Phe Tyr Phe Arg Thr Ser Ala Pro Ser Gly Val Phe Leu Glu
  1               5                  10                  15

Asn Met Gly Gly Pro Tyr Cys Gln Trp Arg Arg Pro Tyr Val Arg Val
             20                  25                  30

Glu Leu Asn Thr Ser Arg Asp Val Phe Ala Phe Asp Val Gly Asn
         35                  40                  45

Gly Asp Glu Asn Leu Thr Val His Ser Asp Asp Phe Glu Phe Asn Asp
 50                  55                  60

Asp Glu Trp His Leu Val Arg Ala Glu Ile Asn Val Lys Gln Ala Arg
 65                  70                  75                  80

Leu Arg Val Asp His Arg Pro Trp Val Leu Arg Pro Met Pro Leu Gln
                 85                  90                  95

Thr Tyr Ile Trp Met Glu Tyr Asp Gln Pro Leu Tyr Val Gly Ser Ala
            100                 105                 110

Glu Leu Lys Arg Arg Pro Phe Val Gly Cys Leu Arg Ala Met Arg Leu
        115                 120                 125

Asn Gly
    130

<210> SEQ ID NO 13
<211> LENGTH: 25
<212> TYPE: PRT
<213> ORGANISM: Homo sapiens

<400> SEQUENCE: 13

Cys Ala His Pro Arg Leu Pro Cys Phe His Gly Gly Arg Cys Val Glu
  1               5                  10                  15

Arg Tyr Ser Tyr Tyr Thr Cys Asp Cys
             20                  25

<210> SEQ ID NO 14
<211> LENGTH: 47
<212> TYPE: PRT
<213> ORGANISM: Homo sapiens

<400> SEQUENCE: 14

Pro Val Pro Gly Tyr Glu Pro Gly Tyr Ile Pro Gly Tyr Asp Thr Pro
  1               5                  10                  15

Gly Tyr Val Pro Gly Tyr His Gly Pro Gly Tyr Arg Leu Pro Asp Tyr
             20                  25                  30

Pro Arg Pro Gly Arg Pro Val Pro Gly Tyr Arg Gly Pro Val Tyr
         35                  40                  45

<210> SEQ ID NO 15
<211> LENGTH: 136
<212> TYPE: PRT
<213> ORGANISM: Homo sapiens

<400> SEQUENCE: 15

Glu Val Ser Phe Ser Phe Ser Thr Ser Ala Pro Ala Val Leu Leu
  1               5                  10                  15

Tyr Val Ser Ser Phe Val Arg Asp Tyr Met Ala Val Leu Ile Lys Asp
             20                  25                  30
```

-continued

```
Asp Gly Thr Leu Gln Leu Arg Tyr Gln Leu Gly Ser Pro Tyr Val
        35                  40                  45

Tyr Gln Leu Thr Thr Arg Pro Val Thr Asp Gly Gln Pro His Ser Ile
    50                  55                  60

Asn Ile Thr Arg Val Tyr Arg Asn Leu Phe Ile Gln Val Asp Tyr Phe
65                  70                  75                  80

Pro Leu Thr Glu Gln Lys Phe Ser Leu Leu Val Asp Ser Gln Leu Asp
                85                  90                  95

Ser Pro Lys Ala Leu Tyr Leu Gly Arg Val Met Glu Thr Gly Val Ile
            100                 105                 110

Asp Pro Glu Ile Gln Arg Tyr Asn Thr Pro Gly Phe Ser Gly Cys Leu
        115                 120                 125

Ser Gly Val Arg Phe Asn Asn Val
    130                 135

<210> SEQ ID NO 16
<211> LENGTH: 25
<212> TYPE: PRT
<213> ORGANISM: Homo sapiens

<400> SEQUENCE: 16

Val Ala Ile Leu Leu Gly Phe Leu Val Ala Phe Leu Leu Leu Gly Leu
1               5                   10                  15

Val Gly Met Leu Val Leu Phe Tyr Leu
            20                  25

<210> SEQ ID NO 17
<211> LENGTH: 42
<212> TYPE: PRT
<213> ORGANISM: Homo sapiens

<400> SEQUENCE: 17

Pro Gly Ser Lys Pro Pro Leu Pro Thr Ser Gly Pro Ala Gln Val Pro
1               5                   10                  15

Thr Pro Thr Ala Ala Pro Asn Gln Ala Pro Ala Ser Ala Pro Ala Pro
            20                  25                  30

Ala Pro Thr Pro Ala Pro Ala Pro Gly Pro
        35                  40

<210> SEQ ID NO 18
<211> LENGTH: 129
<212> TYPE: PRT
<213> ORGANISM: Rattus norvegicus

<400> SEQUENCE: 18

Ala Ser Ser Tyr Tyr Gly Leu Phe Thr Thr Ala Arg Phe Ala Arg Leu
1               5                   10                  15

His Gly Ile Ser Gly Trp Ser Pro Arg Ile Gly Asp Pro Asn Pro Trp
            20                  25                  30

Leu Gln Ile Asp Leu Met Lys Lys His Arg Ile Arg Ala Val Ala Thr
        35                  40                  45

Gln Gly Ala Phe Asn Ser Trp Asp Trp Val Thr Arg Tyr Met Leu Leu
    50                  55                  60

Tyr Gly Asp Arg Val Asp Ser Trp Thr Pro Phe Tyr Gln Gln Gly His
65                  70                  75                  80

Asn Ala Thr Phe Phe Gly Asn Val Asn Asp Ser Ala Val Val Arg His
                85                  90                  95
```

-continued

```
Asp Leu His Tyr His Phe Thr Ala Arg Tyr Ile Arg Ile Val Pro Leu
            100                 105                 110
Ala Trp Asn Pro Arg Gly Lys Ile Gly Leu Arg Leu Gly Ile Tyr Gly
        115                 120                 125
Cys

<210> SEQ ID NO 19
<211> LENGTH: 132
<212> TYPE: PRT
<213> ORGANISM: Rattus norvegicus

<400> SEQUENCE: 19

Phe Ala Phe Ser Phe Lys Thr Glu Glu Lys Asp Gly Leu Leu Leu His
  1               5                  10                  15
Thr Glu Gly Ser Gln Gly Asp Tyr Val Thr Leu Glu Leu Gln Gly Ala
             20                  25                  30
His Leu Leu His Met Ser Leu Gly Ser Ser Pro Ile Gln Pro Arg
         35                  40                  45
Pro Gly His Thr Thr Val Ser Ala Gly Gly Val Leu Asn Asp Leu Ser
     50                  55                  60
Trp His Tyr Val Arg Val Asp Arg Tyr Gly Arg Glu Ala Asn Leu Thr
 65                  70                  75                  80
Leu Asp Gly Tyr Val His Arg Phe Val Leu Asn Gly Asp Phe Glu Arg
                 85                  90                  95
Leu Asn Leu Glu Asn Glu Ile Phe Ile Gly Gly Leu Val Gly Ala Ala
            100                 105                 110
Arg Lys Asn Leu Ala Tyr Arg His Asn Phe Arg Gly Cys Ile Glu Asn
        115                 120                 125
Val Ile Tyr Asn
        130

<210> SEQ ID NO 20
<211> LENGTH: 125
<212> TYPE: PRT
<213> ORGANISM: Rattus norvegicus

<400> SEQUENCE: 20

Pro Ile Asn Phe Gly Gly Pro His Asn Phe Val Gln Val Pro Gly Phe
  1               5                  10                  15
Pro Arg Arg Gly Arg Leu Ala Val Ser Phe Arg Phe Arg Thr Trp Asp
             20                  25                  30
Leu Thr Gly Leu Leu Leu Phe Ser Arg Leu Gly Asp Gly Leu Gly His
         35                  40                  45
Val Glu Leu Met Leu Ser Glu Gly Gln Val Asn Val Ser Ile Ala Gln
 50                  55                  60
Thr Gly Arg Lys Lys Leu Gln Phe Ala Ala Gly Tyr Arg Leu Asn Asp
 65                  70                  75                  80
Gly Phe Trp His Glu Val Asn Phe Val Ala Gln Glu Asn His Ala Val
                 85                  90                  95
Ile Ser Ile Asp Asp Val Glu Gly Ala Glu Val Arg Val Ser Tyr Pro
            100                 105                 110
Leu Leu Ile Arg Thr Gly Thr Ser Tyr Phe Phe Gly Gly
        115                 120                 125

<210> SEQ ID NO 21
<211> LENGTH: 33
<212> TYPE: PRT
```

```
<213> ORGANISM: Rattus norvegicus

<400> SEQUENCE: 21

Cys Ser Pro Asn Met Cys Glu His Asp Gly Arg Cys Tyr Gln Ser Trp
 1               5                  10                  15

Asp Asp Phe Ile Cys Tyr Cys Glu Leu Thr Gly Tyr Lys Gly Val Thr
                20                  25                  30

Cys

<210> SEQ ID NO 22
<211> LENGTH: 158
<212> TYPE: PRT
<213> ORGANISM: Rattus norvegicus

<400> SEQUENCE: 22

Lys Glu Ser Cys Glu Ala Tyr Arg Leu Ser Gly Lys Tyr Ser Gly Asn
 1               5                  10                  15

Tyr Thr Ile Asp Pro Asp Gly Ser Gly Pro Leu Lys Pro Phe Val Val
                20                  25                  30

Tyr Cys Asp Ile Arg Glu Asn Arg Ala Trp Thr Val Val Arg His Asp
                35                  40                  45

Arg Leu Trp Thr Thr Arg Val Thr Gly Ser Ser Met Asp Arg Pro Phe
        50                  55                  60

Leu Gly Ala Ile Gln Tyr Trp Asn Ala Ser Trp Glu Val Ser Ala
 65              70                  75                  80

Leu Ala Asn Ala Ser Gln His Cys Glu Gln Trp Ile Glu Phe Ser Cys
                85                  90                  95

Tyr Asn Ser Arg Leu Leu Asn Thr Ala Gly Gly Tyr Pro Tyr Ser Phe
                100                 105                 110

Trp Ile Gly Arg Asn Glu Glu Gln His Phe Tyr Trp Gly Gly Ser Gln
                115                 120                 125

Pro Gly Ile Gln Arg Cys Ala Cys Gly Leu Asp Gln Ser Cys Ile Asp
        130                 135                 140

Pro Ala Leu His Cys Asn Cys Asp Ala Asp Gln Pro Gln Trp
145                 150                 155

<210> SEQ ID NO 23
<211> LENGTH: 130
<212> TYPE: PRT
<213> ORGANISM: Rattus norvegicus

<400> SEQUENCE: 23

Val Ser Phe Tyr Phe Arg Thr Ser Ala Pro Ser Gly Val Phe Leu Glu
 1               5                  10                  15

Asn Met Gly Gly Pro Phe Cys Gln Trp Arg Arg Pro Tyr Val Arg Val
                20                  25                  30

Glu Leu Asn Thr Ser Arg Asp Val Phe Ala Phe Asp Ile Gly Asn
                35                  40                  45

Gly Asp Glu Asn Leu Thr Val His Ser Asp Phe Glu Phe Asn Asp
        50                  55                  60

Asp Glu Trp His Leu Val Arg Ala Glu Ile Asn Val Lys Gln Ala Arg
 65              70                  75                  80

Leu Arg Val Asp His Arg Pro Trp Val Leu Arg Pro Met Pro Leu Gln
                85                  90                  95

Thr Tyr Ile Trp Leu Glu Tyr Asp Gln Pro Leu Tyr Val Gly Ser Ala
                100                 105                 110
```

-continued

Glu Leu Lys Arg Arg Pro Phe Val Gly Cys Leu Arg Ala Met Arg Leu
            115                 120                 125

Asn Gly
    130

<210> SEQ ID NO 24
<211> LENGTH: 25
<212> TYPE: PRT
<213> ORGANISM: Rattus norvegicus

<400> SEQUENCE: 24

Cys Thr His Pro Arg Phe Pro Cys Phe His Gly Gly Arg Cys Val Glu
  1               5                  10                  15

Arg Tyr Ser Tyr Tyr Thr Cys Asp Cys
            20                  25

<210> SEQ ID NO 25
<211> LENGTH: 47
<212> TYPE: PRT
<213> ORGANISM: Rattus norvegicus

<400> SEQUENCE: 25

Pro Val Pro Gly Tyr Glu Pro Gly Tyr Ile Pro Gly Tyr Asp Thr Pro
  1               5                  10                  15

Gly Tyr Val Pro Gly Tyr His Gly Pro Gly Tyr Arg Leu Pro Asp Tyr
            20                  25                  30

Pro Arg Pro Gly Arg Pro Val Pro Gly Tyr Arg Gly Pro Val Tyr
            35                  40                  45

<210> SEQ ID NO 26
<211> LENGTH: 136
<212> TYPE: PRT
<213> ORGANISM: Rattus norvegicus

<400> SEQUENCE: 26

Glu Val Ser Phe Ser Phe Ser Thr Ser Ser Ala Pro Ala Val Leu Leu
  1               5                  10                  15

Tyr Val Ser Ser Phe Val Arg Asp Tyr Met Ala Val Leu Ile Lys Glu
            20                  25                  30

Asp Gly Thr Leu Gln Leu Arg Tyr Gln Leu Gly Thr Ser Pro Tyr Val
            35                  40                  45

Tyr Gln Leu Thr Thr Arg Pro Val Thr Asp Gly Gln Pro His Ser Val
    50                  55                  60

Asn Ile Thr Arg Val Tyr Arg Asn Leu Phe Ile Gln Val Asp Tyr Phe
 65                  70                  75                  80

Pro Leu Thr Glu Gln Lys Phe Ser Leu Leu Val Asp Ser Gln Leu Asp
                85                  90                  95

Ser Pro Lys Ala Leu Tyr Leu Gly Arg Val Met Glu Thr Gly Val Ile
            100                 105                 110

Asp Pro Glu Ile Gln Arg Tyr Asn Thr Pro Gly Phe Ser Gly Cys Leu
            115                 120                 125

Ser Gly Val Arg Phe Asn Asn Val
    130                 135

<210> SEQ ID NO 27
<211> LENGTH: 25
<212> TYPE: PRT
<213> ORGANISM: Rattus norvegicus

<400> SEQUENCE: 27

```
Ile Ala Ile Leu Leu Gly Phe Leu Val Ala Phe Leu Leu Leu Gly Leu
 1               5                  10                  15

Val Gly Met Leu Val Leu Phe Tyr Leu
            20                  25
```

<210> SEQ ID NO 28
<211> LENGTH: 38
<212> TYPE: PRT
<213> ORGANISM: Rattus norvegicus

<400> SEQUENCE: 28

```
Pro Gly Gly Lys Ala Pro Leu Pro Pro Ser Gly Pro Ala Gln Ala Pro
 1               5                  10                  15

Ala Pro Thr Pro Ala Pro Thr Gln Val Pro Thr Pro Ala Pro Ala Pro
            20                  25                  30

Ala Ser Gly Pro Gly Pro
            35
```

<210> SEQ ID NO 29
<211> LENGTH: 10
<212> TYPE: PRT
<213> ORGANISM: Rattus norvegicus

<400> SEQUENCE: 29

```
Gln Asn Leu Pro Gln Ile Leu Glu Glu Ser
 1               5                  10
```

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 30
tcgcaggcta tgagcctggc tacatcc                                            27

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 31
gtgggtaggg gaggtttgct gccagg                                             26

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 32
ggaggtctcc tttag                                                         15